United States Patent
Bencherif et al.

(10) Patent No.: US 9,173,876 B2
(45) Date of Patent: Nov. 3, 2015

(54) PREPARATION AND THERAPEUTIC APPLICATIONS OF (2S,3R)-N-2-((3-PYRIDINYL)METHYL)-1-AZABICYCLO-[2.2.2]OCT-3-YL)-3,5-DIFLUOROBENZAMIDE

(71) Applicant: Targacept, Inc., Winston-Salem, NC (US)

(72) Inventors: Merouane Bencherif, Winston-Salem, NC (US); Nikolai Federov, Winston-Salem, NC (US); Terry Hauser, Winston-Salem, NC (US); Kristen G. Jordan, Clemmons, NC (US); Sharon Rae Letchworth, Kernersville, NC (US); Anatoly Mazurov, Greensboro, NC (US); Julio A. Munoz, Walnut Cove, NC (US); Jason Speake, Winston-Salem, NC (US); Daniel Yohannes, Winston-Salem, NC (US)

( * ) Notice: Subject to any disclaimer, the term of this patent is extended or adjusted under 35 U.S.C. 154(b) by 0 days.

(21) Appl. No.: 14/518,049

(22) Filed: Oct. 20, 2014

(65) Prior Publication Data

US 2015/0105421 A1    Apr. 16, 2015

Related U.S. Application Data

(63) Continuation of application No. 13/893,382, filed on May 14, 2013, now Pat. No. 8,901,151, which is a continuation of application No. 12/740,970, filed as application No. PCT/US2010/021926 on Jan. 25, 2010, now Pat. No. 8,476,296.

(60) Provisional application No. 61/147,260, filed on Jan. 26, 2009.

(51) Int. Cl.
*A61K 31/439* (2006.01)
*A61K 31/444* (2006.01)
*C07D 453/02* (2006.01)

(52) U.S. Cl.
CPC ............ *A61K 31/444* (2013.01); *C07D 453/02* (2013.01)

(58) Field of Classification Search
CPC .................................................... A61K 31/439
USPC ......................................... 514/305
See application file for complete search history.

(56) References Cited

U.S. PATENT DOCUMENTS

| | | | |
|---|---|---|---|
| 4,203,990 A | 5/1980 | Yen | |
| 4,922,901 A | 5/1990 | Brooks et al. | |
| 4,970,315 A | 11/1990 | Schmidhalter | |
| 5,212,188 A | 5/1993 | Caldwell et al. | |
| 5,217,975 A | 6/1993 | Wadsworth et al. | |
| 5,219,849 A | 6/1993 | Lotti et al. | |
| 5,276,043 A | 1/1994 | Lippiello et al. | |
| 5,346,906 A | 9/1994 | Baker et al. | |
| 5,510,355 A | 4/1996 | Bencherif et al. | |
| 5,567,724 A | 10/1996 | Kelleher et al. | |
| 5,583,140 A | 12/1996 | Bencherif et al. | |
| 5,597,919 A | 1/1997 | Dull et al. | |
| 5,604,231 A | 2/1997 | Smith et al. | |
| 5,616,707 A | 4/1997 | Crooks et al. | |
| 5,616,716 A | 4/1997 | Dull et al. | |
| 5,663,356 A | 9/1997 | Ruecroft et al. | |
| 5,709,853 A | 1/1998 | Iino et al. | |
| 5,712,270 A | 1/1998 | Sabb | |
| 5,733,255 A | 3/1998 | Dinh et al. | |
| 5,741,802 A | 4/1998 | Kem et al. | |
| 5,811,442 A | 9/1998 | Bencherif et al. | |
| 5,824,692 A | 10/1998 | Lippiello et al. | |
| 5,852,041 A | 12/1998 | Cosford et al. | |
| 5,853,696 A | 12/1998 | Elmaleh et al. | |
| 5,859,004 A | 1/1999 | Olesen | |
| 5,861,423 A | 1/1999 | Caldwell et al. | |
| 5,902,814 A | 5/1999 | Gordon et al. | |
| 5,952,339 A | 9/1999 | Bencherif et al. | |
| 5,969,144 A | 10/1999 | London et al. | |
| 5,977,144 A | 11/1999 | Meyer et al. | |
| 5,998,429 A | 12/1999 | Macor et al. | |
| 6,054,434 A | 4/2000 | Kropp et al. | |
| 6,054,464 A | 4/2000 | Macor et al. | |
| 6,096,728 A | 8/2000 | Collins et al. | |
| 6,110,914 A | 8/2000 | Phillips et al. | |
| 6,166,043 A | 12/2000 | Ikeda et al. | |
| 6,166,048 A | 12/2000 | Bencherif | |

(Continued)

FOREIGN PATENT DOCUMENTS

EP          052C555        9/1999
IN          173570 A1      6/1994

(Continued)

OTHER PUBLICATIONS

Abdipranoto A, Wu S, Stayte S, Vissel B, The role of neurogenesis in neurodegenerative diseases and its implications for therapeutic development *CNS Neural Disord Drug Targets* 7:187-210 (2008).

Abel, K., et al., "Enhancement of the Prolactin Response tod-Fenfluramine in Drug-Naïve Schizophrenic Patients," *British Journal of Psychiatry*, 168: 57-60 (1996).

Abi-Dargham, A., et al., "SPECT Imaging of Dopamine Transporters in Human Brain with Iodine-123-Fluoroalkyl Analogs of Beta-CIT," *J. Nucl. Med.*, 37(7): 1129-33 (1996).

Abi-Dargham, A., et al., "Striatal Amphetamine-Induced Dopamine Release in Patients with Schizotypal Personality Disorder Studied with Single Photon Emission Computed Comography and [123I]iodobenzamide," *Biol. Psychiatry*, 55 (10): 1001-1006 (2004).

(Continued)

*Primary Examiner* — Niloofar Rahmani

(74) *Attorney, Agent, or Firm* — BRINKS GILSON & LIONE

(57) ABSTRACT

The present invention relates to compounds that bind to and modulate the activity of neuronal nicotinic acetylcholine receptors, to processes for preparing these compounds, to pharmaceutical compositions containing these compounds, and to methods of using these compounds for treating a wide variety of conditions and disorders, including those associated with dysfunction of the central nervous system (CNS).

1 Claim, 23 Drawing Sheets

(56) References Cited

U.S. PATENT DOCUMENTS

| | | | |
|---|---|---|---|
| 6,232,319 B1 | 5/2001 | Marazano et al. | |
| 6,310,043 B1 | 10/2001 | Bundle et al. | |
| 6,369,224 B1 | 4/2002 | Phillips et al. | |
| 6,407,095 B1 | 6/2002 | Lochead et al. | |
| 6,432,975 B1 | 8/2002 | Schmitt et al. | |
| 6,441,049 B2 | 8/2002 | Reitz et al. | |
| 6,479,172 B2 | 11/2002 | Hu et al. | |
| 6,479,510 B2 | 11/2002 | Myers et al. | |
| 6,486,172 B2 | 11/2002 | Myers et al. | |
| 6,492,385 B2 | 12/2002 | Myers et al. | |
| 6,492,386 B2 | 12/2002 | Myers et al. | |
| 6,500,840 B2 | 12/2002 | Myers et al. | |
| 6,525,065 B1 | 2/2003 | Caldwell et al. | |
| 6,538,003 B1 | 3/2003 | Galli et al. | |
| 6,552,012 B2 | 4/2003 | Peters et al. | |
| 6,562,816 B2 | 5/2003 | Wishka et al. | |
| 6,569,865 B2 | 5/2003 | Eifion | |
| 6,599,916 B2 | 7/2003 | Myers et al. | |
| 6,610,713 B2 | 8/2003 | Tracey | |
| 6,624,167 B1 | 9/2003 | Clark et al. | |
| 6,635,645 B1 | 10/2003 | Lochead et al. | |
| 6,683,090 B1 | 1/2004 | Balestra et al. | |
| 6,703,502 B2 | 3/2004 | Phillips et al. | |
| 6,706,878 B2 | 3/2004 | Phillips et al. | |
| 6,734,215 B2 | 5/2004 | Shytle et al. | |
| 6,838,471 B2 | 1/2005 | Tracey | |
| 6,881,734 B2 | 4/2005 | O'Neill et al. | |
| 6,953,855 B2 | 10/2005 | Mazurov et al. | |
| 6,987,106 B1 | 1/2006 | Gallet et al. | |
| 6,995,167 B2 | 2/2006 | Loch, III et al. | |
| 7,001,914 B2 | 2/2006 | Phillips et al. | |
| 7,067,515 B2 | 6/2006 | Wishka et al. | |
| 7,115,629 B2 | 10/2006 | Farrerons Gallemi et al. | |
| 7,160,876 B2 | 1/2007 | Ji et al. | |
| 7,176,198 B2 | 2/2007 | Piotrowski et al. | |
| 7,186,836 B2 | 3/2007 | Chang et al. | |
| 7,196,096 B2 | 3/2007 | Loch, III et al. | |
| 7,309,699 B2 | 12/2007 | Ji et al. | |
| 7,425,561 B2 | 9/2008 | Mazurov et al. | |
| 7,732,607 B2 | 6/2010 | Mazurov et al. | |
| 7,767,193 B2 | 8/2010 | Mazurov et al. | |
| 8,476,296 B2 * | 7/2013 | Bencherif et al. | 514/305 |
| 8,901,151 B2 * | 12/2014 | Bencherif et al. | 514/305 |
| 2001/0056084 A1 | 12/2001 | Allgeier et al. | |
| 2002/0016344 A1 | 2/2002 | Tracey | |
| 2002/0040035 A1 | 4/2002 | Myers et al. | |
| 2002/0086871 A1 | 7/2002 | O'Neill et al. | |
| 2003/0105089 A1 | 6/2003 | Wishka et al. | |
| 2003/0119837 A1 | 6/2003 | O'Neill et al. | |
| 2003/0130305 A1 | 7/2003 | Walker et al. | |
| 2003/0149065 A1 | 8/2003 | Loch, III et al. | |
| 2003/0153595 A1 | 8/2003 | Walker et al. | |
| 2003/0176416 A1 | 9/2003 | Peters et al. | |
| 2003/0176702 A1 | 9/2003 | Walker et al. | |
| 2004/0002513 A1 | 1/2004 | Mazurov et al. | |
| 2005/0255040 A1 | 11/2005 | Mazurov et al. | |
| 2008/0132551 A1 | 6/2008 | Rogers et al. | |
| 2008/0138287 A1 | 6/2008 | Mazurov et al. | |

FOREIGN PATENT DOCUMENTS

| | | |
|---|---|---|
| WO | WO-91/12254 A1 | 8/1991 |
| WO | WO-92/15306 A1 | 9/1992 |
| WO | WO-94/05288 A1 | 3/1994 |
| WO | WO-9408992 A1 | 4/1994 |
| WO | WO-95/03306 A1 | 2/1995 |
| WO | WO-96/06098 A1 | 2/1996 |
| WO | WO-96/12711 A1 | 5/1996 |
| WO | WO-9631475 A2 | 10/1996 |
| WO | WO-9640682 A1 | 12/1996 |
| WO | WO-97/01556 A1 | 1/1997 |
| WO | WO-97/11072 A1 | 3/1997 |
| WO | WO-97/30998 A1 | 8/1997 |
| WO | WO-9825619 A1 | 6/1998 |
| WO | WO-98/54181 A1 | 12/1998 |
| WO | WO-99/00385 A1 | 1/1999 |
| WO | WO-99/03859 A1 | 1/1999 |
| WO | WO-99/10338 A2 | 3/1999 |
| WO | WO-99/51602 A1 | 10/1999 |
| WO | WO-99/62505 A2 | 12/1999 |
| WO | WO-00/34276 A1 | 6/2000 |
| WO | WO-00/42044 A1 | 7/2000 |
| WO | WO-00/58311 A1 | 10/2000 |
| WO | WO-01/36417 A1 | 5/2001 |
| WO | WO-01/85727 A1 | 11/2001 |
| WO | WO-02/15662 A2 | 2/2002 |
| WO | WO-02/16355 A1 | 2/2002 |
| WO | WO-02/16355 A2 | 2/2002 |
| WO | WO-02/16356 A1 | 2/2002 |
| WO | WO-02/16356 A2 | 2/2002 |
| WO | WO-02/16357 A2 | 2/2002 |
| WO | WO-02/16358 A1 | 2/2002 |
| WO | WO-02/16358 A2 | 2/2002 |
| WO | WO-02/17358 A2 | 2/2002 |
| WO | WO-02/44176 A1 | 6/2002 |
| WO | WO-02/051841 A1 | 7/2002 |
| WO | WO-02/057275 A1 | 7/2002 |
| WO | WO-02/096912 A1 | 12/2002 |
| WO | WO-03/018585 A1 | 3/2003 |
| WO | WO-03/018586 A1 | 3/2003 |
| WO | WO-03/022856 A1 | 3/2003 |
| WO | WO-03/032897 A2 | 4/2003 |
| WO | WO-03/070731 A2 | 8/2003 |
| WO | WO-03/070732 A1 | 8/2003 |
| WO | WO-03/072578 A1 | 9/2003 |
| WO | WO-03/078431 A1 | 9/2003 |
| WO | WO-03/087102 A1 | 10/2003 |
| WO | WO-03/087103 A1 | 10/2003 |
| WO | WO-03/087104 A1 | 10/2003 |
| WO | WO-2004/016608 A1 | 2/2004 |
| WO | WO-2004/016616 A1 | 2/2004 |
| WO | WO-2004/016617 A1 | 2/2004 |
| WO | WO-2004/019943 A1 | 3/2004 |
| WO | WO-2004/029050 A1 | 4/2004 |
| WO | WO-2004/039366 A1 | 5/2004 |
| WO | WO-2004/039815 A2 | 5/2004 |
| WO | WO-2004/052348 A2 | 6/2004 |
| WO | WO-2004/052365 A2 | 6/2004 |
| WO | WO-2004/052461 A1 | 6/2004 |
| WO | WO-2004/052894 A1 | 6/2004 |
| WO | WO-2004/061510 A1 | 7/2004 |
| WO | WO-2004/061511 A1 | 7/2004 |
| WO | WO-2004/076449 A2 | 9/2004 |
| WO | WO-2004/076453 A2 | 9/2004 |
| WO | WO-2004/099202 A1 | 11/2004 |
| WO | WO-2005/005435 A1 | 1/2005 |
| WO | WO-2005/030778 A1 | 4/2005 |
| WO | WO-2005/042538 A1 | 5/2005 |
| WO | WO-2005/066166 A2 | 7/2005 |
| WO | WO-2005/066167 A2 | 7/2005 |
| WO | WO-2005/066168 A1 | 7/2005 |
| WO | WO-2005/111038 A2 | 11/2005 |
| WO | WO-2006/001894 A1 | 1/2006 |
| WO | WO-2006/065209 A1 | 6/2006 |
| WO | WO-2006/069097 A2 | 6/2006 |
| WO | WO-2006/133303 A1 | 12/2006 |
| WO | WO-2007/018738 A2 | 2/2007 |
| WO | WO-2007/024814 A1 | 3/2007 |
| WO | WO-2007/038367 A1 | 4/2007 |
| WO | WO-2008/138287 A1 | 11/2008 |
| WO | WO-2009140201 A1 | 11/2009 |
| WO | WO-2011/036167 A1 | 3/2011 |

OTHER PUBLICATIONS

Acker, B.A., et al., "Discovery of N-[3R,5R)-1-azabicyclo[3.2.1]oct-3-yl]furo[2,3-c]pyridine-5- carboxamide as an agonist of the alpha7 nicotinic acetylcholine receptor: in vitro and in vivo activity," Bioorg. Med. Chem. Lett. 18: 3611-3615 (2008).

Adams CE, Broide RS, Chen Y, Winzer-Serhan UH, Henderson TA, Leslie FM, Freedman R., Development of the alpha7 nicotinic cholinergic receptor in rat hippocampal formation, *Brain Res Dev Brain Res* 139: 175-87 (2002).

(56) References Cited

OTHER PUBLICATIONS

Addy, N.A., et al., "Nicotinic mechanisms of memory: effects of acute local DhbetaE and MLA infusions in the basolateral amygdala," *Brain Res. Cogn. Brain Res.* 16: 51-57 (2003).
Adler, L.E. et al., "Schizophrenia, sensory gating and nicotinic receptors." *Schizophr. Bull.* 24:189-202 (1998).
Ahima, R.S., Qi, Y. & Singhal, N.S., "Adipokines that link obesity and diabetes to the hypothalamus," *Prog. Brain Res*, 153, 155-174 (2006).
Alkondon, M., et al., "Choline is a Selective Agonist of a7 Nicotinic Acetylcholine Receptors in the Rat Brain Neurons," *Eur. J. Neurosci.*, 9(12): 2734-2742 (1997).
American Diabetes Association, "Consensus Development Conference on Antipsychotic Drugs and Obesity and Diabetes," *Diabetes Care*, 27(2): 596-601 (2004).
Antonica, A., et al., "Vagal Control of Lymphocyte Release from Rat Thymus," Journal of the Autonomous Nervous System, 48(3):187-197 (1994).
Arendash G.W., et al., "Improved learning and memory in aged rats with chronic administration of nicotinic receptor agonist GTS-21," Brain Res. 674: 252-259 (1995).
Arnaiz-Cot, J.J., et al., "Allosteric modulation of alpha 7 nicotinic receptors selectively depolarizes hippocampal interneurons, enhancing spontaneous GABAergic transmission," Eur. J. Neurosci., 27: 1097-1110 (2008).
Asante-Appiah, E. & Kennedy, B.P., "Protein tyrosine phosphatases: the quest for negative regulators of insulin action," Am. J. Physiol. Endocrinol. Metabol. 284:, E663-E670 (2003).
Astles, P.C., et al., "Recent Progress in the Development of Subtype Selective Nicotinic Acetylcholine Receptor Ligands," Current Drug Targets: CNS & Neurological Disorders, 1(4): 337-348 (2002).
Avila, M.T. et al., "Effects of Nicotine on Leading Saccades during Smooth Pursuit Eye Movements in Smokers and Nonsmokers with Schizophrenia," Neuropsychopharmacol. 28: 2184-2191 (2003).
Banerjee, S. A., et al., "5' flanking sequences of the rat tyrosine hydroxylase gene target accurate tissue-specific, developmental, and transsynaptic expression in transgenic mice." J. Neurosci., 12 (11): 4460-4467 (2003).
Banes, A.K., et al., "Angiotensin II blockade prevents hyperglycemia-induced activation of JAK and STAT proteins in diabetic rat kidney glomerul," *Am. J. Physiol. Renal. Physiol.* 286: F653-F659 (2004).
Barnes, Peter J., Int. "Nuclear Factor-$_K$B," J. Biochem. Cell Biol., vol. 29, No. 6, pp. 867-870 (1997).
Barnes, T., et al., "Pharmacological strategies for relapse prevention in schizophrenia," Psychiatry 6: 351-356 (2007).
Bartfai, A., et al., "Bilateral Skin Conductance Activity, Clinical Symptoms and CSF Monoamine Metabolite Levels in Unmedicated Schizophrenics," *Biological Psychology*, 18: 201-218 (1984).
Bartholomeusz, C. et al., "Bcl-2 antisense oligonucleotide overcomes resistance to E1A gene therapy in a low HER2-expressing ovarian cancer xenograft model," *Cancer Res.* 65: 8406-8413 (2005).
Beckstead, R. M., et al., "Efferent connections of the substantia nigra and ventral tegmental area in the rat," *Brain Res.*, 175(2): 191-217 (1979).
Behrendt, R.P., et al., "Dysregulation of thalamic sensory 'transmission' in schizophrenia: neurochemical vulnerability to hallucinations," *J. Psychopharmacol.*, 20: 356-72 (2006).
Belluardo, N., et al., "Neurotrophic effects of central nicotinic receptor activation," *J. Neural. Transm. Suppl.* 60: 227-245 (2000).
Bence, K.K. et al., "Neuronal PTP1B regulates body weight, adiposity and leptin action," *Nat. Med.*, 12: 917-924 (2006).
Bencherif, M., et al., The Heterocyclic substituted Pyridine Derivative (±)-2-(-3-pyridinyl)-1-Azabicyclo[2.2.2]octane (RJR-2429): A Selective Ligand at Nicotinic Acetylcholine Receptors, JPET 284(3): 886-894 (1998).
Bergis, O.E., et al., "SSR180711A, A Novel and Selective α7 Nicotinic Receptor Partial Agonist. II. Effects in Models Predictive of Therapeutic Activity oon Cognitive Symptoms of Alzheimer's Disease," *Soc. Neurosci. Abstr.*,34: 583.2 (2004).

Bettany, J.H. and E.D. Levin, "Ventral Hippocampal α7 Nicotinic Receptor Blockade and Chronic Nicotine Effects on Memory Performance in the Radial-Arm Maze," *Pharm. Bio. Behavior*, 70: 467-474 (2001).
Bialowas, J., et al., "The relationship between catecholamine levels in the hypothalamus and amygdala under influence of glucose overloading in hungry and sated rats," Pol. J. Pharmacol. Pharm. 31(4): 325-35 (1979).
Birtwistle, Jon, Postgrad Med. J., "The role of cigarettes and nicotine in the onset and treatment of ulcerative colitis," vol. 72, pp. 714-718 (1996).
Bitner, R.S., et al., "Broad-spectrum efficacy across cognitive domains by alpha7 nicotinic acetylcholine receptor agonism correlates with activation of ERK1/2 and CREB phosphorylation pathways," *J. Neurosci.* 27: 10578-10587 (2007).
Blumenthal, E.M., et al., "Detection of Functional Nicotinic Receptors Blocked by □-Bungarotoxin on PC12 Cells and Dependence of Their Expression on Post-Translational Events," *J. Neurosci.*, 17: 6094-6104 (1997).
Boess, et. al., "The novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," The Journal of Pharmacology and Experimental Therapeutics, 321(2): 716-725 (2007).
Bogerts, B., et al., "A morphometric study of the dopamine-containing cell groups in the mesencephalon of normals, Parkinson patients, and schizophrenics," *Biol. Psychiatry* 18 (9): 951-969 (1983).
Borovikova, L.V. et al., "Role of vagus nerve signaling in CNI-1493-mediated suppression of acute inflammation," *Autonomic Neurosci.: Basic and Clinical*, 85: 141-147 (2000).
Borovikova, L.V., et al., "Role of the Vagus Nerve in the Anti-Inflammatory Effects of CNI-1493," Proceedings of the Annual Meeting of Professional Research Scientists: Experimental Biology, Abstract 97.9 (2000).
Borovikova, L.V., et al., "Vagus Nerve Stimulation Attenuates the Systemic Inflammatory Response to Endotoxin," Nature, 405(25):458-462 (2000).
Braff, D.L., et al., "Sensorimotor gating and schizophrenia: human and animal model studies," *Arch. Gen. Psych.* 47:181-188 (1990).
Breese, C.R. et al."Comparison of the Regional Expression of Nicotinic Acetylcholine Receptor a7 mRNA and [125I]-a-Bungarotoxin Binding in Human Postmortem Brain," J. Com. Neurol. 387: 385-398 (1997).
Breining, S.R., et al., "Neuronal Nicotinic Acetylcholine receptor Modulators: Recent Advances and Therapeutic Potential," Annual Rep. in Med. Chem. 40: 3-16 (2005).
Briceno et al. Surgical Neurology (2007), 67(4), 388-391.
Briggs, C., et al., "Functional Characterization of the Novel Neuronal Nicotinic Acetylcholine Recptor Ligand GTS-21 in Vitro and in Vivo," Pharm. Bio. Behavoir, 57(1/2): 231-241 (1997).
Broad, Lisa M, et al., "PSAB-OFP, a selective a7 nicotinic receptor agonist, is also a potent agonist of the 5-HT3 receptor," Eur. J. Pharmacol., 452(2): 137-1'44 (2002).
Broadley, K.J. and D. R. Kelly, "Muscarinic Receptor Agonists and Antagonists," Molecules 6: 142-193 (2001).
Broderick, P.A., et al., "I. Serotonin (5-HT) within dopamine reward circuits signals open-field behavior. II. Basis for 5-HT—DA interaction in cocaine dysfunctional behavior," *Neurosci. Biobehav. Rev.* 21(3): 227-260 (1997).
Bruel-Jungerman E, Rampon C, Laroche S, Adult hippocampal neurogenesis, synaptic plasticity and memory: facts and hypothesis, *Rev Neurosci* 18: 93-114 (2007).
Bunney, E. B., et al., "Electrophysiological effects of cocaethylene, cocaine, and ethanol on dopaminergic neurons of the ventral tegmental area," *J. Pharmacol. Exp. Ther.* 297(2): 696-703 (2001).
Cabib, S., et al., "Behavioral and mesocorticolimbic dopamine responses to non aggressive social interactions depend on previous social experiences and on the opponent's sex," *Behav. Brain Res.* 112(1-2): 13-22 (2000).
Caldarone BJ, Harrist A, Cleary MA, Beech RD, King SL, Picciotto MR, High-affinity nicotinic acetylcholine receptors are required for

(56) References Cited

OTHER PUBLICATIONS antidepressant effects of amitriptyline on behavior and hippocampal cell proliferation, *Biological Psychiatry* 5: 657-664 (2004).
Canitano, R., "Clinical Experience With Topiramate to Counteract Neuroleptic Induced Weight Gain in 10 Individuals With Autistic Spectrum Disorders," *Brain & Development*, 27: 228-232 (2005).
Carlsson, A., "Does dopamine play a role in schizophrenia?" *Psychol. Med.* 7(4): 58397 (1977).
CAS Printout for Begue et al., Dec. 1969.
CAS Printout for IN 173 570, Jun. 4, 1994.
CAS Printout for Schmidhalter et al., Nov. 1990.
Caulfield, M.P. "Muscarinic Receptors-Characterization, Coupling and Function," *Pharma. Ther.* 58: 319-379 (1993).
Cheng, A. et al., Attenuation of leptin action and regulation of obesity by Protein-tyrosine Phosphatase 1B, Dev.Cell, 2, 497-503 (2002).
Cheng, Yung-Chi, and W.H. Prusoff, "Relationship Between the Inhibition Constant ($K_I$) and the Concentration of Inhibitor which Causes 50 Per Cent inhibition ($I_{50}$) of an Enzymatic Reaction," *Biochem. Pharmacol.* 22(23): 3099-3108 (1973).
Cho-Chung Y.S., et al., "Oligonucleotides as transcription factor decoys," *Curr. Opin. Mol. Ther.* 1: 386-392 (1999).
Cilia, J., et al., "Reversal of Isolation-Rearing-Induced PPI Deficits by an α7 Nicotinic Receptor Agonist," Psychopharmacology, 182: 214-219 (2005).
Cincotta, Stephanie L., et al., Selective Nicotinic Acetylcholine Receptor Agonists: Potential therapies for neuropsychiatric disorders with cognitive dysfunction, Current Opinion in Investigational Drugs, 9(1):47-56 (2008).
Cooper-Kuhn CM, Winkler J, Kuhn HG, Decreased neurogenesis after cholinergic forebrain lesion in the adult rat, J Neurosci Res 77: 155-65 (2004).
Corbett R., et al., "Antipsychotic agents antagonize non-competitive N-methyl-D-aspartate antagonist-induced behaviors," Psychopharmacol. 120: 67-74 (1995).
Corso, T. D., et al., "Transfection of tyrosine kinase deleted FGF receptor-1 into rat brain substantia nigra reduces the number of tyrosine hydroxylase expressing neurons and decreases concentration levels of striatal dopamine," *Brain Res. Mol Brain Res.* 139(2): 361-266 (2005).
Dadke, S., et al., "Down-regulation of insulin signaling by Protein-tyrosine Phosphatase 1B is mediated by an N-terminal binding region," *J. Biol. Chem.* 275: 23642-23647 (2000).
Dalack, G.W., et al., "Nicotine dependence in schizophrenia: clinical phenomena and laboratory findings," *Am. J. Psych.* 155:1490-1501 (1998).
Dandona, P., et al., "Inflammation: the link between insulin resistance, obesity and diabetes," *Trends Immunol.*, 25: 4-7 (2004).
Danesh F.R., et al., "3-Hydroxy-3-methylglutaryl CoA reductase inhibitors prevent high glucose-induced proliferation of mesangial cells via modulation of Rho GTPase/ p21 signaling pathway: Implications for diabetic nephropathy," *Proc. Natl. Acad. Sci. U.S.A.* 99: 8301-8305 (2002).
Dani, J.A., et al., "Nicotinic acetylcholine receptors and nicotinic cholinergic mechanisms of the central nervous system," *Annu. Rev. Pharmacol. Toxicol.* 47: 699-729 (2007).
Davies, Andrew R.L., et al., "Characterisation of the binding of [$^3$H]methyllycaconitine: a new radioligand for labeling α7-type neuronal nicotinic acetylcholine receptors," *Neuropharmacol.* 38: 679-690 (1999).
Davis, K. L., et al., "Dopamine in schizophrenia: a review and reconceptualization," *Am. J. Psychiatry* 148(11): 1474-1486 (1991).
de Fiebre C.M., "Characterization of a series of anabaseine-derived compounds reveals that the 3-(4)-dimethylaminocinnamylidine derivative is a selective agonist at neuronal nicotinic α7/125I-α-bungarotoxin receptor subtypes," *Mol. Pharmacol.* 47: 164-171 (1995).
de Fiebre NC, de Fiebre CM, Alpha 7 nicotinic acetylcholine receptor-mediated protection against ethanol-induced neurotoxicity, *Alcohol* 31: 149-53 (2003).

de Jonge, W.J. et al, "The alpha7 nicotinic acetylcholine receptor as a pharmacological target for inflammation," *British J. Pharmacol.*, 151: 915-929 (2007).
de Jonge, W.J. et al., "Stimulation of the vagus nerve attenuates macrophage activation by activating the Jak2-STAT3 signaling pathway," *Nat. Immunol.*, 6: 844-851 (2005).
De Luca, V, et al., "Evidence of Association between Smoking and Nicotinic Receptor Subunit Gene in Schizophrenia Patients," Neuropsychopharmacol. 29: 1522-1526 (2004).
Dean, B., "Signal Transmission, Rather Than Reception, Is the Underlying Neurochemical Abnormality in Schizophrenia," *Aust. NZ J. Psychiatry*, 34(4): 560-9 (2000).
Decker et al., The Potential of Neuronal Nicotinic Acetylcholine Receptor Agonists for Treating CNS Conditions, Expert Opinion on Drug Discovery Sep. 2008, vol. 3, No. 9, pp. 1027-1040.
Deigner H.P., et al., "Apoptosis modulators in the therapy of neurodegenerative diseases," *Expert Opin. Investig. Drugs* 9: 747-764 (2000).
Dickinson, J.A., et al., "Presynaptic alpha 7- and beta 2-containing nicotinic acetylcholine receptors modulate excitatory amino acid release from rat prefrontal cortex nerve terminals via distinct cellular mechanisms," *Mol. Pharmacol.* 74: 348-359 (2008).
Doherty, M. D., et al., "Ultrastructural localization of the serotonin 2A receptor in dopaminergic neurons in the ventral tegmental area," *Brain Res.* 864(2): 176-85 (2000).
Dolle, F., et al., "Synthesis and Preliminary Evaluation of a Carbon-11-labelled Agonist of the a-7 Nicotinic Acetylcholine Receptor," *J. Labelled Comp. Radiopharm.* 44:785-795 (2001).
Donnelly-Roberts D.L., et al., "In vitro neuroprotective properties of the novel cholinergic channel activator (ChCA), ABT-418," *Brain Res* 719: 36-44 (1996).
Dowling O, Rochelson B, Way K, Al-Abed Y, Metz CN, Nicotine inhibits cytokine production by placenta cells via NF-kappaB: potential role in pregnancy-induced hypertension, Mol Med 13: 576-83 (2007).
Dube, N. & Tremblay, M.L., "Beyond the metabolic function of PTP1B," *Cell Cycle* 3: 550-553 (2004).
Durany, N., et al., "Human post-mortem striatal alpha4beta2 nicotinic acetylcholine receptor density in schizophrenia and Parkinson's syndrome," *Neurosci. Lett.* 287: 109-112 (2000).
Ebadi, M. et al., "Neurotrophins and Their Receptors in Nerve Injury and Repair," *Neurochem Int.*, vol. 30, Nos. 4/5, pp. 347-374 (1997).
Egea, J., et al., "Neuroprotection Afforded by Nicotine Against Oxygen and Glucose Deprivation in Hippocampal Slices Is Lost in α7 Nicotinic Receptor Knockout Mice," *Neuroscience* 145: 866-872 (2007.
Ehninger D, Kempermann G, Neurogenesis in the adult hippocampus, Cell Tissue Res 331: 243-50 (2008).
Elchebly, M. et al., "Increased insulin sensitivity and obesity resistance in mice lacking the protein tyrosine phosphatase-1B gene," Science 283: 1544-1548 (1999).
Elder GA, Gama Sosa MA, Research update: neurogenesis in adult brain and neuropsychiatric disorders, Mt Sinai J Med 73: 931-40 (2006).
Ennaceur, A., et al., "A new one-trial test for neurobiological studies of memory in rats. II: effects of piracetam and pramiracetam," Behavioural Brain Research, 33: 197-207 (1988).
Epstein, M. and V.M. Campese, "Pleiotropic effects of 3-hydroxy-3-methylglutaryl coenzyme a reductase inhibitors on renal function," Am. J. Kidney Dis. 45: 2-14 (2005).
Evans, et al., Isotopic labeling with carbon-14 and tritium, Principles of Radiopharmacology, 1992, p. 11-13.
Fang, X., et al., "Control of CREB-binding protein signaling by nuclear fibroblast growth factor receptor-1: a novel mechanism of gene regulation," J. Biol. Chem. 280(31): 28451-62 (2005).
Farde, L.,et al., "Quantitative analysis of D2 dopamine receptor binding in the living human brain by PET," Science 231: 258-261 (1986).
Fenton, W.S. and B. Lee, "Can Clozapine Response Be Predicted? A Naturalistic Pilot Study," *J. Nervous & Mental Disease*: 181(1): 62-63 (1993).

(56) References Cited

OTHER PUBLICATIONS

Fenton, W.S., of al., "Breaking the Log-Jam in Treatment Development for Cognition in Schizophrenia: NIMH Perspective," *Psychopharmacology*, 169:365-366 (2003).

Fleshner, M., et al., "Thermogenic and Corticosterone Responses to Intravenous Cytokines (IL-1 Beta and TNF-Alpha) are Attenuated by Subdiaphragmatic Vagotomy," Journal of Neuroimmunology, 86:134-141 (1998).

Fornari, A. et al., "Nicotine withdrawal increases body weight, neuropeptide Y and Agouti-related protein expression in the hypothalamus and decreases uncoupling protein-3 expression in the brown adipose tissue in high-fat fed mice," *Neurosci. Lett.*, 411: 72-76 (2007).

Francis, Michael M., of al., "Specific Activation of the a7 Nicotinic Acetylcholine Receptor by a Quaternary Analog of Cocaine," *Mol. Pharmacol.*, 60(1): 71-79 (2001).

Freedman, R., of al., "Evidence in Postmortem Brain Tissue for Decreased Numbers of Hippocampal Nicotinic Receptors in Schizophrenia," *Biol. Psychiatry* 38(1): 22-33 (1995).

Freedman, R., et al., "Initial phase 2 trial of a nicotinic agonist in schizophrenia," *Am. J. Psych*. 165: 1040-1047 (2008).

Freedman, R., et al., "The alpha7-nicotinic acetylcholine receptor and the pathology of hippocampal interneurons in schizophrenia," *J. Chem. Neuroanat*. 20: 299-306 (2000).

Gahring, Lorise C. and Rogers, Scott W., Neuronal Nicotinic Acetylcholine Receptor Expression and Function on Nonneuronal Cells, AAPS Journal 7(4): 885-894 (2006).

Gallowitsch-Puerta, M. and K.J.Tracey, "Immunologic role of the cholinergic anti-inflammatory pathway and the nicotinic acetylcholine alpha 7 receptor," *Ann. N.Y. Acad. Sci*. 1062: 209-19 (2005).

Garcia-Roman N, et al., "Lovastatin Induces Apoptosis of Spontaneously Immortalized Rat Brain Neuroblasts: Involvement of Nonsterol Isoprenoid Biosynthesis Inhibition," *Molecular and Cellular Neuroscience* 17: 329-341 (2001).

Gatto GJ, Bohme GA, Caldwell WS, Letchworth SR, Traina VM, Obinu MC, Laville M, Reibaud M, Pradier L, Dunbar G, Bencherif M, TC-1734: An orally active neuronal nicotinic acetylcholine receptor modulator with antidepressant, neuroprotective and long-lasting cognitive effects. CNS Drug Rev 10:147-66 (2004).

Gaughran, F., et al., "Hippocampal FGF-2 and FGFR1 mRNA expression in major depression, schizophrenia and bipolar disorder," *Brain Res. Bull*. 70(3): 221-227 (2006).

Gaykema, R.P., et al., "Subdiaphragmatic Vagotomy Suppresses Endotoxin-Induced Activation of Hypothalamic Corticotropin-Releasing Hormone Neurons and ACTH Secretion," Endocrinology, 136(10):4717-4720 (1995).

Geyer, M.A., et al., "Measurement of startle response, prepulse inhibition and habituation," *Current Protocols Neurosci*. 8: 7.1-7.15 (1998).

Gotti Cecilia, et al., Expression of Nigrostriatal a6-Containing Nicotinic Acetylcholine Receptors Is Selectively Reduced, but No Eliminated, by rs3 Subunit Gene Deletion, Mol. Pharmacol. 67(6): 2007-2015 (2005).

Graham, K., et al., "Double-Blind, Placebo-Controlled Investigation of Amantadine for Weight Lose in Subjects Who Gained Weight With Olanzapie," *Am. J. Psy*., 162(9): 1744-1746 (2005).

Guan, Z.Z., et al., "Decreased protein level of nicotinic acetylcholine receptor α7 subunit in the frontal cortex from schizophrenic brain," *NeuroReport*., 10: 1779-1782 (1999).

Guslandi, M., "Nicotine Treatment for Ulcerative Colitis," Br. J. Clin. Pharmacol., 48:481-484 (1999).

Hajos, M., et al., "The Selective α7 Nicotonic Acetylcholine Receptor Agonist PNU-282987 [N-[(3R)-1-Azabicyclo[2.2.2]oct-3-yl]-4-chlorobenzamide Hydrochloride] . . ." *J. Pham. Exper. Thera.*, 312(3): 1213-1222 (2005).

Hanisch, Uwe-Karsten et al., "Modulation of Hippocampal Acetylcholine Release: A Potent Central Action of Interleukin-2," The Journal of Neuroscience, vol. 13(8), pp. 3368-3374 (1993).

Hanson, G.R., et al., "Role of the 5-HT$_2$ Receptor in the Methamphetamine-Induced Neurochemical Alterations," *J. of Pharm. and Experimental Therapeutics*, 270(1): 97-103 (1994).

Harris, J.G., et al., "Effects of nicotine on cognitive deficits in schizophrenia," *Neuropsychopharmacol*. 29: 1378-1385 (2004).

Harrison, P. J., "The neuropathology of schizophrenia. A critical review of the data and their interpretation," Brain 122( Pt 4): 593-624 (1999).

Harrist A, Beech RD, King SL, Zanardi A, Cleary MA, Caldarone BJ, Eisch A, Zoli M, Picciotto MR, Alteration of hippocampal cell proliferation in mice lacking the beta 2 subunit of the neuronal nicotinic acetylcholine receptor, Synapse 54: 200-6 (2004).

Hashimoto, K., et al., "a7 Nicotinic Receptor Agonists as Potential Therapeutic Drugs for Schizophrenia," Curr. Med. Chem.—Central Nervous System Agents, 5: 171-184 (2005).

Hashimoto, R., et al., "Impact of the DISC1 Ser704Cys polymorphism on risk for major depression, brain morphology and ERK signaling," Hum. Mol. Genet. 15(20): 3024-33 (2006).

Hauser TA, Kucinski A, Jordan KG, Gatto GG, Wersinger SR, Hesse RZ, Stachowiak EK, Stachowiak MK, Lippiello PM, Bencherif M. TC-5619: An alpha7 neuronal nicotinic receptor-selective agonist that ameliorates positive and negative symptoms and enhances cognitive function in animal models of schizophrenia. Biochem. Phamacol, Oct. 1, 2009; 78 (7), 803-12.

Hauser, T.A., et al., "P.3.b.005 TC-5619: an a 7 neuronal nicotinic receptor-selective agonist with the potential to treat schizophrenia," *Euro. Neuropsychopharm*. Elsevier Science Pub. BV, Amsterdam, NL, 16: Jan. 1, 2006 S394 XP005851134 ISSN: 0924-977X.

Heeschen, Christoper, et al., "A Novel Angiogenic Pathway Mediated by Non-Neuronal Nicotinic Acetylcholine Receptors," The Journal of Clinical Investigation, vol. 110, No. 4, pp. 527-536 (Aug. 2002).

Henderson, D., of al., "A Double-Blind, Placebo-Controlled Trial of Sibutramine for Olanzapine-Associated Weight Gain," *Am. J. Psychiatry*, 162(5): 954-962 (2005b).

Henderson, D., et al., "Glucose Metabolism in Patients With Schizophrenia Treated With Atypical Antipsychotic Agents," *Arch. Gen. Psychiatry*, 62: 19-28 (2005a).

Hietala, J. et al., "Depressive symptoms and presynaptic dopamine function in neuroleptic-naive schizophrenia," *Schizophr. Res*. 35(1): 41-50 (1999).

Hietala, J., et al., "Presynaptic dopamine function in striatum of neuroleptic-naive schizophrenic patients," *Lancet* 346 (8983): 1130-1131 (1995).

Holden, C., "Deconstructing Schizophrenia: Large-scale family studies and new drug probes focus on cognitive deficits that may lie at the heart of the disease," *Science* 299: 333-335 (2003).

Holladay, M. W. et al. J. Med. Chem., vol. 40, No. 26, pp. 4169-4194 (1997).

Horbinski, C., et al., "Bone morphogenetic protein-7 stimulates initial dendritic growth in sympathetic neurons through an intracellular fibroblast growth factor signaling pathway," *J. Neurochem*. 80(1): 54-63 (2002).

Hoyer, D. and Boddeke, H., *Trends Pharmacol. Sci*. 14(7): 270-5 (1993.

http://en.wikipedia.org/wiki/Attention_deficit_disorder, last accessed on Jul. 22, 2010.

http://schizophrenia.com/diag.php; last accessed on Nov. 9, 2009.

http://www.medicinenet.com/learning_disability/article.htm, last accessed on Jul. 22, 2010.

http://www.mentalhealth.org.uk/information/mental-health-a-z/dementia/, last accessed, Jul. 14, 2010.

Hu, Z., et al., "Differentiation of the midbrain dopaminergic pathways during mouse development," *J. Comp. Neurol*. 476(3: 301-11 (2004).

Hurst, R., et al., "A Novel Positive Allosteric Modulator of the α7 Neuronal Nicotinic Acdtylcholine Receptor: In Vitroand in Vivo Characterization," J. of Neuroscience, 25(17): 4396-4405 (2005).

Ikemoto, K., et al., "Human midbrain dopamine neurons express serotonin 2A receptor: an immunohistochemical demonstration," Brain Res. 853(2): 377-80 (2000).

International Search Report (PCT/US2004/005044, dated Nov. 3, 2004).

(56) References Cited

OTHER PUBLICATIONS

International Search Report (PCT/US2008/071872/ dated Dec. 3, 2008).
International Search Report, PCT/US99/19906, Jan. 13, 2000.
Isomaa, B. A., et al., "Major health hazard: the metabolic syndrome," *Life Sci.* 73: 2395-2411 (2003).
Jonakait, G. Miller, Tins, "Neural-immune interactions in sympathetic ganglia," vol. 16, No. 10, pp. 419-423 (1993).
Kaneko N, Okano H, Sawamoto K, Role of the cholinergic system in regulating survival of newborn neurons in the adult mouse dentate gyrus and olfactory bulb, *Genes Cells* 11: 1145-59 (2006).
Kasper, S., et al., "Dopamine-and Serotonin-Receptors in Schizophrenia: Results of Imaging-Studies and Implications . . ." *Eur. Arch. Psychiatry Clin. Neurosci.* 249(Suppl. 4): IV/ 83-IV/89 (1999).
Kastelein, J.J., et al., "The future of lipid-lowering therapy: the big picture," *Neth. J. Med.* 61: 35-39 (2003).
Kawashima, K. and Fujii, T., "Extraneuronal Cholinergic System in Lymphocytes," *Pharmacology & Therapeutics*, 86:29-48 (2000).
Kem,William R. "The brain a7 nicotinic receptor may be an important therapeutic target for the treatment of Alzheimer's disease: studies with DMXBA (GTS-21)," *Behav. Brain Res.*, 113: 169-181 (2000).
Kenner, K.A., et al., "Protein-tyrosine phosphatase 1B is a negative regulator of Insulin- and Insulin-like Growth Factor-I-stimulated signaling," *J. Biol. Chem.* 271: 19810-19816 (1996).
Kirito, K. et al., "Thrombopoietin regulates Bcl-xL gene expression through Stat5 and phosphatidylinositol 3-kinase activation pathways," *J: Biol. Chem.* 277: 8329-8337 (2002).
Kitagawa, H., et al., "Safety, pharmacokinetics, and effects on cognitive function of multiple doses of GTS-21 in healthy, male volunteers," *Neuropsychopharmacol.* 28: 542-551 (2003).
Klaman, L.D. et al., "Increased energy expenditure, decreased adiposity, and tissue-specific insulin sensitivity in Protein-tyrosine Phosphatase 1B-deficient mice," *Mol. Cell. Biol.*, 20: 5479-5489 (2000).
Klein, D., at al., "A Randomized, Double-Blind, Placebo-Controlled Trial of Metformin Treatment of Weight Gain Associated With Initiation of Atypical . . . ," *Am. J. Psychiatry*, 163(12): 2072-2079 (2006).
Klejbor, L., et al., "Fibroblast growth factor receptor signaling affects development and function of dopamine neurons—inhibition results in a schizophrenia-like syndrome in transgenic mice," *J. Neurochem.* 97(5): 1243-1258 (2006).
Koller, A.K. and P.M. Doraiswamy, "Olanzapine-Associated Diabetes Mellitus" *Pharmacotherapy*, 22(7): 841-852 (2002).
Kotani S, Yamauchi T, Teramoto T, Ogura H, Pharmacological evidence of cholinergic involvement in adult hippocampal neurogenesis in rats, *Neuroscience* 142: 505-14 (2006).
Kumari, V. and T. Sharma, "Effects of Typical and Atypical Antipsychotics on Prepulse Inhibition in Schizophrenia . . ." Psychopharmacology, 162: 97-101 (2002).
Kwon, J.S., et al., "Gamma frequency-range abnormalities to auditory stimulation in schizophrenia," *Arch. Gen. Psych.* 56: 1001-1005 (1999).
Lai, Albert, et al., Long-Term Nicotine Treatment Decreases Striatal a6* Nicotinic Acetylcholine Receptor Sites and Function in Mice, Mol. Pharmacol. 67(5): 1639-1647 (2005).
Laruelle, M., et al., "Single photon emission computerized tomography imaging of amphetamine-induced dopamine release in drug-free schizophrenic subjects," *Proc. Natl. Acad. Sci. U S A* 93(17): 9235-9240 (1996).
Lauder, J. M., "Neurotransmitters as growth regulatory signals: role of receptors and second messengers," *Trends Neurosci.* 16(6): 233-240 (1993).
Leiser, Steven C. et al., "A cog in cognition: How the α7 nicotinic acetylcholine receptor is geared towards improving cognitive deficits," Pharmacology & Therapeutics, 122: 302-311 (2009).
Lena, C., et al., "Role of Ca2+ ions in nicotinic facilitation of GABA release in mouse thalamus," *J. Neurosci.* 17: 576-585 (1997).

Leonard, S. and R. Freedman, "Genetics of Chromosome 15q13-q14 in Schizophrenia," *Biol. Psychiatry*, 60:115-122 (2006).
Leonard, S., et al., "Association of promoter variants in the alpha7 nicotinic acetylcholine receptor subunit gene with an inhibitory deficit found in schizophrenia," *Arch. Gen. Psych.* 59: 1085-1096 (2002).
Leonard, S., et al., "Nicotinic Receptor Function in Schizophrenia," *Schizophrenia Bulletin*, 22(3): 431-445 (1996).
Leonard, S., et al., "Smoking and Mental Illness," Pharm., Biochemistry and Behavoir, 70: 561-570 (2001).
Leonik, et al., "Quinuclidines as selective agonists for alpha-7 nicotinic acetylcholine receptors," Bio. Medic. Chem. Lett., 17(6): 1520-1522 (2007).
Levin, E.D., et al., "AR-R17779, an a7 nicotinic agonist, improves learning and memory in rats," Behav. Pharmacol., 10(6-7): 675-680 (1999).
Levin, E.D., et al., "Nicotine-haloperidol interactions and cognitive performance in schizophrenics," Neuropsychopharmacol. 15: 429-436 (1996).
Lewy Body-Like Pathology in Long-Term Embryonic Nigral Transplants in Parkinson's Disease, Nature Medicine 14, 504-506 (May 1, 2008)—including citation thereof in NeuroInvestment, Jan. 2009.
Li, P., "Cytochrome c and dATP-dependent formation of Apaf-1/ caspase-9 complex initiates an apoptotic protease cascade," Cell 91: 479-489 (1997).
Li, Y. et al., "Insulin-Like Growth Factor-1 Receptor Activation Inhibits Oxidized LDL-Induced Cytochrome C Release and Apoptosis via the Phosphatidylinositol 3 Kinase/Akt Signaling Pathway," Arterioscler. Thromb. Vasc. Biol., 23: 2178-2184 (2003).
Lippiello, P.M., K.G. Fernandes, "The Binding of L-[$_3$H]Nicotine to a Single Class of High Affinity Sites in Rat Brain Membranes," *Molecular Pharmacology*, 29(5): 448-454 (1986).
Liu, Q., et al., "Dissecting the signaling pathway of nicotine-mediated neuroprotection in a mouse Alzheimer disease model," *FASEB J* 21: 61-73 (2007).
Lou, Jinning, et al., Pathogenesis of Cerebral Malaria: Recent Experimental Data and Possible Applications for Humans, Clin. Micro. Rev., 14(4): 810-820 (2001).
Ludewig, K., et al., "Impaired sensorimotor gating in schizophrenia with deficit and with nondeficit syndrome," *Swiss Med. Wkly.* 132: 159-165 (2002).
Macor, et al., "The 5-HT$_3$ Antagonist Tropisetron (ICS 205-930) is a Potent and Selective a7 Nicotinic Receptor Partial Agonist," *Bioorg. Med. Chem. Lett.* 11: 319-321 (2001).
Madretsma, G.S., et al., "Nicotine Inhibits the in vitro Production of Interleukin 2 and Tumour Necrosis Factor-Alpha by Human Mononuclear Cells," Immunopharmacology, 35(1):47-51 (1996).
Madretsma, Stanley et al., "In-vivo effect of nicotine on cytokine production by human non-adherent mononuclear cells," European Journal of Gastroenterology & Hepatology, vol. 8, No. 10, pp. 1017-1020 (1996).
Malberg JE, Eisch AJ, Nestler EJ, Duman RS, Chronic antidepressant treatment increases neurogenesis in adult rat hippocampus, *J Neurosci* 20:9104-9110 (2000).
Mansvelder, H.D., et al., "Long-term potentiation of excitatory inputs to brain reward areas by nicotine," *Neuron.* 27: 349-357 (2000).
Marrero M, Lucas R, Salet C, Hauser TA, Mazarov A, Lippiello PM, Bencherif M. An Alpha7 Receptor-Selective Agonist Reduces Weight Gain and Metabolic Changes in a Mouse Model of Diabetes. J Pharmacol Exper Ther Fast Forward Sep. 28, 2009; e-pub.
Marrero, M.B., "The neuroprotective effect of 2-(3-pyridyl)-1-azabicyclo[3.2.2]nonane (TC-1698), a novel alpha7 ligand, is prevented through angiotensin II activation of a tyrosine phosphatase," *J. Pharmacol Exp Ther.* 309(1): 16-27 (2003).
Martin, L, et al., "Alpha-7 nicotinic receptor agonists: potential new candidates for the treatment of schizophrenia," *Psychopharmacol.* 174: 54-64 (2004).
Martin, P., et al., "Rodent Data and General hypothesis: Antipsychotic Action Exerted through 5-HT2A Receptor Antagonism is Dependent on Increased Serotonergic Tone," *J. Neuro. Transm.*, 105: 365-396 (1998).

(56) References Cited

OTHER PUBLICATIONS

Maskell, et. al., "Inhibition of human α7 nicotinic acetylcholine receptors by opn channel blockers of N-methyl-D-asparate receptors," British Journal of Pharmacology, 140(7): 1313-1319 (2003).
Mata, P., et al., "Benefits and risks of simvastatin in patients with familial hypercholesterolaemia," Drug Saf. 26: 769-786 (2003).
Matthys, Patrick, Ph.D., et al., "Cytokines and Cachexia," Nutrition, vol. 13, No. 9, pp. 763-770 (1997).
Mazarov, A., et al., "2-(Arylmethyl)-3-substituted quinuclidine as selective alpha7 nicotinic receptor ligands," Bio. Medic. Chem. Lett. 15(8): 2073-2077 (2005).
Mazurov, A., et at., Selective α7 Nicotinic Acetylcholine Receptor Ligands, Current Medical Chemistry, 13(13): 1567-1584 (2006).
McKay, D.M., et al., "Superantigen immune stimulation activates epithelial STAT-1 and PI 3-K: PI 3-K regulation of permeability," Am. J. Physiol. Gastrointest. Liver Physiol. 279: G1094-G1103 (2000).
Meissner, W.C., et al., "Priorities in Parkinson's Disease research," Nature Reviews, 10:377-393 (2011).
Meltzer, H. Y., et al., "Classification of typical and atypical antipsychotic drugs on the basis of dopamine D-1, D-2 and serotonin2 pKi values," J. Pharmacol. Exp. Ther. 251(1): 238-46 (1989).
Meske, V., et al., "Blockade of HMG-CoA reductase activity causes changes in microtubule-stabilizing protein tau via suppression of geranylgeranylpyrophosphate formation: implications for Alzheimer's disease," European Journal of Neuroscience 17: 93-102 (2003).
Meyer, A., et al., "Reduced prefrontal activity predicts exaggerated striatal dopaminergic function in schizophrenia," Nat. Neurosci. 5(3): 267-71 (2002).
Meyer, E., et al., "Effects of Anabaseine-Related analogs on Rat Brain Nicotinic Receptor Binding and on Avoidance Behaviors," Drug Development Research, 31: 127-134 (1994).
Meyer, Edwin M., et al., "3-[2,4-Dimethoxybenzylidene]anabaseine (DMXB) selectively activates rat a7 receptors and improves memory-related behaviors in a mecamylamine-sensitive manner," Brain Res., 768(1-2): 49-56 (1997).
Miao, F., et al., "Vagal modulation of spinal nicotine-induced inhibition of the inflammatory response mediated by descending antinociceptive controls," Neuropharmacology, 45: 605-611 (2003).
Millar, J. K., et al., "DISC1 and PDE4B are interacting genetic factors in schizophrenia that regulate cAMP signaling," Science 310(5751): 1187-91 (2005).
Moffett, J., et al., "Increased tyrosine phosphorylation and novel cis-acting element mediate activation of the fibroblast growth factor-2 (FGF-2) gene by nicotinic acetylcholine receptor. New mechanism for trans-synaptic regulation of cellular development and plasticity," Brain Res. Mol. Brain Res. 55: 293-305 (1998).
Mohapel P, Leanza G, Kokaia M, Lindvall O, Forebrain acetylcholine regulates adult hippocampal neurogenesis and learning, Neurobiol Aging 26: 939-46 (2005).
Moosmann, B., et al., "Selenoprotein synthesis and side-effects of statins" Lancet, 363: 892-894 (2004).
Mudo, G., et al., "Acute intermittent nicotine treatment induces fibroblast growth factor-2 in the subventricular zone of the adult rat brain and enhances neuronal precursor cell proliferation," Neurosci. 145: 470-483 (2007a).
Mudo, G., et al., "Nicotinic receptor agonists as neuroprotective / neurotrophic drugs," Prog. Mol. Mechanisms 114: 135-147 (2007b).
Mullen, George, et al., "(-)-Spiro[1-azabicyclo[2.2.2]octane-3,5'-oxazolidin-T-one], a Conformationally Restricted Analogue of Acetylcholine, Is a Highly Selective Full Agonist at the a7 Nicotinic, Acetylcholine Receptor," J. Med. Chem., 43(22): 4045-4050 (2000).
Murphy, P.C., et al., "Brain-stem modulation of the response properties of cells in the cat's perigeniculate nucleus," Vis. Neurosci. 11: 781-791 (1994).
Myers, M.P., et al., "TYK2 and JAK2 are substrates of Protein-tyrosine Phosphatase 1B," J. Biol. Chem., 276: 47771-47774 (2001).

Nakata, M., et al., "Effects of Statins on the Adipocyte Maturation and Expression of Glucose Transporter 4; Implications in Glycemic Control," Diabetologia 49: 1881-1892 (2006).
National Cholesterol Education Program Adult Treatment Panel III (2001).
National Diabetes Federation, the World Health Organization, the European Group for the Study of Insulin Resistance (1999).
Newhouse, P.A., et al., "Effects of nicotinic stimulation on cognitive performance," Curr. Opin. Pharmacol. 4:36-46 2004.
Newman, M.B. et al., "Nicotine's oxidative and antioxidant properties in CNS," Life Sciences 71: 2807-2820 (2002).
Nilsson, L.K., et al., "Subchronic treatment with kynurenine and probenecid: effects on prepulse inhibition and firing of midbrain dopamine neurons," J. Neural. Trans. 113: 557-571, 2006.
Nizri E, Wirguin I, Brenner T, The role of cholinergic balance perturbation in neurological diseases, Drug News Perspect. 20: 421-9 (2007).
O'Neill et al., The Role of Neuronal Nicotinic Acetylcholine Receptors in Acute and Chronic Neurodegeneration, Curr Drug Targets CNS Neurol Disord., Aug. 2000, 1(4), 399-411.
O'Neill, H.C., et al., "DMXB, an alpha7 nicotinic agonist, normalizes auditory gating in isolation-reared rats," Psychopharmacol. 169: 332-339 (2003).
Ohmura, C.,et al., "Acute Onset and Worsening of Diabetes Concurrent with Administration of Statins," Endocrine Journal, 52(3): 369-372 (2005).
Ohtani, N., et al., "Dopamine modulates cell cycle in the lateral ganglionic eminence," J. Neurosci. 23(7): 2840-2850 (2003).
Olesen, P.H. et al., Bioorganic & Medicinal Chemistry Letters, vol. 7, No. 15, pp. 1963-1968 (1997).
Olincy, A., et al., "Proof-of-Concept Trial of an α7 Nicotinic Agonist in Schizophrenia," Arch. Gen. Psychiatry, 63: 630-638 (2006).
Ovalle, S., et al., "Fibroblast growth factor-2 is selectively modulated in the rat brain by E-5842, a preferential sigma-1 receptor ligand and putative atypical antipsychotic," Eur. J. Neurosci. 13(5): 909-15 (2001).
Papke, R.L., et al., "Comparative pharmacology of rat and human alpha7 nAChR conducted with net charge analysis," Br. J. Pharmacol. 137: 49-61 (2002).
Parker, Steven L., et al., Up-Regulation of Brain Nicotinic Acetylcholine Receptors in the Rat during Long-Term Self-Admi ist:ration of Nicotine: Disproportionate Increase of the a6 Subunit, Mol. Pharmacol. 65(3): 611-622 (2004).
Pavlov, V.A., et al., "The Cholinergic Anti-Inflammatory Pathway: A Missing Link in Neuroimmunomodulation," Molecular Medicine, 9(5-8): 125-134 (2003).
Peacock, Mark E., et al., "The Effect of Nicotine on Reproduction and Attachment of Human Gingival Fibroblasts in Vitro," J. Periodontal, vol. 64, No. 7, pp. 658-665 (1993).
Perera TD, Park S, Nemirovskaya Y, Cognitive role of neurogenesis in depression and antidepressant treatment, Neuroscientist 14: 326-38 (2008).
Petronis, A., "The origin of schizophrenia: genetic thesis, epigenetic antithesis, and resolving synthesis," Biol. Psychiatry 55(10): 965-70 (2004); S A 93, (17): 9235-40 (1996).
Picciotto et al., Neuroprotection via nAChRs, Front BioSci., Jan. 1, 2008, 492-504.
Picciotto MR, Brunzell DH, Caldarone BJ, Effect of nicotine and nicotinic receptors on anxiety and depression, Neuroreport 13: 1097-1106 (2002).
Pichat, P., et al., "SSR180711A, A Novel Selective α7-Nicotinic Receptor Partial Agonist. III. Effects in Models . . . Symptoms of Schizophrenia," Soc. Neurosci. Abstr. 34: 583.3 (2004).
Pickar, J.G., et al., "Increased Na+ -K+ pump number and decreased pump activity in soleus muscles in SHR," Am. J. Physiol., 267: C836-C844 (1994).
Pullan, Robert D. et al., "Transdermal Nicotine for Active Ulcerative Colitis," The New England Journal of Medicine, vol. 330, No. 12, pp. 811-815 (1994).
Pullan, Rupert D., "Colonic mucus, smoking and ulcerative colitis," Ann R. Coll. Surg Engl., 78, pp. 85-91 (1996).

(56) References Cited

OTHER PUBLICATIONS

Quarta, D., et al., "Drug discrimination and neurochemical studies in alpha7 null mutant mice: tests for the role of nicotinic alpha7 receptors in dopamine release," *Psychopharmacol*. Aug. 30 [Epub ahead of print] (2008).
Quik et al., Nicotine Neuroprotection Against Nigrostriatal Damage, Trends Pharamcol Sci., May 2007, 28(5), 229-35.
Quik, M., et al., "Localization of nicotinic receptor subunit mRNAs in monkey brain by in situ hybridization," J. Comp. Neurol. 425: 58-69 (2000).
Ravikumar et al. Molecular Brain Research (2004), 124(2), 188-198).
Rimon, R. et al., "The Content of 5-Hydroxyindoleacetic Acid and Homovanillic Acid in the Cerebrospinal Fluid of Patinets With Acute Schizophrenia," J. of Psychosomatic Research, 15: 375-378 (1971).
Roensch, J., et al., "Effects of statins on alpha7 nicotinic receptor, cholinesterase and alpha-form of secreted amyloid precursor peptide in SH-SY5Y cells," *Neurochemistry International*, 50(6): 800-806 (2007).
Romanovsky, A.A., et al., "The Vagus Nerve in the Thermoregulatory Response to Systemic Inflammation," American Journal of Physiology, 273(1):R407-413 (1997).
Ross, R. G., et al., "Anticipatory Saccades During Smooth Pursuit Eye Movements and Familial Transmission of Schizophrenia," *Biol. Psychiatry*, 44: 690-697 (1998).
Sandborn, W.J. et al., "Nicotine tartrate liquid enemas for mildly to moderately active left-sided ulcerative colitis unresponsive to first-line therapy: a pilot study," Ailment Pharmacol. Ther., 11, pp. 663-671 (1997).
Sandborn, W.J., et al., "Transdermal Nicotine for Mildly to Moderately Active Ulcerative Colitis," Annals of Internal Medicine, 126(5):364-371 (1997).
Santarelli L, Saxe M, Gross C, Surget A, Battaglia F, Dulawa S, et al, Requirement of hippocampal neurogenesis for the behavioral effects of antidepressants, Science 301: 805-809 (2003).
Sartor, R. Balfour M.D., "Pathogenesis and Immune Mechanisms of Chronic Inflammatory Bowel Diseases," The American Journal of Gastroenterology, vol. 92, No. 12, pp. 5S-11S (1997).
Sasaki, J., et al., "Statins: Beneficial or Adverse for Glucose Metabolism," Journal of Atherosclerosis and Thrombosis 13(1): 123-129 (2006).
Sato, E., et al., "Acetylcholine Stimulates Alveolar Macrophages to Release Inflammatory Cell Chemotactic Activity," Am. J. Physiol., 274:L970-79 (1998).
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, 266:17-20 (1999).
Scheinman, R.I., et al., "Role of Transcriptional Activation of I-kappaB-aleph in Mediation of Immunosuppression by Glucocorticoids," Science, 270:283-286 (1995).
Schimmel, J. J., et al., "4.5 kb of the rat tyrosine hydroxylase 5' flanking sequence directs tissue specific expression during development and contains consensus sites for multiple transcription factors," Brain Res. Mol. Brain Res. 74(12): 1-14 (1999).
Schmidt, C.J., "The Role of 5-HT2A Receptors in Antipsychotic Activity," Life Sciences 56:(25) 2209-2222 (1995)—(SPEC indicates 93, yet article is 1995).
Schmitt, J., "Exploring the Nature of Molecular Recognition in Nicotinic Acetylcholine Receptors," Curr. Med. Chem., 7(8): 749-800 (Aug. 2000).
Schmitz, G. et al., "Pharmacogenomics of cholesterol-lowering therapy," Vascular Pharmacology, 44(2): 75-89 (2006).
Schreiber, R., et al., "Effects of alpha 4/beta 2- and alpha 7-nicotine acetylcholine receptor agonists on prepulse inhibition of the acoustic startle response in rats and mice," Psychopharmacol. 159: 248-257 (2002).
Sernyak, M.J., et al., "Association of Diabetes Mellitus with Use of Atypical Neuroleptics in the Treatment of Schizophrenia," *AM. J. Psychiatry* 159: 561-566 (2002).

Shankaran M, King C, Lee J, Busch R, Wolff M, Hellerstein MK, Discovery of novel hippocampal neurogenic agents by using an in vivo stable isotope labeling technique, *J Pharmacol Exp Ther* 319:1172-1182 (2006).
Shankaran M, Marino ME, Busch R, Keim C, King C, Lee J, Killion S, Awada M, Hellerstein MK, Measurement of brain microglial proliferation rates in vivo in response to neuroinflammatory stimuli: Application to drug discovery, *J Neurosci Res* 85: 2374-84 (2007).
Sharma, R. P., et al., "Schizophrenia, epigenetics and ligand-activated nuclear receptors: a framework for chromatin therapeutics," *Schizophr. Res.* 72(2-3): 79-90 (2005).
Sharp, F.R., et al, "Psychosis: pathological activation of limbic thalamocortical circuits by psychomimetics and schizophrenia?" *Trends Neurosci.* 24: 330-334 (2001).
Shaw, S., et al., "Kinase 2, an early target of α7 nicotinic acetylcholine receptor-mediated neuroprotection against Aβ-(1-42) amyloid," *J. Biol. Chem.*, 277: 44920-44924 (2002).
Sher, M.E., et al., "The Influence of Cigarette Smoking on Cytokine Levels in Patients with Inflammatory Bowel Disease," Inflammatory Bowel Diseases, 5(2):73-78 (1999).
Shingo AS, Kito S, Effects of nicotine on neurogenesis and plasticity of hippocampal neurons, *J Neural Transm* 112: 1475-8 (2005).
Shytle RD, Silver AA, Lukas RJ, Newman MB, Sheehan DV, Sanberg PR, Nicotinic acetylcholine receptors as targets for antidepressants, *Mol Psychiatry* 7: 525-535 (2002).
Silverstein, Marc D., M.D. et al., "Cigarette Smoking and Ulcerative Colitis: A Case-Control Study," Mayo Clinic Proc., vol. 69 pp. 425-429 (1994).
Simosky, et al., "Intragastric DMXB-A, an alpha7 nicotinic agonist, improves deficient sensory inhibition in DBA/2 mice," *Biol. Psychiatry*, 50: 493-500 (2001).
Simosky, J.K., et al., "Clozapine improves deficient inhibitory auditory processing in DBA/2 mice, via a nicotinic cholinergic mechanism," Psychopharmacol. 165: 386-396 (2003).
Singhal, S.K., et al., "Antipsychotic clozapine inhibits the function of alpha7-nicotinic acetylcholine receptors," Neuropharmacol. 52: 387-394 (2007).
Snyder, S. H., "The dopamine hypothesis of schizophrenia: focus on the dopamine receptor," Am. J. Psychiatry 133(2): 197-202 (1976).
Sotelo et al. Annals of Internal Medicine (2006), 144(5), 337-343.
Stachowiak, E. K., et al., "cAMP-induced differentiation of human neuronal progenitor cells is mediated by nuclear fibroblast growth factor receptor-1 (FGFR1)," J. Neurochem.84(6): 1296-312 (2003).
Stachowiak, M. K., et al., "Apparent sprouting of striatal serotonergic terminals after dopamine-depleting brain lesions in neonatal rats," Brain Res. 291(1): 164-7 (1984).
Stachowiak, M. K., et al., "Integrative Nuclear Signaling in Cell Development—A Role for FGF Receptor-1," DNA Cell Biol. 26(12): 811-26 (2007).
Stahl, S.M., "Antipsychotic agents. In: Essential Pharmacology: Neuroscientific Basis and Practical Applications," *Cambridge University Press*, New York, pp. 401-458 (2002).
Steinlein, O., "New Functions for Nicotine Acetylcholine Receptors?," Behavioural Brain Res., 95:31-35 (1998).
Sternberg, E.M. (Series Editor), "Neural-immune Interactions in Health and Disease," the Journal of Clinical Investigation, 100(11):2641-2647 (1997).
Stevens, K.E., et al., "Selective a-7-nicotinic agonists normalize inhibition of auditory response in DBA mice," *Psychopharm.* 136: 320-327 (1998).
Suzuki T, Hide I, Matsubara A, Hama C, Harada K, Miyano K, Andrä M, Matsubayashi H, Sakai N, Kohsaka S, Inoue K, Nakata Y, Microglial alpha7 nicotinic acetylcholine receptors drive a phospholipase C/IP3 pathway and modulate the cell activation toward a neuroprotective role *J Neurosci Res* 83:1461-70 (2006).
Swerdlow, N. R., et al., "Assessing the validity of an animal model of deficient sensorimotor gating in schizophrenic patients," *Arch. Gen. Psychiatry* 51(2): 139-54 (1994).
Swerdlow, N. R., et al., "Using an animal model of deficient sensorimotor gating to study the pathophysiology and new treatments of schizophrenia," *Schizophr. Bull.* 24(2): 285301 (1998).

(56) References Cited

OTHER PUBLICATIONS

Sykes, A.P., et al., "An Investigation into the Effect and Mechanisms of Action of Nicotine in Inflammatory Bowel Disease," Inflamm. Res., 49:311-319 (2000).
Sykiotis, G.P. & a.G. Papavassiliou, "Serine phosphorylation of Insulin Receptor Substrate-1: A novel target for the reversal of insulin resistanc," *Mol. Endocrinol.* 15: 1864-1869 (2001).
Syymanski, S. et al., "The dopamine-serotonin relationship in clozapine response," *Psychopharmacology* 112: S85-S89 (1993).
Takano, T., et al., "Influence of Statins on Glucose tolerance in Patients with Type II Diabetes Mellitus," *Journal of Atherosclerosis and Thrombosis* 13: 95-100 (2006).
Tcheremissine, et. al., "Pharmacotherapy of adult attention deficit/ hyperactivity disorder: review of evidence-based practices and future directions," Expert Opin. Pharmacotherapy, 1299-1310 (2008) 9(8).
Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670.
Tietje, K.R., et al., "Preclinical characterization of A-582941: a novel alpha7 neuronal nicotinic receptor agonist with broad spectrum cognition-enhancing properties," CNS Neurosci. Ther. 14: 65-82 (2008).
Timmermann, D.B., et al., "An allosteric modulator of the alpha7 nicotinic acetylcholine receptor possessing cognition-enhancing properties in vivo," J. Pharmacol. Exp. Ther. 323: 294-307 (2007).
Toler et al. Neurosurg Focus. Dec. 15, 2006;21(6):E10.).
Toyabe, S., et al., "Identification of Nicotinic Acetylcholine Receptors on Lymphocytes in the Periphery as well as Thymus in Mice," Immunology, 92:201-205 (1997).
Tracey, Kevin J., "The Inflammatory Reflex," Nature, vol. 420, pp. 853-859 (Dec. 2002).
Tracey, Kevin J., et al., "Mind over immunity, "*FASEB J.*, 15(9): 1575-1576 (2001).
Tumkosit, Prem, et al., 113 Subunits Promote Expression and Nicotine-Induced Up-Regulation of Human Nicotinic 06* Nicctinic Acetylcholine Receptors Expressed in Transfected Cell Lines, Mol. Pharmacol. 70(4): 1358-1368 (2006).
U.S. Appl. No. 60/971,654.
Uysal, K.T., et al., "Protection from obesity-induced insulin resistance in mice lacking TNF-α function," *Nature* 389: 610-614 (1997).
Van Dijk, A.P.M., et al., "Transdermal Nicotine Inhibits Interleukin 2 Synthesis by Mononuclear Cells Dervied from Healthy Volunteers," European Journal of Clinical Investigation, 28:664-671 (1998).
Van Dijk, Jeanette P.M. et al., "Nicotine inhibits cytokine synthesis by mouse colonic mucosa." European Journal of Pharmacology, 278, R11-R12 (1995).
Van Kampen, M., et al., "AR-R 17779 Improves Social Recognition in Rats by Activation of Nicotinic α7 Receptors," Psychopharmacology, 172: 375-383 (2004).
Visanji, N.P., et al., Chronic pre-treatment with nicotine enhances nicotine-evoked striatal dopamine release and a6 and a3 nicotinic acetylcholine receptor subunit mRNA in the substantia nigra pars compacta of the rat, Neur pharmacology 50: 36-46 (2006).
Vollenweider, M., et al. "Clozapine Enhances Prepulse Inhibition in Healthy Humans with Low But Not with High Prepulse Inhibition Levels," Biol. Psychiatry, 60: 597-603 (2006).
Wadenberg, M., et al., "Antagonism at 5-HT2A Receptors Potentiates the Effect of Haloperidol in a Conditioned Avoidance Response Task in Rats," Pharm., Bio., and Behavoir, 68: 363-370 (2001).
Waldo, M.C., et al., "Auditory sensory gating, hippocampal volume, and catecholamine metabolism in schizophrenics and their siblings," Schizophrenia. Res. 12: 93-106 (1994).
Walker, E., et al., "Schizophrenia: Etiollgy and Course" Annu. Rev. Psychol., 55:401-30 (2004).
Wallace, John L., et al., "Inflammatory Mediators in Gastrointestinal Defense and Injury," Proc. Soc. Exp. Biol. Med., vol. 214, pp. 192-203 (1997).
Wang N, Orr-Urtreger A, Korczyn AD, The role of neuronal nicotinic acetylcholine receptor subunits in autonomic ganglia: lessons from knockout mice, Prog Neurobiol. 68: 341-60 (2002).

Wang, Hong, et al, "Nicotinic Acetylcholine Receptor α7 subunit is an Essential Regulator of Inflammation," Nature, advance online publication, Dec. 22, 2002, pp. 1-4 (Dec. 2002).
Watkins, L.R. and Maier, S.F., "Implications of Immune-to-Brain Communication for Sickness and Pain," PNAS 96(14):7710-7713 (1999).
Watkins, L.R. et al., "Blockade of Interleukin-1 Induced Hyperthermia by Subdiaphragmatic Vagotomy:Evidence for Vagal Mediation of Immune-Brain Communication," Neuroscience Letters, 183:27-37 (1995).
Whaley, K., et al., "C2 Synthesis by Human monocytes is Modulated by a Nicotinic Cholinergic receptor," *Nature* 293: 580-582 (1981).
Wong, A. H., et al., "Identification of candidate genes for psychosis in rat models, and possible association between schizophrenia and the 14-3-3eta gene," *Mol. Psychiatry* 8(2): 156-66 (2003).
Wong, A.H., and H. Tol, "Schizophrenia: From Phenomenology to Neurobiology," *Neuroscience and Biobehavioral Reviews*, 27: 269-306 (2003).
Woodruff-Pak, D., et al., "Nicotinic Cholinergic System Involvement in Eyeblink Classical Conditioning in Rabbits," *Behavioral Neuroscience*, 108(3): 486-493 (1994).
Xiu, J., et al., "Influence of cholesterol and lovastatin on alpha-form of secreted amyloid precursor protein and expression of alpha? nicotinic receptor on astrocytes," *Neurochemistry International* 49: 459-465 (2006).
Yamashita, H. and S. Nakamura, "Nicotine rescues PC12 cells from death induced by nerve growth factor deprivation," *Neurosci. Lett.*, 213(2): 145-147 (1996).
Yang, Y. K., et al., "Associated alterations of striatal dopamine D2/D3 receptor and transporter binding in drug naive patients with schizophrenia: a dual-isotope SPECT study," *Am. J. Psychiatry* 161(8): 1496-1498 (2004).
Yanina et al., Khim.-Karm, vol. 21(7), pp. 808-811 (1987).
Young, Jared W. et al., "Nicotine Improves Sustained Attention in Mice: Evidence for Involvement of the α7 Nicotinic Acetylcholine Receptor," Neuropsychopharmacology, 29: 891-900 (2004).
Zijlstra F. J. et al., "Effect of nicotine on rectal mucus and mucosal eicosanoids, " Gut, 35, pp. 247-251 (1994).
Zipp F, Aktas O, The brain as a target of inflammation: common pathways link inflammatory and neurodegenerative diseases, *Trends Neurosci* 29: 518-27 (2006).
Arneric, S., et al., "Cholinergic channel modulators as a novel therapeutic strategy for Alzheimer's disease," *Exp. Opin. Invest. Drugs* 5(1): 79-100 (1996).
Arneric, S., et al., "Preclinical Pharmacology of ABT-418: A Prototypical Cholinergic Channel Activator for the Potential Treatment of Alzheimer's Disease," *CNS Drug Rev.* 1(1):1-26 1995.
Bannon, et al., "Broad-Spectrum, Non-Opioid Analgesic Activity by Selective Modulation of Neuronal Nicotinic Acetylcholine Receptors," *Science* 279: 77-80 (1998).
Bencherif, M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosci.*, 2(1): 52-65 (1991).
Bencherif, M., and J. D. Schmitt, "Targeting Neuronal Nicotinic Receptors: a Path to New Therapies," *Current Drug Targets* 1(4): 349-357 (2002).
Bencherif, M., and R.J. Lukas, "Ligand Binding and Functional Characterization of Muscarinic Acetylcholine Receptors on the TE671/RD Human Cell Line," *J. Pharmacol. Exp. Ther.* 257(3): 946-953 (1991).
Breining, S. et al., "Neuronal Nicotinic Acetylcholine Receptor Modulators: Recent Advances and Therapeutic Potential," *Annul Reports in Medicinal Chemistry*, 40: 3-16 (2005).
Chaplan, S. R., et al., "Quantitative assessment of tactile allodynia in the rat paw," *J. Neurosci. Methods* 53: 55-63 (1994).
Coderre T.J., et al., "Central nervous system plasticity in the tonic pain response to subcutaneous formalin injection, " *Brain Res.* 535:155-158 (1990).
Coe, J., et al. "3,5-Bicyclic Aryl Piperidines : A Novel Class of α4β2 Neuronal Nicotinic Receptor Partial Agonists for Smoking Cessation," *Bioorganic& Medicinal Chemistry Letters* : 15(22) : 4889-4897 (2005).

(56) References Cited

OTHER PUBLICATIONS

Damaj, M., et al., "Enantioselective Effects of Hydroxy Metabolites of Bupropion on Behavior and on Function of Monoamine Transporters and Nicotinic Receptors," *Mol. Pharmacol.*, 66(3): 675-682 (2004).
Dubuisson, D. and Stephen G. Dennis, "The formalin test: A quantitative study of the analgesic effects of morphine, meperidine, and brain stem stimulation in rats and cats," *Pain* 4: 161-174 (1977).
Dwoskin, et al., "Recent developments in neuronal nicotinic acetylcholine receptor antagonists," *Exp. Opin. Ther. Patents* 10(10): 1561-1581 (2000).
Dwoskin, L.P. and P.A. Crooks, "A Novel Mechanism of Action and Potential Use for Lobeline As a Treatment for Psychostimulant Abuse," *Biochemical Pharmacology*, 63: 89-98 (2002).
Graham, A.J., et al., human Brain Nicotinic Receptors, their Distribution and Participation in Neuropsychiatric Disorders, *Current Drug Targets: CNS Neuron. Disord.*, 1: 387-397 (2002).
Halaas et al., "Weight-Reducing Effects of the Plasma Protein Encoded by the obese Gene," *Science*, 269: 553-546 (1995).
Namelmann E., et al., "Noninvasive measurement of airway responsiveness in allergic mice using barometric plethysmography," *Am J Respir Crit Care Med.*,156: 766-775 (1997).
Hogg, R.C. and D. Bertrand, "Nicotinic Acetylcholine Receptors as Drug Targets," *Current Drug Targets: CNS Neurol. Disord.*, 3: 123-130 (2004).
Holladay, et al., "Neuronal Nicotinic Acetylcholine Receptors as Targets for Drug Discovery," *J. Med. Chem.*, 40(26): 4169-4194 (1997).
Jain, K. K. J. "Modulators of Nicotinic Acetylcholine Receptors as Analgesics," *Current Opinion in Investigational Drugs*, 5(1): 76-81 (2004).
Jonnala, R.R. and J. J. Buccafusco, "Relationship Between the Increased Cell Surface $\alpha 7$ Nicotinic Receptor Expression and Neuroprotection Induced by Several Nicotinic Receptor Agonists," *Journal of Neuroscience Research*, 66: 565-572 (2001).
Kiso, Y. and H. Yajima, "Amide Formation, Deprotection, and Disulfide Formation in Peptide Synthesis," *Peptides*, 39-91 Academic Press, San Diego (1995).
Lavand'homme, P., and J.C. Eisenach, "Sex Differences in Cholinergic Analgesia II: Differing Mechanisms in Two Models of Allodynia," *Anesthesiology* 91(5): 1455-1461 (1999).
LeBars D., et al., "Animal Models of Nociception," *Pharmacological Reviews*, 53(4): 597-652 (2001).
Lee, G.H., et al., "Abnormal splicing of the Isptin receptor in diabetic mice," *Letters to Nature*, 632-635 (1996).
Levin, E.D., and A.H. Rezvani, "Nicotinic Treatment for Cognitive Dysfunction," *Current Drug Targets: CNS and Neurological Disorders* 1(4): 423-431 (2002).
Li, M.D., et al., "Nicotine, Body Weight and Potential Implications in the Treatment of Obesity," *Current Topics in Medicinal Chemistry*, 3:899-919 (2003).
Lippiello, P.M., et al., "RJR-2403: A Nicotinic Agonist with CNS Selectivity II. In Vivo Characterization," *J. P. E. T.* 279(3): 1422-1429 (1996).
Lowry, et al., "Protein Measurement with the Folin Phenol Reagent," *J. Biol. Chem.*, 193: 265-275 (1951).
Lukas, R.J., "Pharmacological Distinctions between Functional Nicotinic Acetylcholine Receptors on the PC12 Rat Pheochromocytoma and the TE671 Human Medulloblastoma," *J. Pharmacol. Exp. Ther.* 251(1): 175-182 (1989).
Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.* 175(1): 212-218 (1988).
Luther, et al., "A Muscle Acetylcholine Receptor is Expressed in the Human Cerebellar Medulloblastoma Cell Line TE671," *J. Neurosci.* 9(3): 1082-1096 (1989).
Malmberg A.B. and A.W. Bannon, "Models of nociception: hotplate, tail-flick, and formalin tests in rodents," *Current Protocols in Neuroscience*, Unit 8.9 (2002).
McEvoy, J. and T. Allen, "The Importance of Nicotinic Acetylcholine Receptors in Schizophrenia, Bipolar Disorder and Tourette's Syndrome," *Current Drug Targets: CNS Neurol. Disord.*, 1: 433-442 (2002).
Miao, F, et al., "Central Terminals of Nociceptors and Targets for Nicotine Suppression of Inflammation," *Neuroscience*, 123: 777-784 (2004).
Oswald, R.E., of al., "Characterization of nicotinic acetylcholine receptor channels of the TE671 human medulloblastoma clonal line," *Neurosci. Lett.* 96: 207-212 (1989).
Ripoll, N. et al., "Nicotinic Receptors and Schizophrenia," *Current Medical Research and Opinions*, 20(7): 1057-1074 (2004).
Sacco, K., et al., "Nicotinic Receptor Mechanisms and Cognition in Normal States and Neuropsychiatric Disorders," *J. Psychopharamacol.*,18(4): 457-474 (2004).
Schaible H.G. and B.D. Grubb, "Afferent and spinal mechanisms of joint pain," *Pain* 55: 5-54 (1993).
Schmader K.E., "Epidemiology and impact on quality of life of postherpetic neuralgia and painful diabetic neuropathy," *Clinical Journal of Pain* 18: 350-354 (2002).
Shytle, R., et al., "Neuronal Nicotinic Receptor Inhibition for Treating Mood Disorders: Preliminary Controlled Evidence With Mecamylamine," *Depression and Anxiety*, 16: 89-92 (2002).
Sommer, C., "Painful neuropathies," *Curr. Opin. Neurol.* 16: 623-628 (2003).
Stratton, et al., "Characterization of the human cell line TE671," *Carcinogenesis* 10(5): 899-905 (1989).
Suto et al., Neuronal Nicotinic Acetylcholine Receptors as Drug Targets, Expert Opin. Ther. Targets, 8(2): 61-64 (2004).
Takada et al., Nicotinic Acetylcholine Receptor-Mediated Neuroprotection by Nonzepezil Against Glutamate Neurotoxicity in Rat Cortical Neurons, J. Pharmacol. Exp. Ther., 306(2) 772-777 (2003).
Tjølsen, A. and K. Hole., Animal Models of Analgesia, In: Handbook of Experimental Pharmacology vol. 30: The Pharmacology of Pain (Eds. A Dickenson and J.M. Besson), Springer Verlag, New York, pp. 1-20 (1997).
Villemagne, et al., "Nicotine and Related Compounds as PET and SPECT Ligands," *Neuronal Nicotinic Receptors Pharmacology and Therapeutic Opportunities* 235-250 (1999).
Vincler, M., "Neuronal Nicotinic Receptors as Targets for Novel Analgesics," *Expert Opin. Invest. Drugs*, 14(10): 1191-1198 (2005).
Walker, K.M., et al., "The VR1 antagonist capsazepine reverses mechanical hyperalgesia in models of inflammatory and neuropathic pain," *JPET* 304: 56-62 (2003).
Whiting, P. J., et al., "Functional acetylcholine receptor in PC12 cells reacts with a monoclonal antibody to brain nicotinic receptors," *Nature* 327: 515-518 (1987).
Whiting, P.J., et al., "Expression of nicotinic acetylcholine receptor subtypes in brain and retina," *Brain Res Mol Brain Res.* 10(1): 61-70 (1991).
Williams, et al., "Neuronal Nicotinic Acetylcholine Receptors," Drug News Perspec. 7(4): 205- 223 (1994).
Young, J. et al., "Mecamylamine: New Therapeutic Uses and Toxicity/Risk Profile," *Clinical Therapeutics*, 23(4): 532-565 (2001).

\* cited by examiner

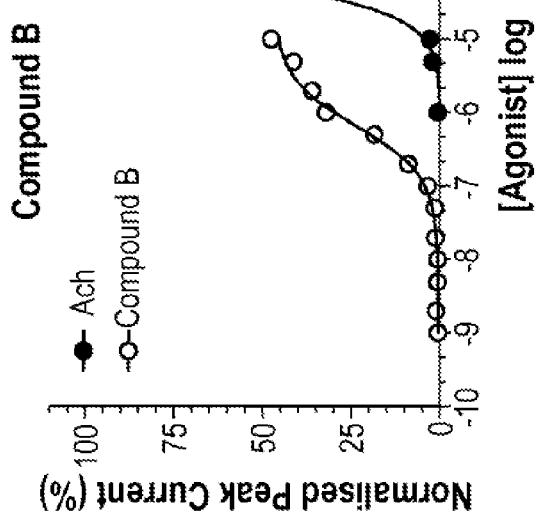
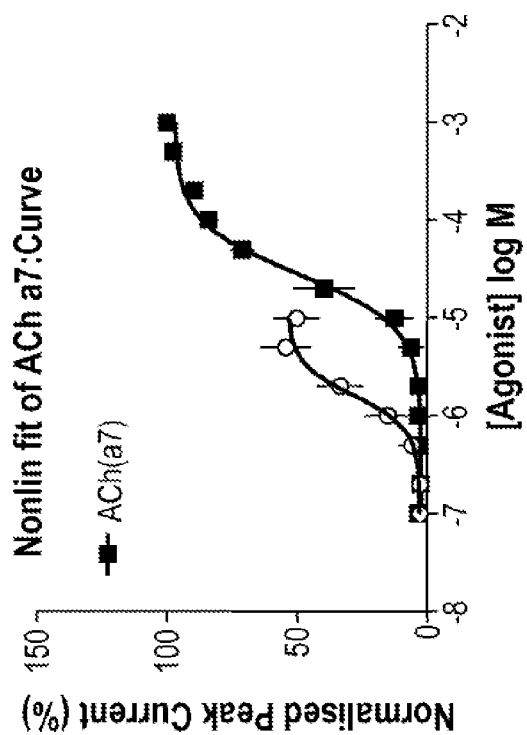
Fig. 5

Compound A

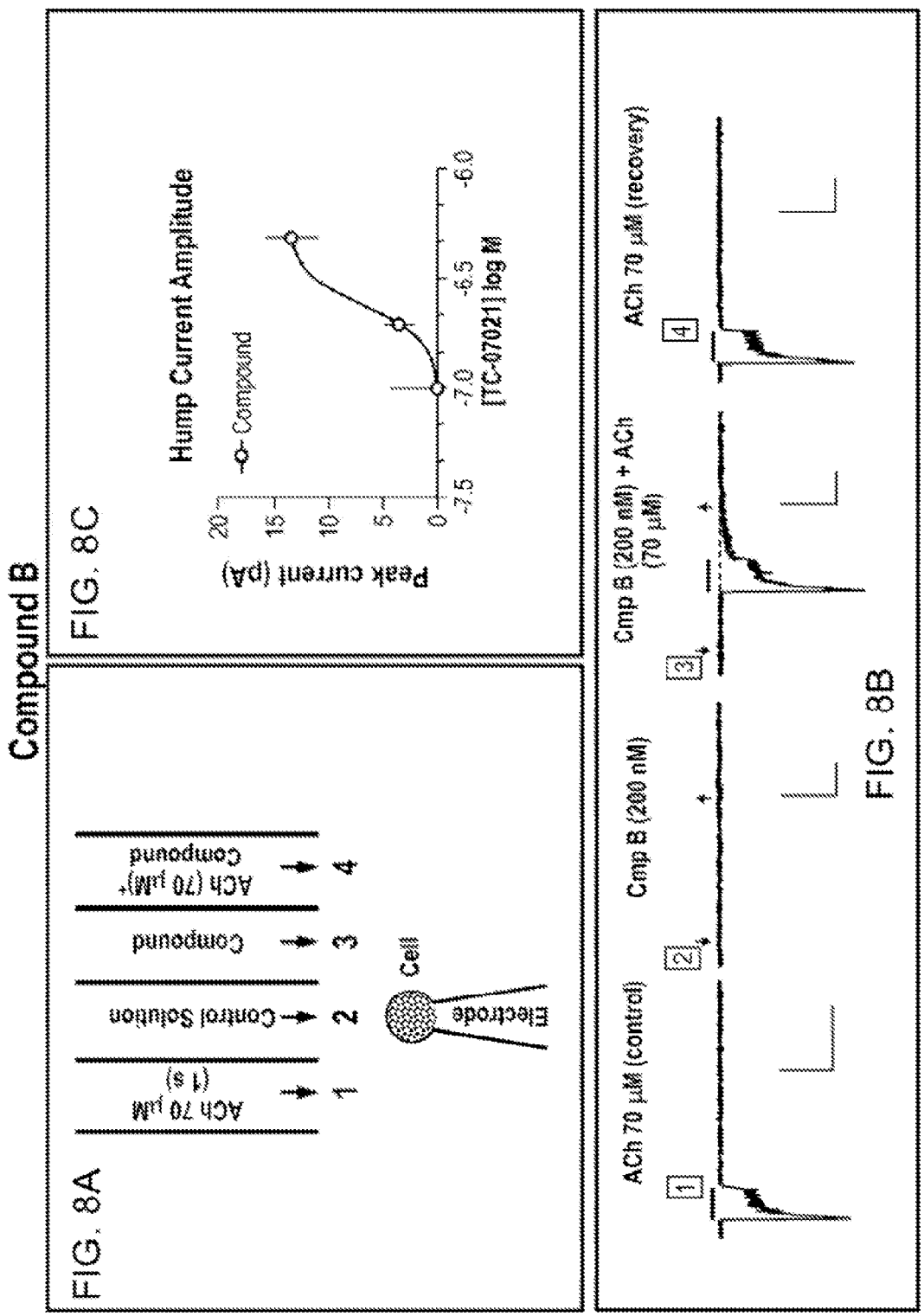

Crystal Structure of Mono-HCl Salt

- P<0.01 compared with obese mice administered vehicle ("db").

- Test Article = (2S,3R)-N-2-((3-pyridinyl)methyl)-1-azabicyclo[2.2.2]oct-3-yl)-3,5-difluorobenzamide

* P<0.01 compared with obese mice administered vehicle ("db").

*P<0.01 compared with obese mice administered vehicle ("db").

*P<0.01 compared with obese mice administered vehicle ("db").

*P<0.01 compared with obese mice administered vehicle ("db").

*P<0.01 compared with obese mice administered vehicle ("db").

PREPARATION AND THERAPEUTIC APPLICATIONS OF (2S,3R)-N-2-((3-PYRIDINYL)METHYL)-1-AZABICYCLO-[2.2.2]OCT-3-YL)-3,5-DIFLUOROBENZAMIDE

CROSS RELATION TO PRIOR APPLICATIONS

The present invention is a continuation of U.S. patent application Ser. No. 13/893,382, now allowed, filed May 14, 2013, which is a continuation of U.S. patent application Ser. No. 12/740,970, now U.S. Pat. No. 8,476,296 B2, filed Apr. 30, 2010, which is a §371 application of International Application No. PCT/US2010/021926, filed Jan. 25, 2010, which claims benefit to U.S. Provisional Application No. 61/147,260, filed Jan. 26, 2009, each of which is incorporated herein by reference in its entirety.

FIELD OF THE INVENTION

The present invention relates to compounds that bind to and modulate the activity of neuronal nicotinic acetylcholine receptors, to processes for preparing these compounds, to pharmaceutical compositions containing these compounds, and to methods of using these compounds for treating a wide variety of conditions and disorders, including those associated with dysfunction of the central nervous system (CNS).

BACKGROUND OF THE INVENTION

The therapeutic potential of compounds that target neuronal nicotinic receptors (NNRs), also known as nicotinic acetylcholine receptors (nAChRs), has been the subject of several reviews (see, for example, Braining et al., *Ann. Rep. Med. Chem.* 40: 3 (2005), Hogg and Bertrand, *Curr. Drug Targets: CNS Neurol. Disord.* 3: 123 (2004), Suto and Zacharias, *Expert Opin. Ther. Targets* 8: 61 (2004), Dani et al., *Bioorg. Med. Chem. Lett.* 14:1837 (2004). Bencherif and Schmitt, *Curr. Drug Targets: CNS Neurol. Disord.* 1: 349 (2002)). Among the kinds of indications for which NNR ligands have been proposed as therapies are cognitive disorders, including Alzheimer's disease, attention deficit disorder, and schizophrenia (Newhouse et al., *Curr. Opin. Pharmacol.* 4: 36 (2004), Levin and Rezvani, *Curr. Drug Targets: CNS Neurol. Disord.* 1: 423 (2002), Graham et al., *Curr. Drug Targets: CNS Neurol. Disord.* 1: 387 (2002), Ripoll at al., *Curr. Med. Res. Opin.* 20(7): 1057 (2004), and McEvoy and Allen, *Curr. Drug Targets: CNS Neurol. Disord.* 1: 433 (2002)); pain and inflammation (Decker et al., *Curr. Top. Med. Chem.* 4(3): 369 (2004), Vincler, *Expert Opin. Invest. Drugs* 14(10): 1191 (2005), Jain. *Cur. Opin. Inv. Drugs* 5: 76 (2004). Miao et al., *Neuroscience* 123: 777 (2004)); depression and anxiety (Shytle et al., *Mol. Psychiatry* 7: 525 (2002), Damaj et al., *Mol. Pharmacol.* 66: 675 (2004), Shytle et al., *Depress. Anxiety* 16: 89 (2002)); neurodegeneration (O'Neill et al., *Curr. Drug Targets: CNS Neurol. Disord.* 1: 399 (2002), Takata et al., *J. Pharmacol. Exp. Ther.* 306: 772 (2003), Marrero et al., *J. Pharmacol. Exp. Ther.* 309:16 (2004)): Parkinson's disease (Jonnala and Buccafusco, *J. Neurosci. Res.* 66: 565 (2001)); addiction (Dwoskin and Crooks, *Biochem. Pharmacol.* 63: 89 (2002), Coe et al., *Bioorg. Med. Chem. Lett.* 15(22): 4889 (2005)); obesity (Li et al., *Curr. Top. Med. Chem.* 3: 899 (2003)); and Tourette's syndrome (Sacco et al., *J. Psychopharmacol.* 18(4): 457 (2004), Young et al., *Clin. Ther.* 23(4): 532 (2001)).

There exists a heterogeneous distribution of nAChR subtypes in both the central and peripheral nervous systems. For instance, the nAChR subtypes which are predominant in vertebrate brain are α4β2, α7, and α3β2, whereas those which predominate at the autonomic ganglia are α3β4 and those of neuromuscular junction are α1β1δγ and α1β1δε (see Dwoskin et al., *Exp. Opin. Ther. Patents* 10: 1561 (2000) and Holliday et al. *J. Med. Chem.* 40(26). 4169 (1997)).

A limitation of some nicotinic compounds is that they are associated with various undesirable side effects due to non-specific binding to multiple nAChR subtypes. For example, binding to and stimulation of muscle and ganglionic nAChR subtypes can lead to side effects which can limit the utility of a particular nicotinic binding compound as a therapeutic agent.

The compounds of the present invention exhibit a high degree of specific binding to the α7 nAChR subtype and low affinity for the α4β2 subtype as well as ganglionic and muscle nAChR subtypes. Thus, these compounds can serve as therapeutic modulators of α7 nAChRs in patients in need of such treatment, without producing side effects caused by non-specific nAChR subtype binding.

SUMMARY OF THE INVENTION

The present invention includes (2S,3R)—N-2-((3-pyridinyl)methyl)-1-azabicyclo[2.2.2]oct-3-yl)-3,5-difluorobenzamide (Formula I) or a pharmaceutically acceptable salt thereof.

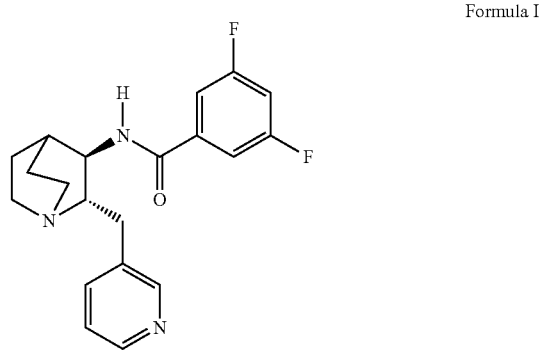 [SMILES: O=C(N[C@@H]1C2CCN(CC2)[C@H]1Cc1cccnc1)c1cc(F)cc(F)c1]

Formula I

The compound of the present invention binds with high affinity to NNRs of the α7 subtype and exhibit selectivity for this subtype over the α4β2 NNR subtype, as well as over ganglion and muscle subtypes.

The present invention includes pharmaceutical compositions comprising the compound of the present invention or a pharmaceutically acceptable salt thereof. The pharmaceutical compositions of the present invention can be used for treating or preventing a wide variety of conditions or disorders, including those disorders characterized by dysfunction of nicotinic cholinergic neurotransmission or the degeneration of the nicotinic cholinergic neurons.

The present invention includes a method for treating or preventing disorders and dysfunctions, such as CNS disorders and dysfunctions, inflammation, inflammatory response associated with bacterial and/or viral infection, pain, metabolic syndrome, autoimmune disorders, or other disorders described in further detail herein. The present invention includes a method for modulating neovascularization. The methods involve administering to a subject a therapeutically effective amount of a compound of the present invention, including a salt thereof, or a pharmaceutical composition that includes such compounds. Additionally, the present invention includes compounds that have utility as diagnostic agents and in receptor binding studies as described herein.

The foregoing and other aspects of the present invention are explained in further detail in the detailed description and examples set forth below.

BRIEF DESCRIPTION OF THE FIGURES

FIG. 5 depicts a dose response for each of Compound A and Compound B with α7 nicotinic receptors.

FIGS. 8A, 8B, and 8C depict electrophysiological response for interaction of Compound B with Ach, regarding activation of the nicotinic α7 receptor.

DETAILED DESCRIPTION

Definitions

Figure 1:
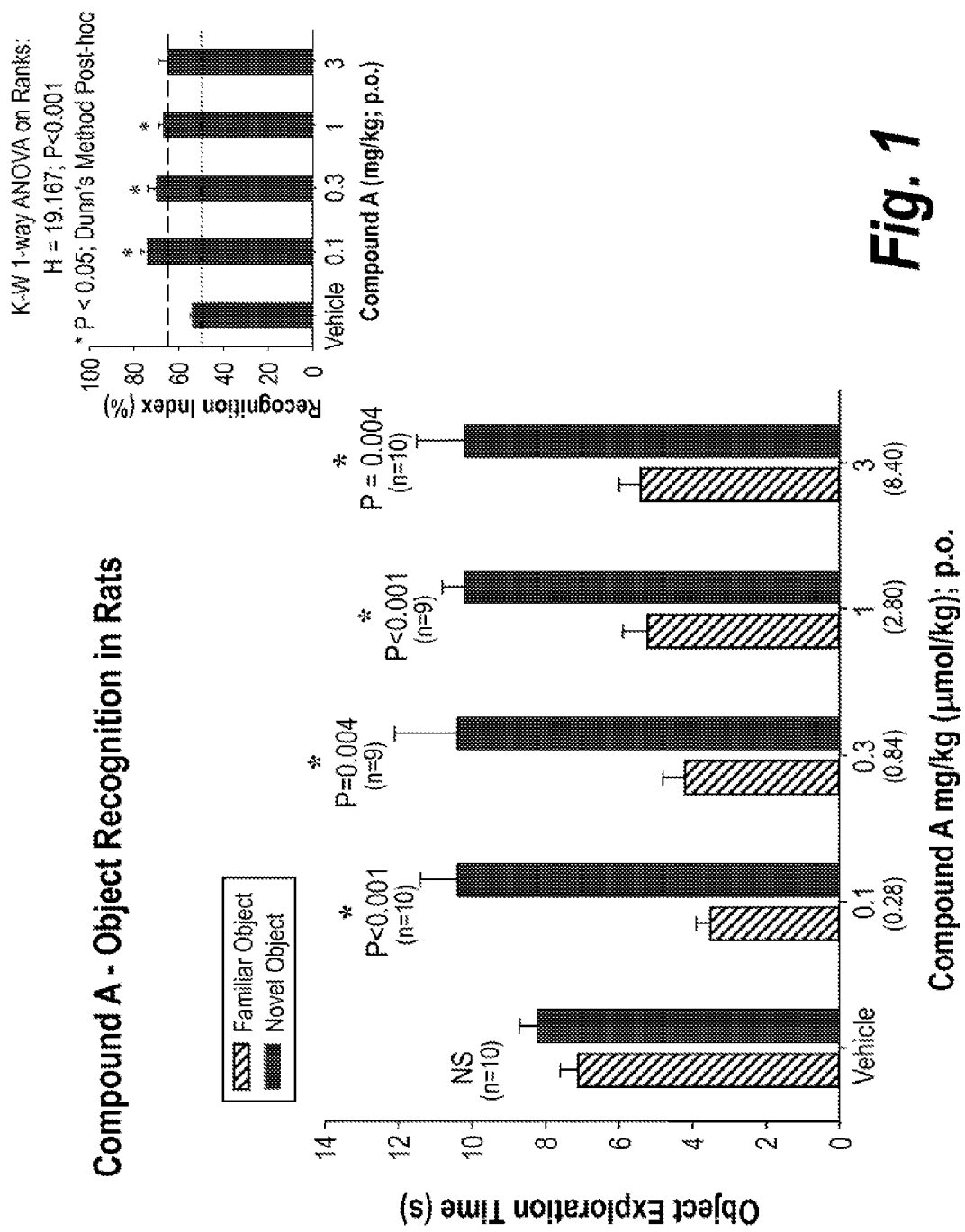
FIG. 1 depicts novel object recognition (NOR) vs. dose for (2S,3R)—N-2-((3-pyridinyl)methy)-1-azabicyclo[2.2.2]oct-3-yl)-3,5-difluorobenzamide or pharmaceutically acceptable salt thereof. A statistically significant effect was observed for doses as low as 0.1 mg/kg.
Figure 2:
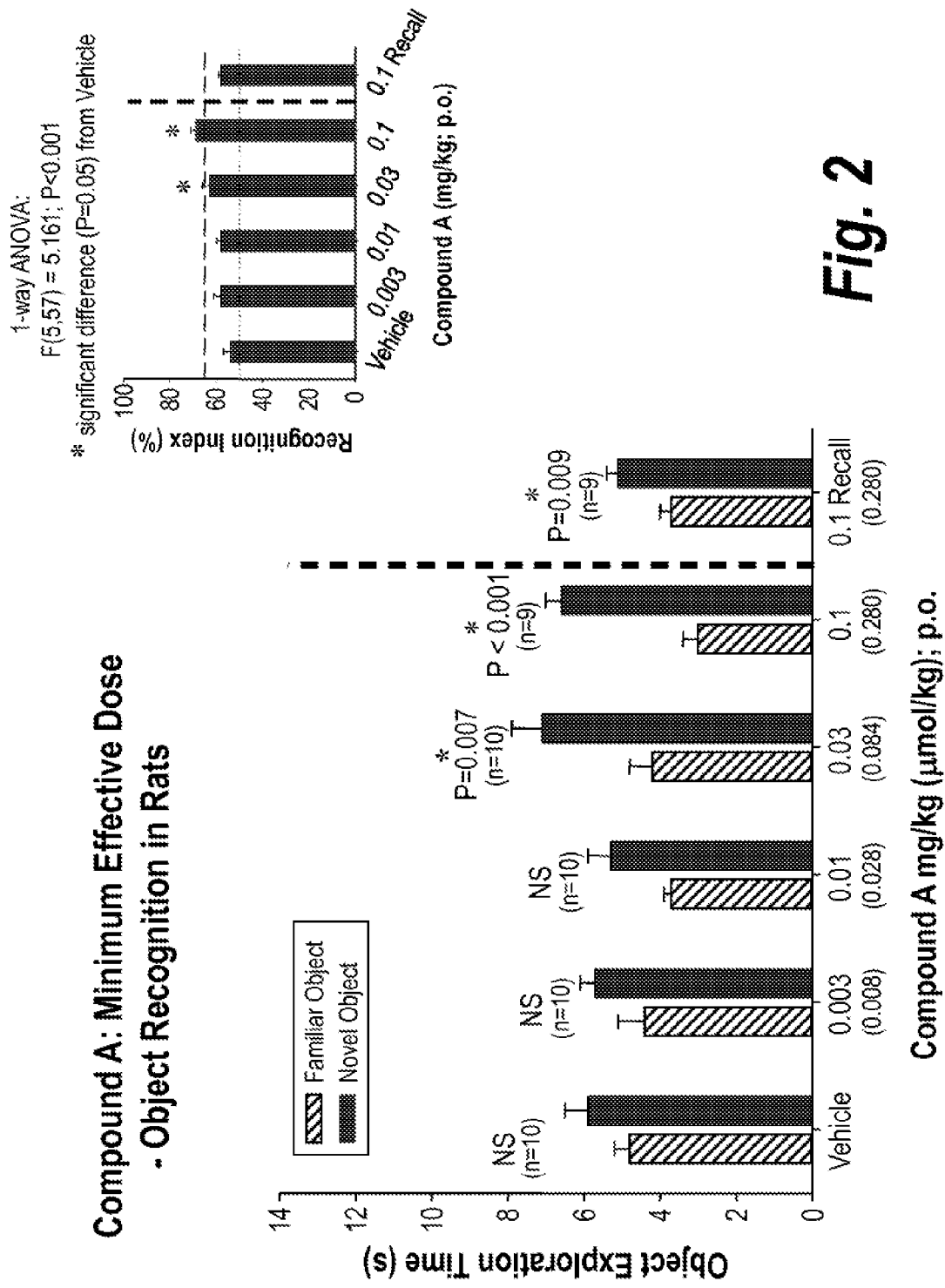
FIG. 2 depicts the data used for the determination of the minimum effective dose for novel object recognition (NOR) upon administration of (2S,3R)—N-2-((3-pyridinyl)methyl)-1-azabicyclo[2.2.2]oct-3-yl)-3,5-difluorobenzamide or pharmaceutically acceptable salt thereof. A statistically significant effect was observed for doses as low as 0.03 mg/kg.
Figure 3:
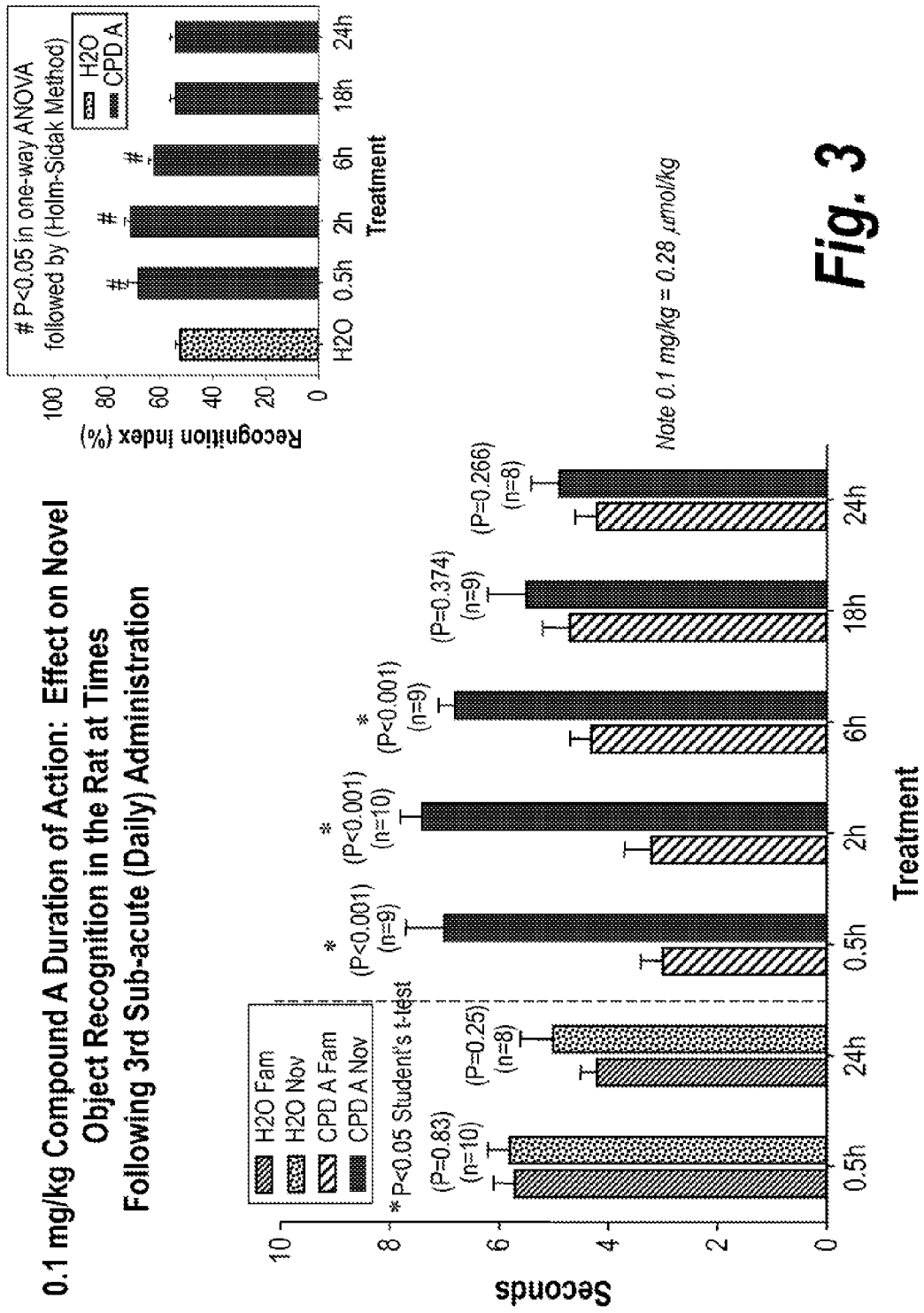
FIG. 3 depicts novel object recognition (NOR) vs. time following the 3rd administration of 0.1 mg/kg (2S,3R)—N-2-((3-pyridinyl)methyl)-1-azabicyclo[2.2.2]oct-3-yl)-3,5-difluorobenzamide or a pharmaceutically acceptable salt thereof. A statistically significant effect was observed for doses out to 6 h after dosing.

The following definitions are meant to clarify, but not limit, the terms defined. If a particular term used herein is not specifically defined, such term should not be considered indefinite. Rather, terms are used within their accepted meanings.

As used herein, the term "compound(s)" may be used to mean the free base form, or alternatively, a salt form of (2S, 3R)—N-2-((3-pyridinyl)methyl)-1-azabicyclo[2.2.2]oct-3-yl)-3,5-difluorobenzamide, depending on the context, which will be readily apparent. Those skilled in the art will be able to distinguish the difference.

For ease of reference, (2S,3R)—N-2-((3-pyridinyl)methyl)-1-azabicyclo[2.2.2]oct-3-yl)-3,5-difluorobenzamide (Formula I) or a pharmaceutically acceptable salt thereof is also referred to as Compound A. Additionally, a structural analog is used herein for comparative purposes. (2S,3R)—N-2-((3-Pyridinyl)methyl)-1-azabicyclo[2.2.2]oct-3-yl)-4-fluorobenzamide or a pharmaceutically acceptable salt thereof is referred to as Compound B. Compound B is a single isomer of a racemic mixture as published in WO 04/76449, herein incorporated by reference.

As used herein, the term "pharmaceutically acceptable" refers to carrier(s), diluent(s), excipient(s) or salt forms of the compound of the present invention that are compatible with the other ingredients of the formulation and not deleterious to the recipient of the pharmaceutical composition.

As used herein, the term "pharmaceutical composition" refers to a compound of the present invention optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutically effective amount", "therapeutic amount," or "effective dose" refer to an amount of the compound of the present invention sufficient to elicit the desired pharmacological or therapeutic effects, thus resulting in effective prevention or treatment of a disorder. Prevention of the disorder may be manifested by delaying or preventing the progression of the disorder, as well as the onset of the symptoms associated with the disorder. Treatment of the disorder may be manifested by a decrease or elimination of symptoms, inhibition or reversal of the progression of the disorder, as well as any other contribution to the well being of the patient.

As will be discussed in more detail below and with reference to FIGS. 1 2, 3, and 4, a statistically significant effect is observed for doses of the compound of Formula I, or a pharmaceutically acceptable salt thereof, as low as 0.03 µM/kg, including effects observed out to 18 hours after dosing. The effective dose can vary, depending upon factors such as the condition of the patient, the severity of the symptoms of the disorder, and the manner in which the pharmaceutical composition is administered. Thus, as used herein, the effective dose may be less than 100 mg, preferably less than 50 mg, more preferably less than 10 mg, and most preferably less than 1 mg. These effective doses typically represent the amount administered as a single dose, or as one or more doses administered over a 24 hours period.

Compounds

One aspect of the present invention includes a compound (2S,3R)—N-2-((3-pyridinyl)methyl)-1-azabicyclo[2.2.2]oct-3-yl)-3,5-difluorobenzamide (Formula I) or a pharmaceutically acceptable salt thereof.

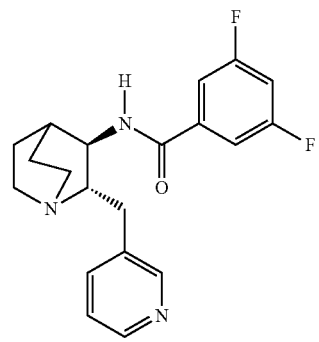

Formula I

In one embodiment, the compound is substantially free of one or more of (2R,3S)—N-2-((3-pyridinyl)methyl)-1-azabicyclo[2.2.2]oct-3-yl)-3,5-difluorobenzamide, (2R,3R)—N-2-((3-pyridinyl)methyl)-1-azabicyclo[2.2.2]oct-3-yl)-3,5-difluorobenzamide, and (2S,3S)—N-2-((3-pyridinyl)methyl)-1-azabicyclo[2.2.2]oct-3-yl)-3,5-difluorobenzamide.

In one embodiment, the is an acid addition salt, wherein the acid is selected from hydrochloric acid, methanesulfonic acid, maleic acid, phosphoric acid, 1-hydroxy-2-naphthoic acid, malonic acid, L-tartaric acid, fumaric acid, citric acid. L-malic acid, R-mandelic acid. S-mandelic acid, succinic acid, 4-acetamidobenzoic acid, adipic acid, galactaric acid, di-p-toluoyl-D-tartaric acid, oxalic acid, D-glucuronic acid, 4-hydroxybenzoic acid, 4-methoxybenzoic acid, (1S)-(+)-10-camphorsulfonic acid, (1R,3S)-(+)-camphoric acid, and p-toluenesulfonic acid, or a hydrate or solvate thereof. In a further embodiment, the molar ratio of acid to (2S,3R)—N-2-((3-pyridinyl)methyl)-1-azabicyclo[2.2.2]oct-3-yl)-3,5-difluorobenzamide is 1:2 or 1:1.

Another aspect of the present invention includes a compound selected from:

(2S,3R)—N-2-((3-pyridinyl)methyl)-1-azabicyclo[2.2.2]oct-3-yl)-3,5-difluorobenzamide mono-hydrochloride or a hydrate or solvate thereof;

(2S,3R)—N-2-((3-pyridinyl)methyl)-1-azabicyclo[2.2.2]oct-3-yl)-3,5-difluorobenzamide mono-phosphate or a hydrate or solvate thereof;

(2S,3R)—N-2-((3-pyridinyl)methyl)-1-azabicyclo[2.2.2]oct-3-yl)-3,5-difluorobenzamide mono-4-hydroxybenzoate or a hydrate or solvate thereof; and (2S,3R)—N-2-((3-pyridinyl)methyl)-1-azabicyclo[2.2.2]oct-3-yl)-3,5-difluorobenzamide hemi-4-hydroxybenzoate or a hydrate or solvate thereof.

Another aspect of the present invention includes a compound, (2S,3R)—N-2-((3-pyridinyl)methyl)-1-azabicyclo[2.2.2]oct-3-yl)-3,5-difluorobenzamide or a pharmaceutically acceptable salt thereof containing less than 25%, preferably containing less than 15%, preferably containing less than 5%, preferably containing less than 2%, preferably containing less than 1% of (2R,3R)—, (2S,3S)—, or (2R,3S)—N-2-((3-pyridinyl)methyl)-1-azabicyclo[2.2.2]oct-3-yl)-3,5-difluorobenzamide, either individually or in combination, by weight.

Another aspect of the present invention includes a compound (2S,3R)—N-2-((3-pyridinyl)methyl)-1-azabicyclo[2.2.2]oct-3-yl)-3,5-difluorobenzamide (Formula I) or a pharmaceutically acceptable salt thereof which is substantially crystalline. Another aspect includes a polymorphic form of a compound (2S,3R)—N-2-((3-pyridinyl)methyl)-1-azabicyclo[2.2.2]oct-3-yl)-3,5-difluorobenzamide hydrochloride characterized by an x-ray diffraction pattern comprising one or more peaks within ±0.5 degrees 2θ of the following peaks:

| 2θ |
|---|
| 8.4 |
| 8.8 |
| 11.9 |
| 13.2 |
| 15.2 |
| 16.0 |
| 17.6 |
| 18.4 |
| 18.9 |
| 19.9 |
| 20.1 |
| 21.3 |
| 23.1 |
| 25.4 |
| 26.2 |

Figure 9:
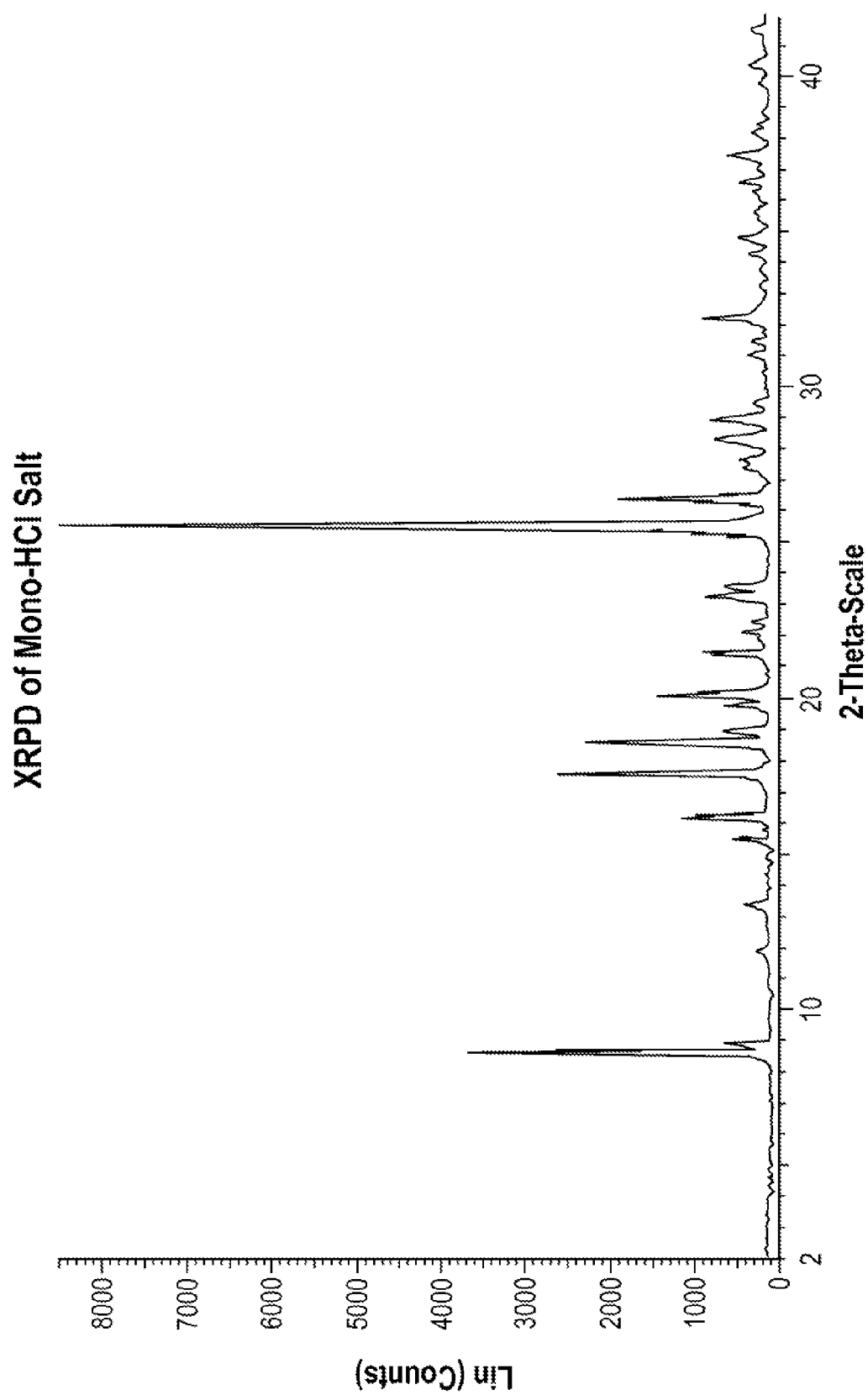
FIG. 9 is an x-ray diffraction pattern for Compound A mono-hydrochloride salt.

Another aspect of the present invention is a polymorphic form of a compound (2S,3R)—N-2-((3-pyridinyl)methyl)-1-azabicyclo[2.2.2]oct-3-yl)-3,5-difluorobenzamide hydrochloride characterized by an x-ray powder diffraction pattern that substantially corresponds to FIG. 9.

Another aspect of the present invention includes use of a compound of the present invention, in the manufacture of a medicament for the treatment or prevention of an α7-mediated disease or dysfunction. Another aspect of the present invention includes a method for treating or preventing an α7-mediated disease or dysfunction, comprising administering a therapeutically effective amount of a compound of the present invention. Another aspect of the present invention includes a compound of the present invention for use in treating or preventing an α7-mediated disease or dysfunction. In one embodiment, the disease or dysfunction is selected from the group consisting of:

i) pain, including one or more of acute, neurologic, inflammatory, neuropathic, chronic pain, severe chronic pain, post-operative pain, pain associated with cancer, angina, renal or biliary colic, menstruation, migraine, gout, arthritis, rheumatoid disease, teno-synovitis, vasculitis, trigeminal or herpetic neuralgia, diabetic neuropathy pain, causalgia, low back pain, deafferentation syndromes, and brachial plexus avulsion;

ii) metabolic syndrome, weight gain, type I diabetes mellitus, type II diabetes mellitus, or diabetic neuropathy;

iii) inflammation, including one or more of psoriasis, asthma, atherosclerosis, idiopathic pulmonary fibrosis, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, pouchitis, glomerulonephritis, lupus nephritis, thrombosis, and graft vs. host reaction; and iv) cognition, including one or more of age-associated memory impairment, mild cognitive impairment, pre-senile dementia, early onset Alzheimer's disease, senile dementia, dementia of the Alzheimer's type, mild to moderate dementia of the Alzheimer's type, Lewy body dementia, vascular dementia, Alzheimer's disease, stroke, AIDS dementia complex, attention deficit disorder, attention deficit hyperactivity disorder, dyslexia, schizophrenia, schizophreniform disorder, schizoaffective disorder, cognitive deficits in schizophrenia, and cognitive dysfunction in schizophrenia.

Another aspect of the present invention includes a pharmaceutical composition comprising a compound of the present invention and one or more pharmaceutically acceptable carrier.

Another aspect of the present invention includes a method of enhancing acetylcholine-induced current comprising administering an effective amount of a compound of the present invention.

Another embodiment of the present invention includes (2S,3R)—N-2-((3-pyridinyl)methyl)-1-azabicyclo[2.2.2]oct-3-yl)-3,5-difluorobenzamide or a pharmaceutically acceptable salt thereof with reference to any one of the Examples.

Another embodiment of the present invention includes (2S,3R)—N-2-((3-pyridinyl)methyl)-1-azabicyclo[2.2.2]oct-3-yl)-3,5-difluorobenzamide or a pharmaceutically acceptable salt thereof for use as an active therapeutic substance.

Another embodiment of the present invention includes a method of modulating NNR in a subject in need thereof through the administration of (2S,3R)—N-2-((3-pyridinyl)methyl)-1-azabicyclo[2.2.2]oct-3-yl)-3,5-difluorobenzamide or a pharmaceutically acceptable salt thereof.

The scope of the present invention includes combinations of aspects and embodiments.

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the invention. Such isotopically labeled compounds are useful as research or diagnostic tools.

The present invention includes a salt or solvate of the (2S,3R)—N-2-((3-pyridinyl)methyl)-1-azabicyclo[2.2.2]oct-3-yl)-3,5-difluorobenzamide, including combinations thereof, such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt: alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

As noted herein, the present invention includes specific compounds, which are identified herein with particularity. The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (see, for example, T. W. Green and P. G. M. Wuts. *Protecting Groups in Organic Synthesis, 3rd Edition*, John Wiley & Sons, New York (1999)). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds useful as intermediates in the preparation of compounds of the present invention along with methods for their preparation.

The compounds can be prepared according to the following methods using readily available starting materials and reagents. In these reactions, variants may be employed which are themselves known to those of ordinary skill in this art, but are not mentioned in greater detail.

Salt Forms

One aspect of the present invention relates to novel salt forms of (2S,3R)—N-2-((3-pyridinyl)methyl)-1-azabicyclo[2.2.2]oct-3-yl)-3,5-difluorobenzamide.

(2S,3R)—N-2-((3-pyridinyl)methyl)-1-azabicyclo[2.2.2]oct-3-yl)-3,5-difluorobenzamide in the free base form is a solid with limited water solubility. However, the free base will react with both inorganic and organic acids to make certain acid addition salts that have physical properties that are advantageous for the preparation of pharmaceutical compositions such as crystallinity, water solubility, and stability toward chemical degradation. Typically, these salt forms are pharmaceutically acceptable salts.

The present invention includes pharmaceutically acceptable salts of (2S,3R)—N-2-((3-pyridinyl)methyl)-1-azabicyclo[2.2.2]oct-3-yl)-3,5-difluorobenzamide. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or solvates, such as ethanol solvates.

One aspect of the present invention includes acid addition salts of (2S,3R)—N-2-((3-pyridinyl)methyl)-1-azabicyclo[2.2.2]oct-3-yl)-3,5-difluorobenzamide wherein the acid is selected from hydrochloric acid, methanesulfonic acid, maleic acid, phosphoric acid, 1-hydroxy-2-naphthoic acid, malonic acid, L-tartaric acid, fumaric acid, citric acid, L-malic acid, R-mandelic acid, S-mandelic acid, succinic acid, 4-acetamidobenzoic acid, adipic acid, galactaric acid, di-p-toluoyl-D-tartaric acid, oxalic acid, D-glucuronic acid, 4-hydroxybenzoic acid, 4-methoxybenzoic acid, (1S)-(+)-10-camphorsulfonic acid. (1R,3S)-(+)-cemphoric acid, and p-toluenesulfonic acid. The present invention also includes hydrates and solvates of these salt forms.

The stoichiometry of the salts comprising the present invention can vary. For example, it is typical that the molar ratio of acid to (2S,3R)—N-2-((3-pyridinyl)methyl)-1-azabicyclo[2.2.2]oct-3-yl)-3,5-difluorobenzamide is 1:2 or 1:1, but other ratios, such as 3:1, 1:3, 2:3, 3:2 and 2:1, are possible.

In one embodiment of the present invention, the salt has a stoichiometry of acid to of (2S,3R)—N-2-((3-pyridinyl)methyl)-1-azabicyclo[2.2.2]oct-3-yl)-3,5-difluorobenzamide of 1:2. In another embodiment, the salt has a stoichiometry of acid of (2S,3R)—N-2-((3-pyridinyl)methyl)-1-azabicyclo[2.2.2]oct-3-yl)-3,5-difluorobenzamide of 1:1.

As herein noted, depending upon the manner by which the salts described herein are formed, the salts can have crystal structures that occlude solvents that are present during salt formation. Thus, the salts can occur as hydrates and other solvates of varying stoichiometry of solvent relative to (2S,3R)—N-2-((3-pyridinyl)methyl)-1-azabicyclo[2.2.2]oct-3-yl)-3,5-difluorobenzamide.

Another embodiment of the present invention includes (2S,3R)—N-2-((3-pyridinyl)methyl)-1-azabicyclo[2.2.2]oct-3-yl)-3,5-difluorobenzamide or a hydrate or solvate thereof.

Another embodiment of the present invention includes (2S,3R)—N-2-((3-pyridinyl)methyl)-1-azabicyclo[2.2.2]oct-3-yl)-3,5-difluorobenzamide mono-hydrochloride or a hydrate or solvate thereof.

Another embodiment of the present invention (2S,3R)—N-2-((3-pyridinyl)methyl)-1-azabicyclo[2.2.2]oct-3-yl)-3,5-difluorobenzamide mono-phosphate or a hydrate or solvate thereof.

Another embodiment of the present invention includes (2S,3R)—N-2-((3-pyridinyl)methyl)-1-azabicyclo[2.2.2]oct-3-yl)-3,5-difluorobenzamide mono-4-hydroxybenzoate or a hydrate or solvate thereof.

Another embodiment of the present invention includes (2S,3R)—N-2-((3-pyridinyl)methyl)-1-azabicyclo[2.2.2]oct-3-yl)-3,5-difluorobenzamide hemi-4-hydroxybenzoate or a hydrate or solvate thereof.

A further aspect of the present invention includes processes for the preparation of the salts. The precise conditions under which the salts are formed may be empirically determined. The salts may be obtained by crystallization under controlled conditions.

One embodiment of the present invention includes a method for the preparation of (2S,3R)—N-2-((3-pyridinyl)methyl)-1-azabicyclo[2.2.2]oct-3-yl)-3,5-difluorobenzamide or a pharmaceutically acceptable salt thereof containing less than 25%, preferably less than 15%, more preferably less than 5%, even more preferably less than 2%, and most preferably less than 1% of (2R,3R)—, (2S,3S)—, or (2R,3S)—N-2-((3-pyridinyl)methyl)-1-azabicyclo[2.2.2]oct-3-yl)-3,5-difluorobenzamide by weight either individually or in combination.

The method for preparing the salt forms can vary. The preparation (2S,3R)—N-2-((3-pyridinyl)methyl)-1-azabicyclo[2.2.2]oct-3-yl)-3,5-difluorobenzamide salt forms typically involves:

(i) mixing the free base, or a solution of the free base of suitably pure (2S,3R)—N-2-((3-pyridinyl)methyl)-1-azabicyclo[2.2.2]oct-3-yl)-3,5-difluorobenzamide in a suitable solvent, with any of the acids in pure form or as a solution of any of the acids in a suitable solvent, typically 0.5 to 1 equivalents of the acid:

(ii) (a) cooling the resulting salt solution if necessary to cause precipitation;

or (ii) (b) adding a suitable anti-solvent to cause precipitation;

or (ii) (c) evaporating the first solvent and adding and new solvent and repeating either steps (ii) (a) or step (ii) (b);

and (iii) filtering and collecting the salt.

The stoichiometry, solvent mix, solute concentration, and temperature employed can vary. Representative solvents that can be used to prepare or recrystallize the salt forms include, without limitation, ethanol, methanol, propanol, isopropyl alcohol, isopropyl acetate, acetone, ethyl acetate, toluene, water, methyl ethyl ketone, methyl isobutyl ketone, tert-butyl methyl ether, tetrahydrofuran, dichloromethane, n-heptane, and acetonitrile.

Several of these salts demonstrate stability sufficient to establish their promise in the production of pharmaceutical preparations. Such stability can be demonstrated in a variety of ways. Propensity to gain and release atmospheric moisture can be assessed by dynamic vapor sorption (DVS).

General Synthetic Methods

A synthesis of (2S,3R)—N-2-((3-pyridinyl)methyl)-1-azabicyclo[2.2.2]oct-3-yl)-3,5-difluorobenzamide is achieved by O-(benzotriazol-1-yl)-N,N,N,1-tetramethyluronium hexafluorophosphate (HBTU) mediated coupling of (2S,3R)-3-amino-2-((3-pyridinyl)methyl)-1-azabicyclo[2.2.2]octane (obtained as described in PCT/US08/71872, herein incorporated by reference with regard to such synthesis) and 3,5-difluorobenzoic acid as illustrated in Scheme 1.

Scheme 1

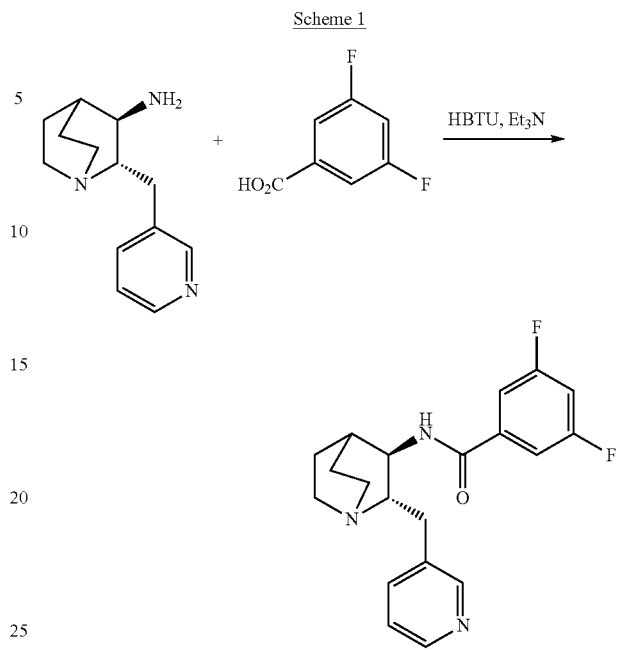

The synthesis of (2S,3R)—N-2-((3-pyridinyl)methyl)-1-azabicyclo[2.2.2]oct-3-yl)-3,5-difluorobenzamide can be similarly achieved by the use of other agents to activate the carboxylic acid. For example, the use of activating agents such as N,N'-dicyclohexylcarbodiimide (DCC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotriazol-1-yl)-N,N,N',N'-bis(tetramethylene)uronium hexafluorophosphate (HBPyU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and (1-ethyl-3-(3-dimethylaminopropyl)carbodiimide) (EDCl) with 1-hydroxybenzotriazole (HOBt), as well as those described in, for example, Kiso and Yajima. Peptides, pp 39-91, Academic Press, San Diego, Calif. (1995), are well known to those skilled in the art.

Methods of Treatment

The compounds of the present invention have the ability to selectively bind to and modulate the activity of α7 NNRs. Consequently, these compounds can be used for the prevention or treatment of various conditions or disorders for which other types of nicotinic compounds have been proposed or are shown to be useful as therapeutics, such as CNS disorders, inflammation, inflammatory response associated with bacterial and/or viral infection, pain, metabolic syndrome, autoimmune disorders or other disorders described in further detail herein. These compounds can be used for modulating neovascularization and as diagnostic agents in receptor binding studies (in vitro and in vivo). Such therapeutic and other teachings are described, for example, in Williams et al., *Drug News Perspec.* 7(4): 205 (1994), Americ et al., *CNS Drug Rev.* 1(1): 1-26 (1995), Americ et al., *Exp. Opin. Invest. Drugs* 5(1): 79-100 (1996), Bencherif et al., *J. Pharmacol. Exp. Ther.* 279: 1413 (1996), Lippiello et al., *J. Pharmacol. Exp. Ther* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem,* 40(28), 4169-94 (1997). Bannon et al., *Science* 279: 77 (1998). PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al., and other references previously listed herein.

CNS Disorders

The compounds and their pharmaceutical compositions are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention can be used to treat or prevent are: age-associated memory impairment (AAMI), mild cognitive impairment (MCI), age-related cognitive decline (ARCO), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, tardive dyskinesia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, oppositional defiant disorder, Tourette's syndrome, autism, drug and alcohol addiction, tobacco addiction, obesity, cachexia, psoriasis, lupus, acute cholangitis, aphthous stomatitis, ulcers, asthma, ulcerative colitis, inflammatory bowel disease, Crohn's disease, spastic dystonia, diarrhea, constipation, pouchitis, viral pneumonitis, arthritis (including rheumatoid arthritis and osteoarthritis), endotoxaemia, sepsis, atherosclerosis, idiopathic pulmonary fibrosis, acute pain, chronic pain, neuropathies, urinary incontinence, diabetes and neoplasias.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to a general medical conditions, dementias and other cognitive disorders, including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, *cannabis*-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and Impulse-control disorders.

Cognitive performance may be assessed with a validated cognitive scale, such as, for example, the cognitive subscale of the Alzheimer's Disease Assessment Scale (ADAS-cog). One measure of the effectiveness of the compounds of the present invention in improving cognition may include measuring a patient's degree of change according to such a scale.

The above conditions and disorders are discussed in further detail, for example, in the American Psychiatric Association: Diagnostic and Statistical Manual of Mental Disorders. Fourth Edition, Text Revision, Washington, D.C. American Psychiatric Association, 2000. This Manual may also be referred to for greater detail on the symptoms and diagnostic features associated with substance use, abuse, and dependence.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory reflex." *Nature* 420: 853-9 (2002)). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that can be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, pouchitis, glomerulonephritis, lupus nephritis, thrombosis, and graft vs. host reaction.

Inflammatory Response Associated with Bacterial and/or Viral Infection

Many bacterial and/or viral infections are associated with side effects brought on by the formation of toxins, and the body's natural response to the bacteria or virus and/or the toxins. The body's response to infection often involves generating a significant amount of TNF and/or other cytokines. The over-expression of these cytokines can result in significant injury, such as septic shock (when the bacteria is sepsis), endotoxic shock, urosepsis and toxic shock syndrome.

Cytokine expression is mediated by NNRs, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Examples of such bacterial infections include anthrax, botulism, and sepsis. Some of these compounds may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle at al. Other agents effective against bacterial and other toxins can be effective and their therapeutic effect can be complemented by co-administration with the compounds described herein.

Pain

The compounds can be administered to treat and/or prevent pain, including acute, neurologic, inflammatory, neuropathic and chronic pain. The analgesic activity of compounds described herein can be demonstrated in models of persistent inflammatory pain and of neuropathic pain, performed as described in U.S. Published Patent Application No. 20010056084 A1 (Allgeier et al.) (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, post-operative pain and pain associated with various conditions including cancer, angina, renal or biliary colic, menstruation, migraine and gout). Inflammatory pain may be of diverse genesis, including arthritis and rheumatoid disease, tenosynovitis and vasculitis. Neuropathic pain includes trigeminal or herpetic neuralgia, diabetic neuropathy pain, causalgia, low back pain and deafferentation syndromes such as brachial plexus avulsion.

Neovascularization

The $\alpha 7$ NNR is associated with neovascularization. Inhibition of neovascularization, for example, by administering antagonists (or at certain dosages, partial agonists) of the $\alpha 7$ NNR can treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of $\alpha 7$ NNR.

Specific antagonism of $\alpha 7$ NNR-specific activity reduces the angiogenic response to inflammation, ischemia, and neoplasia. Guidance regarding appropriate animal model systems for evaluating the compounds described herein can be found, for example, in Heeschen, C. et al., "A novel angiogenic pathway mediated by non-neuronal nicotinic acetylcholine receptors," *J. Clin. Invest.* 110(4):527-36 (2002).

Representative tumor types that can be treated using the compounds described herein include NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma. Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cisplatin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Other Disorders

In addition to treating CNS disorders, inflammation, and undesirable neovascularization, and pain, the compounds of the present invention can be also used to prevent or treat certain other conditions, diseases, and disorders in which NNRs play a role. Examples include autoimmune disorders such as Lupus, disorders associated with cytokine release, cachexia secondary to infection (e.g., as occurs in AIDS, AIDS related complex and neoplasia), obesity, pemphitis, urinary incontinence, retinal diseases, infectious diseases, myasthenia. Eaton-Lambert syndrome, hypertension, osteoporosis, vasoconstriction, vasodilatation, cardiac arrhythmias, type I diabetes, bulimia, anorexia as well as those indications set forth in published PCT application WO 98/25619. The compounds of this invention can also be administered to treat convulsions such as those that are symptomatic of epilepsy, and to treat conditions such as syphillis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α7 receptor subtype. For this purpose the compounds of the present invention most preferably are labeled with a radioactive isotopic moiety such as $^{11}C$, $^{18}F$, $^{76}Br$, $^{123}I$ or $^{125}I$.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected NNR subtypes. In addition to humans, the compounds can also be administered to animals, such as mice, rats, dogs, and monkeys. SPECT and PET imaging can be carried out using any appropriate technique and apparatus. See Villemagne at al., In: Arneric et al. (Eds.) *Neuronal Nicotinic Receptors: Pharmacology and Therapeutic Opportunities,* 235-250 (1998) and U.S. Pat. No. 5,853,696 to Elmalch et al.

The radiolabeled compounds bind with high affinity to selective NNR subtypes (e.g., α7) and preferably exhibit negligble non-specific binding to other nicotinic cholinergic receptor subtypes (e.g., α4β2 and those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected NNR subtypes (e.g., α7 receptor subtypes). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif at al.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes namely, the α7 receptor subtype.

Receptor Binding

The compounds of this invention can be used as reference ligands in binding assays for compounds which bind to NNR subtypes, particularly the α7 receptor subtype. For this purpose the compounds of this invention are preferably labeled with a radioactive isotopic moiety such as $^3H$, or $^{14}C$. Examples of such binding assays are described in detail below.

Pharmaceutical Compositions

Although it is possible to administer the compound of the present invention in the form of a bulk active chemical, it is preferred to administer the compound in the form of a pharmaceutical composition or formulation. Thus, one aspect the present invention includes pharmaceutical compositions comprising the compound of the present invention and one or more pharmaceutically acceptable carriers, diluents, or excipients. Another aspect of the invention provides a process for the preparation of a pharmaceutical composition including admixing the compound of the present invention with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses The administration of the pharmaceutical compositions described herein can be intermittent, or at a gradual, continuous, constant or controlled rate. The pharmaceutical compositions may be administered to a warm-blooded animal, for example, a mammal such as a mouse, rat, cat, rabbit, dog, pig, cow, or monkey; but advantageously is administered to a human being. In addition, the time of day and the number of times per day that the pharmaceutical composition is administered can vary.

The compound of the present invention may be used in the treatment of a variety of disorders and conditions and, as such, may be used in combination with a variety of other suitable therapeutic agents useful in the treatment or prophylaxis of those disorders or conditions. Thus, one embodiment of the present invention includes the administration of the compound of the present invention in combination with other therapeutic compounds. For example, the compound of the present invention can be used in combination with other NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), antipyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenytoin and gabapentin), vasodilators (such as prazosin and sildenafil), mood stabilizers (such as valproate and aripiprazole), anti-cancer drugs (such as anti-proliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole). Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention includes combination therapy comprising administering to the subject a therapeutically or prophylactically effective amount of the compound of the present invention and one or more other therapy including chemotherapy, radiation therapy, gene therapy, or immunotherapy.

Examples

The following examples are provided to illustrate the present invention, and should not be construed as limiting thereof. In these examples, all parts and percentages are by weight, unless otherwise noted.

Nuclear Magnetic Resonance (NMR) Spectrometry

NMR spectra were collected on either a Varian Unity 300 MHz instrument or a Bruker 400 MHz instrument equipped with an auto-sampler and controlled by a DRX400 console. Automated experiments were acquired using ICONNMR v4.0.4 (build 1) running with Topspin v 1.3 (patch level 8) using the standard Bruker loaded experiments. For non-routine spectroscopy, data were acquired through the use of Topspin alone.

Melting Point

A Fisher-Johns hot stage melting point apparatus was used, at a setting corresponding to a heating rate of about 5° C. per min.

Differential Scanning Calorimetry (DSC)

Dsc data were collected on a Mettler DSC 823e equipped with a 50 position auto-sampler. The instrument was calibrated for energy and temperature using certified indium. Typically 0.5-1.5 mg of each sample, in a pin-holed aluminum pen, was heated at 10° C.·min-1 from 25° C. to 300° C. A nitrogen purge at 50 ml/min-1 was maintained over the sample. Instrument control and data analysis were performed using the stare v 9.10 software package.

X-Ray Powder Diffraction (XRPD)

Method 1

X-Ray Powder Diffraction patterns were collected on a Siemens 05000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection was Diffrac Plus XRD Commander v2.3.1 and the data were analysed and presented using Diffrac Plus EVA v 11,0.0.2 or v 13.0.0.2.

Samples were run under ambient conditions as flat plate specimens using powder as received. Approximately 30 mg of the sample was gently packed into a cavity cut into polished, zerobackground (510) silicon wafer. The sample was rotated in its own plane during analysis. The details of the data collection are:

Angular range: 2 to 42 °2θ
Step size: 0.05 °2θ or 0.1 °2θ
Collection time: 4 s·step$^{-1}$ Method 2

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heatconducting compound. The sample was then heated to the appropriate temperature at ca. $10°$ C.·min$^{-1}$ and subsequently held isothermally for ca 1 minute before data collection was initiated.

Single Crystal X-Ray Diffraction (SCXD)

Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1

Synthesis of (2S,3R)—N-2-((3-pyridinyl)methyl)-1-azabicyclo[2.2.2]oct-3-yl)-3,5-difluorobenzamide To a suspension of (2S,3R)-3-amino-2-((3-pyridinyl)methyl)-1-azabicyclo[2.2.2]octane (20 mg, 0.092 mmol, prepared as described in PCT WO 09/018505, herein incorporated by reference with regard to such synthesis), o-(benzotriazol-1-yl)-N,N,N,1-tetramethyluronium hexafluorophosphate (HBTU, 41.7 mg, 0.110 mmol) and 3,5-difluorobenzoic acid (17.4 mg, 0.110 mmol) in N,N-dimethylformamide (DMF, 2 ml) was added triethylamine (28 mg, 0.28 mmol) at room temperature. The reaction mixture was stirred overnight at room temperature, diluted with ethyl acetate (200 ml) and washed with 20% aqueous potassium carbonate. The residue was purified by silica gel chromatography with the eluent methanol:triethylamine=300:1. The solvent was removed to give (2S,3R)—N-2-((3-pyridinyl)methyl)-1-azabicyclo[2.2.2]oct-3-yl)-3,5-difluorobenzamide (30 mg, 76%), purity by HPLC: 100% (214 nm), 98.2% (254 nm); $^1$H NMR (400 MHz, CDCl$_3$) d 8.48 (d, j=2.0 Hz, 1H), 8.36 (dd, j=1.7 Hz, j=4.9 Hz, 1H), 7.56-7.60 (m, 1H), 7.14-7.20 (m, 1H), 7.05-7.14 (m, 2H), 6.87-6.96 (m, 1H), 6.23 (d, j=7.8 Hz, 1H), 3.88-3.96 (m, 1H), 3.02-3.13 (m, 1H), 2.82-3.00 (m, 4H), 2.65-2.82 (m, 2H), 1.97-2.05 (m, 1H), 1.58-1.84 (m, 3H), 1.43-1.55 (m, 1H); ESI-MS 358.1 (MH)$^+$.

Example 2

Synthesis of (2S,3R)—N-2-((3-pyridinyl)methyl)-1-azabicyclo[2.2.2]oct-3-yl)-3,5-difluorobenzamide fumarate To a solution of 3,5-difluorobenzoic acid (9.36 g, 59.2 mmol), chloroform (200 mL) and triethylamine (16.34 g, 161.5 mmol) at 25° C. was added HBTU (22.5 g, 59.2 mmol). The mixture was heated to 40-42° C. for 45 min resulting in the formation of a white suspension. The suspension was cooled to 10° C. and a solution of (2S,3R)-3-amino-2-((3-pyridinyl)methyl)-1-azabicyclo[2.2.2]octane (11.7 g, 53.8 mmoles) in chloroform (50 mL) was added over a 15-20 min period and stirred for 1.5 h. The reaction mixture was heated to 40-42° C. and additional 3,5-difluorobenzoic acid (2.0 g, 13 mmol) and HBTU (4 g, 11 mmol) were added, followed by stirring at 40-42° C. for 2 h and then at ambient temperature for 16 h. The reaction mixture was quickly quenched with water (200 mL), and under stirring, the pH of the aqueous layer was adjusted to pH=10-11 with 10 wt % aqueous sodium hydroxide. The layers were separated and the organic layer was washed twice with water (100 mL). The solvent was removed in vacuo to afford 22.9 g of a viscous orange solid. The strength of the product in the crude oil was determined at 66.0 wt % by quantitative HPLC against a reference standard: this corresponds to a yield of 15.1 g (78%). The oil was dissolved in methyl ethyl ketone (50 mL) which was subsequently distilled off in vacuo; this process was repeated a total of three times. A 500 mL three-necked, round-bottomed flask, equipped with an overhead stirrer, temperature probe, dropping funnel and condenser, was charged with fumaric acid (4.9 g, 42 mmol) and methyl ethyl ketone (150 mL). The suspension was heated to 78° C. which led to complete dissolution of the acid. A solution of the (2S,3R)—N-2-((3-pyridinyl)methyl)-1-azabicyclo[2.2.2]oct-3-yl)-3,5-difluorobenzamide in methyl ethyl ketone (50 mL) was added slowly, keeping the internal temperature above 75° C. After completion of the addition, the suspension was stirred for 30-45 min at 78° C. and the heat source was turned off. The suspension was stirred overnight, filtered and the cake was dried at 50° C. in vacuo for 16 h to afford (2S,3R)—N-2-((3-pyridinyl)methyl)-1-azabicyclo[2.2.2]oct-3-yl)-3,5-difluorobenzamide fumarate as a light yellow, crystalline solid (99.6% pure by HPLC), mp 208-210° C. Yield: 65% for two steps. $^1$H NMR (D$_2$O, 400 MHz): δ 8.30 (d, J=5.6 Hz, 1H); 8.06 (d, J=7.5 Hz, 1H); 7.48 (dd, J=8.7 Hz, J=5.6 Hz, 1H); 6.97-7.06 (m, 1H); 6.75-6.85 (m, 2H); 6.49 (s, 2H); 4.15 (d, J=7.5 Hz, 1H): 3.69-3.81 (m, 1H); 3.40-3.59 (m, 2H); 3.17-3.40 (m, 4H); 2.03-2.18 (m, 2H): 1.91-2.03 (m, 2H), 1.78-1.91 (m, 1H).

Example 3

Synthesis of (2S,3R)—N-2-((3-pyridinyl)methyl)-1-azabicyclo[2.2.2]oct-3-yl)-3,5-difluorobenzamide mono-hydrochloride Procedure A: To a solution of 250 mg (0.7 mmol) of (2S, 3R)—N-2-((3-pyridinyl)methyl)-1-azabicyclo[2.2.2]oct-3-yl)-3,5-difluorobenzamide in 10 mL of isopropyl acetate was added aqueous hydrochloric acid (65 μL of a 37% (w/w), 0.78 mmol). The solution was heated to 50° C. and cooled to 0° C. over a 4 h period. The mono-hydrochloride sample was a mixture of gum and white powder at 0° C. The sample was then heated to 20° C. and cooled again to 0° C. (cooling ramp 5° C. Imin). The resulting solids were collected and dried under vacuum at 25° C. for 24 h. mp (DSC)=274.8° C.

Procedure B: Concentrated hydrochloric acid (0.54 mL of 37% (w/w), 6.6 mmol) was added drop-wise, with ice bath cooling, to tetrahydrofuran (THF, ~4 mL) and diluted to 5 mL volume with THF. This solution was added drop-wise (over a 5 min period) to a warm (45-50° C.) solution of (2S,3R)—N-2-((3-pyridinyl)methyl)-1-azabicyclo[2.2.2]oct-3-yl)-3,5-difluorobenzamide (2.43 g of 96.8% purity, 6.58 mmol) in acetone (20 mL). Solids began to precipitate. The mixture was heated near boiling for 15 min, cooled to ambient temperature and allowed to sit 16 h. The solids were collected by suction filtration under nitrogen, washed with acetone and dried in a vacuum oven (85° C. 3 h). This left 2.26 g of material that was 93% pure by LCMS. The entire sample was digested in hot (near boiling) 2-propanol (25 mL) for 10 min.

The mixture was cooled to ambient temperature and allowed to stand for 3 h. The solids were collected by suction filtration under nitrogen and dried in a vacuum oven (85° C., 2.5 h). The resulting white crystals were >99% pure by HPLC, weighed 2.03 g (78.4% yield) and melted at 273-276° C. $^1$H NMR (400 MHz, DMSO-d$_6$) δ 10.45 (broad s, 1H), 8.66 (d, 1H), 8.54 (s, 1H), 8.28 (d, 1H), 7.76 (d, 1H), 7.41 (m, 1H), 7.24 (m, 3H), 4.14 (m, 1H), 4.07 (m, 1H), 3.46 (m, 2H), 3.10-3.35 (m, 4H), 2.06 (m, 3H), 1.90 (m, 1H), 1.69 (m, 1H). Elemental analysis: Calculated for $C_{20}H_{21}ON_3F_2$·HCl (C, 60.99%; H, 5.63%; N, 10.67%). Found (C, 60.94%; 60.91%; H, 5.64%; 5.66%; N, 10.63%; 10.67%).

Example 4

Synthesis of (2S,3R)—N-2-((3-pyridinyl)methyl)-1-azabicyclo[2.2.2]oct-3-yl)-3,5-difluorobenzamide mono-phosphate To a solution of 250 mg (0.7 mmol) of (2S,3R)—N-2-((3-pyridinyl)methyl)-1-azabicyclo[2.2.2]oct-3-yl)-3,5-difluorobenzamide in 5 mL of isopropyl alcohol was added 780 μL (0.78 mmol, 1.1 eq) of a 1M phosphoric acid in THF solution. The solution was heated to 50° C. and cooled to 0° C. over a 4 hour period. A white immobile slurry formed at 0° C., which remained after warming the sample to room temperature. Evaporation of the solvent yielded crystalline material that was collected and dried under vacuum at 25° C. for 24 h. mp (DSC)=219.2° C. $^1$H NMR (400 MHz, DMSO-d$_6$) δ 8.48 (s, 1H), 8.34 (d, 1H), 8.28 (d, 1H), 7.68 (d, 1H), 7.43 (m, 1H), 7.24 (m, 3H), 5.04 (br s), 3.84 (m, 1H), 2.70-3.35 (m, 7H), 1.60-1.90 (m, 4H), 1.40 (m, 1H).

Example 5

Synthesis of (2S,3R)—N-2-((3-pyridinyl)methyl)-1-azabicyclo[2.2.2]oct-3-yl)-3,5-difluorobenzamide mono-4-hydroxybenzoate To a solution of 250 mg (0.70 mmol) of (2S,3R)—N-2-((3-pyridinyl)methyl)-1-azabicyclo[2.2.2]oct-3-yl)-3,5-difluorobenzamide in 5 mL of isopropyl acetate was added 780 μL (0.78 mmol, 1.1 eq) of a 1M 4-hydroxybenzoic acid in THF solution. The solution was heated to 50° C. and cooled to 0° C. over a 4 hour period. The mono-4-hydroxybenzoate was obtained as a gum. The crystallization was obtained after seeding with the hemi-4-hydroxybenzoate and 48 hours of maturation between 50° C. and room temperature (4 hours cycle) of an evaporated mixture of gum and solvent (only a quarter of the starting volume was remaining). The solid was then isolated by evaporation of the solvent under nitrogen. The resulting solids were collected and dried under vacuum at 25° C. for 24 h. mp (DSC)=144.0° C.

Example 6

Synthesis of (2S,3R)—N-2-((3-pyridinyl)methyl)-1-azabicyclo[2.2.2]oct-3-yl)-3,5-difluorobenzamide hemi-4-hydroxybenzoate To a solution of 71.5 mg (0.20 mmol) of (2S,3R)—N-2-((3-pyridinyl)methyl)-1-azabicyclo[2.2.2]oct-3-yl)-3,5-difluorobenzamide in 3.5 mL of isopropyl acetate was added 100 μL (0.1 mmol, 0.5 eq) of a 1M 4-hydroxybenzoic acid in THF solution. The isopropyl acetate was evaporated to yield (2S,3R)—N-2-((3-pyridinyl)methyl)-1-azabicyclo[2.2.2]oct-3-yl)-3,5-difluorobenzamide mono-4-hydroxybenzoate as a solid which was collected and dried under vacuum at 25° C. for 24 h. mp(DSC)=106.0° C. $^1$H NMR (400 MHz, DMSO-de) δ 10.23 (br s), 8.43 (s, 1H), 8.29 (s, 1H), 8.28 (s, 1H), 7.78 (d, 1H), 7.61 (m, 1H), 7.41 (m, 3H), 7.22 (m, 1H), 6.80 (d, 1H), 3.66 (m, 1H), 2.70-3.20 (m, 7H), 1.50-1.90 (m, 4H), 1.20 (m, 1H).

Example 7

Synthesis of (2S,3R)—N-2-((3-pyridinyl)methyl)-1-azabicyclo[2.2.2]oct-3-yl)-3,5-difluorobenzamide monohydrate To a solution of (2S,3R)—N-2-((3-pyridinyl)methyl)-1-azabicyclo[2.2.2]oct-3-yl)-3,5-difluorobenzamide (993 mg, 2.80 mmol) water (5 mL) was added chloroform (15 mL). The pH of the aqueous layer was adjusted to pH=10-11 with 10 weight % sodium hydroxide. The biphasic mixture was shaken vigorously, and the layers were allowed to separate. The chloroform layer was isolated, and the aqueous layer was extracted once more with chloroform (9 mL). The combined chloroform layers were washed once with water (7 mL), filtered over a bed of anhydrous magnesium sulfate and concentrated in vacuo to afford a colorless, clear oil with a tendency to foam. The material was treated with methyl tert-butyl ether (MTBE, 10-15 mL) followed by solvent distillation in vacuo; this process was repeated once more. The material was dissolved in MTBE (10-15 mL) and heptane was added until a white cloudiness appeared. At this point, a slow distillation of volatiles at 50-55° C. at ambient pressure was started and additional solid material separated out. The distillation was halted and the material was collected by filtration and washed with a small amount of heptane. The material was dried in vacuo at 55° C. under a vacuum/nitrogen bleed for 60 h and at 70-85° C. for 40 h to afford 400 mg of (2S,3R)—N-2-((3-pyridinyl)methyl)-1-azabicyclo[2.2.2]oct-3-yl)-3,5-difluorobenzamide mono-hydrate as a white brittle solid: $α_D^{26.6°\ C.}$=40°; elemental analysis, calc: C (63.99); H (6.18); N (11.19), $H_2O$ (4.8 weight %). found: C (64.23); H (6.27); N (11.18); $H_2O$ (4.48). $^1$H NMR (CDCl$_3$, 400 MHz): δ 8.46 (d, J=2 Hz, 1H); 8.35 (dd, J=4.8 Hz, J=2 Hz, 1H); 7.56-7.61 (m, 1H); 7.08-7.19 (m, 3H); 6.87-6.95 (m, 1H), 6.32 (d, J=8.1 Hz, 1H); 3.89-3.95 (m, 1H); 3.00-3.12 (m, 1H), 2.84-2.99 (m, 4H): 2.88-2.84 (m, 2H); 1.98-2.04 (m, 1H); 1.83 (s, 2H); 1.58-1.79 (m, 3H); 1.44-1.54 (m, 1H). Decomposes at 240° C.

Example 8

Figure 11:
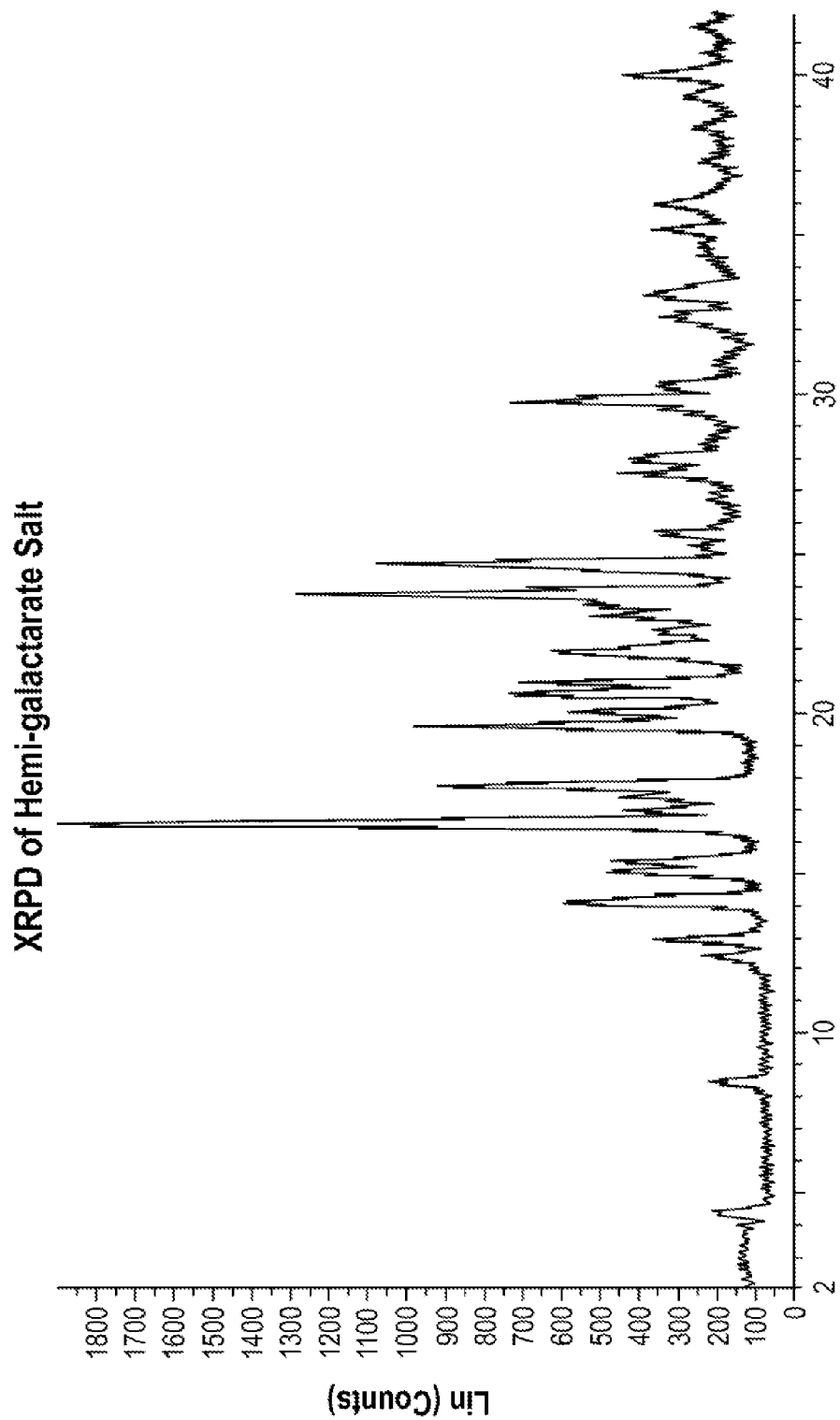
FIG. 11 is an x-ray diffraction pattern for Compound A hemi-galactarate salt.

Synthesis of (2S,3R)—N-2-((3-pyridinyl)methyl)-1-azabicyclo[2.2.2]oct-3-yl)-3,5-difluorobenzamide hemi-galactarate To a stirred solution of (2S,3R)—N-2-((3-pyridinyl)methyl)-1-azabicyclo[2.2.2]oct-3-yl)-3,5-difluorobenzamide (357 mg, 1.00 mmol) in absolute ethanol (10 mL) at 70-72° C. was added galataric acid (neat) (105 mg, 0.50 mmol) in small portions. Heating was continued for an additional 15 min after completion of acid addition. The solution was slowly cooled to ambient temperature. After standing for 2 h, the solids were collected by vacuum filtration, washed with ethanol, and dried under a nitrogen cone for 30 min. The resulting material was dried for 3 h at 75° C. in a vacuum oven to remove residual ethanol. The results of XRPD analysis are shown in FIG. 11.

Example 9

Salt screening of (2S,3R)—N-2-((3-pyridinyl)methyl)-1-azabicyclo[2.2.2]oct-3-yl)-3,5-difluorobenzamide Stock solutions of (2S,3R)—N-2-((3-pyridinyl)methyl)-1-azabicyclo[2.2.2]oct-3-yl)-3,5-difluorobenzamide free base were prepared as follows:

20 mg/ml in IPA, 25 mg/ml in i-ProAc—Counter-ions 1-12
25 mg/ml in i-ProAc—Counter-ions 13-20

Each vial was charged with 2 ml of free base stock solution at ambient (40-50 mg of free base/vial). To each vial was then added appropriate volumes of stock acid solution, (1M in THF, unless otherwise stated) at either 1.1 or 2.2 equivalents at ambient. Insoluble acids were added as solids accordingly. All samples were the warmed to 50° C. prior to cooling to 0° C. over 10 hours. All amorphous solids, including gums and oils, were placed on maturation (ambient-50° C. in 4 hour cycles over 2 days) followed by XRPD re-analysis. To those samples which remained amorphous post maturation 2 ml of methyl ethyl ketone was added and the samples further matured for 3 days. Clear solutions were sequentially evaporated to approximately to half and then to quarter volume at 50° C. Remaining solutions were further cooled to 5° C. prior to the complete removal of the solvent under vacuum. All resulting solids were analyzed by XRPD and any crystalline samples with unique XRPD patterns were analyzed further by $^1$HNMR/Ion chromatography, solid state stability at 40° C./75% RH for 1 week and aqueous solubility (target 10 mg/ml at 25° C. unbuffered)

| | Acidic counter-ions selected for the salt selection study | | | | | | |
|---|---|---|---|---|---|---|---|
| | | | | pKa | | | |
| Nr. | Acid | Class | 1 | 2 | 3 | LogP | MW |
| 1 | Hydrochloric acid 37 wt % (12M) | 1 | −6.10 | | | — | 36.46 |
| 2 | Sulphuric acid | 1 | −3.00 | 1.92 | | −1.03 | 98.08 |
| 3 | Methane sulfonic acid | 2 | −1.20 | | | −1.89 | 96.10 |
| 4 | Maleic acid | 1 | 1.92 | 6.23 | | −0.01 | 116.07 |
| 5 | Phosphoric acid | 1 | 1.96 | 7.12 | 12.32 | −2.15 | 98.00 |
| 6 | L-Tartaric acid | 1 | 3.02 | 4.36 | | −1.43 | 150.09 |
| 7 | Fumaric acid used as powder | 1 | 3.03 | 4.38 | | −0.01 | 116.07 |
| 8 | Citric acid | 1 | 3.13 | 4.76 | 6.40 | −1.72 | 192.12 |
| 9 | L-Malic acid | 1 | 3.46 | 5.10 | | −1.26 | 134.09 |
| 10 | 1-Hydroxy-2-Naphthoic acid used as powder | 2 | 2.70 | 13.50 | | 3.29 | 186.17 |
| 11 | 4-Hydroxy benzoic acid | 2 | | | | | |
| 12 | Succinic acid 1M in MeOH | 1 | 4.21 | 5.64 | | −0.59 | 118.09 |
| 13 | Benzene sulfonic acid | 2 | 0.70 | | | 0.47 | 158.18 |
| 14 | p-Toluene sulfonic acid 1M in EtOH | 2 | −1.34 | | | 0.93 | 190.22 |
| 15 | Hippuric acid used as powder | 1 | 3.55 | | | 0.31 | 179.17 |
| 16 | D-Gluconic acid 50% in water | 1 | 3.76 | | | −3.18 | 196.16 |
| 17 | Acetic acid | 1 | 4.76 | | | −0.29 | 60.05 |
| 18 | Benzoic acid 1M in IPA | 2 | 4.19 | | | | |
| 19 | Propionic acid | 2 | 4.87 | | | 0.25 | 74.07 |
| 20 | L-Aspartic acid used as powder | 1 | 1.88 | 3.65 | | −0.67 | 133.11 |

TABLE

Salt screen summary

| Counter-ion | Solvent | Target Stoichiometry | Observation on addition of acid at RT | Observation at 0° C. | XRPD analysis after filtration | XRPD after 48 hours of maturation | XRPD after evaporation and maturation in MEK | Observation on 2nd maturation |
|---|---|---|---|---|---|---|---|---|
| Hydrochloride | 2-propanol | mono salt | Clear solution | White powder | Crystalline✿ | Crystalline✿ | n/a | n/a |
|  | Isopropyl acetate | bis salt | Clear solution | Clear solution | n/a | Clear solution | Crystalline | n/a |
| Sulphate (sulfate) | 2-propanol | mono salt | Precipitate | White powder | Crystalline✿ | Crystalline✿ | n/a | n/a |
|  | Isopropyl acetate | bis salt | Precipitate | White powder | gum✿ | Crystalline✿ | n/a | n/a |
| Mesylate | 2-propanol | mono salt | Precipitate | White powder | gum✿ | gum | n/a | gum |
|  | Isopropyl acetate | bis salt | Precipitate | White powder | Amorphous✿ | Amorphous✿ | Amorphous✿ | White powder |
| Maleate | 2-propanol | mono salt | Clear solution | White powder | gum✿ | Clear solution | gum✿ | gum✿ |
|  | Isopropyl acetate | bis salt | Clear solution | Clear solution | n/a | n/a | n/a | White powder |
| Phosphate | 2-propanol | mono salt | Precipitate | gum | n/a | Amorphous✿ | n/a | n/a |
|  | Isopropyl acetate | bis salt | Precipitate | gum | n/a | Crystalline✿ | n/a | gum |
| Fumarate | 2-propanol | mono salt | Clear solution | Clear solution | n/a | Clear solution | n/a | gum |
|  | Isopropyl acetate | bis salt | Clear solution | gum | gum✿ | gum✿ | n/a | gum |
| Citrate | 2-propanol | mono salt | Precipitate | White powder | Not enough material | Crystalline✿ | n/a | gum |
|  | Isopropyl acetate | bis salt | Precipitate | Precipitate | Stopped experiment ♥ Mainly amorphous✿ | White powder | Amorphous✿ | White powder |
| Malate | 2-propanol | mono salt | Clear solution | Precipitate | Amorphous✿ | Crystalline✿ | n/a | n/a |
|  | Isopropyl acetate | bis salt | Clear solution | Precipitate | gum✿ | Crystalline✿ | n/a | gum✿ |
| Xinafoate | 2-propanol | mono salt | Precipitate | White powder | gum✿ | n/a | gum✿ | gum✿ |
|  | Isopropyl acetate | bis salt | Precipitate | White powder | Amorphous✿ | Amorphous✿ | Amorphous✿ | White powder |
| 4-Hydroxybenzoate | 2-propanol | mono salt | Precipitate | White powder | Amorphous✿ | Amorphous✿ | Amorphous✿ | White powder |
|  | Isopropyl acetate | bis salt | Clear solution | Clear solution | n/a | Clear solution | n/a | White powder |
| Succinate | 2-propanol | mono salt | Clear solution | White powder | Amorphous✿ | Amorphous | Amorphous✿ | White powder |
|  | Isopropyl acetate | bis salt | Clear solution | Clear solution | n/a | Low Crystallinity✿ | n/a | gum✿ |
|  | 2-propanol | mono salt | Clear solution | Clear solution | n/a | Clear solution | gum✿ | gum✿ |
|  | Isopropyl acetate | bis salt | Clear solution | Clear solution | n/a | Clear solution | gum✿ | gum✿ |
|  | 2-propanol | mono salt | Clear solution | Clear solution | n/a | Clear solution | gum✿ | gum✿ |
|  | Isopropyl acetate | bis salt | Clear solution | Clear solution | n/a | Clear solution | gum✿ | n/a |
|  | 2-propanol | mono salt | Clear solution | Clear solution | n/a | Crystalline✿ | gum✿ | gum✿ |
|  | Isopropyl acetate | bis salt | Clear solution | Clear solution | n/a | Clear solution | gum✿ | gum✿ |
|  | 2-propanol | mono salt | Clear solution | Clear solution | n/a | Clear solution | gum✿ | gum✿ |
|  | Isopropyl acetate | bis salt | Clear solution | Clear solution | n/a | Clear solution | gum✿ | gum✿ |

TABLE-continued

Salt screen summary

| Counter-ion | Solvent | Target Stoichiometry | Observation on addition of acid at RT | Observation at 0° C. | XRPD analysis after filtration | XRPD after 48 hours of maturation | XRPD after evaporation and maturation in MEK | Observation on 2nd maturation | XRPD post evaporation and storage at 5° C. |
|---|---|---|---|---|---|---|---|---|---|
| Benzylate | Isopropyl Acetate | mono salt | Precipitate | White powder | Amorphous ♣ | Low Crystallinity ♣ | n/a | n/a | n/a |
| Tosylate | Isopropyl Acetate | mono salt | Clear solution | Clear solution | n/a | Clear solution | Crystalline ♣ | n/a | n/a |
| Hippurate | Isopropyl Acetate | mono salt | Clear solution | Clear solution | n/a | Clear solution | gum ♣ | gum ♣ | n/a |
| Gluconate | Isopropyl Acetate | mono salt | Clear solution | Clear solution | n/a | Clear solution | gum ♣ | gum ♣ | n/a |
| Acetate | Isopropyl Acetate | mono salt | Clear solution | Clear solution | n/a | Clear solution | gum ♣ | gum ♣ | n/a |
| Benzoate | Isopropyl Acetate | mono salt | Clear solution | Clear solution | n/a | Clear solution | gum ♣ | gum ♣ | Crystalline ♣ |
| Propionate | Isopropyl Acetate | mono salt | Clear solution | Clear solution | n/a | Clear solution | gum ♣ | gum ♣ | n/a |
| Aspartate | Isopropyl Acetate | mono salt | Non-dissolved | Non-dissolved | Crystalline same as the acid ♥ | Crystalline same as the acid ♥ | Crystalline same as the acid ♥ | n/a | n/a |

Key:
♣ Crystalline
♣ Amorphous
♥ No further analysis performed
n/a Not applicable

TABLE

Characterization after primary salt screening

Figure 12:
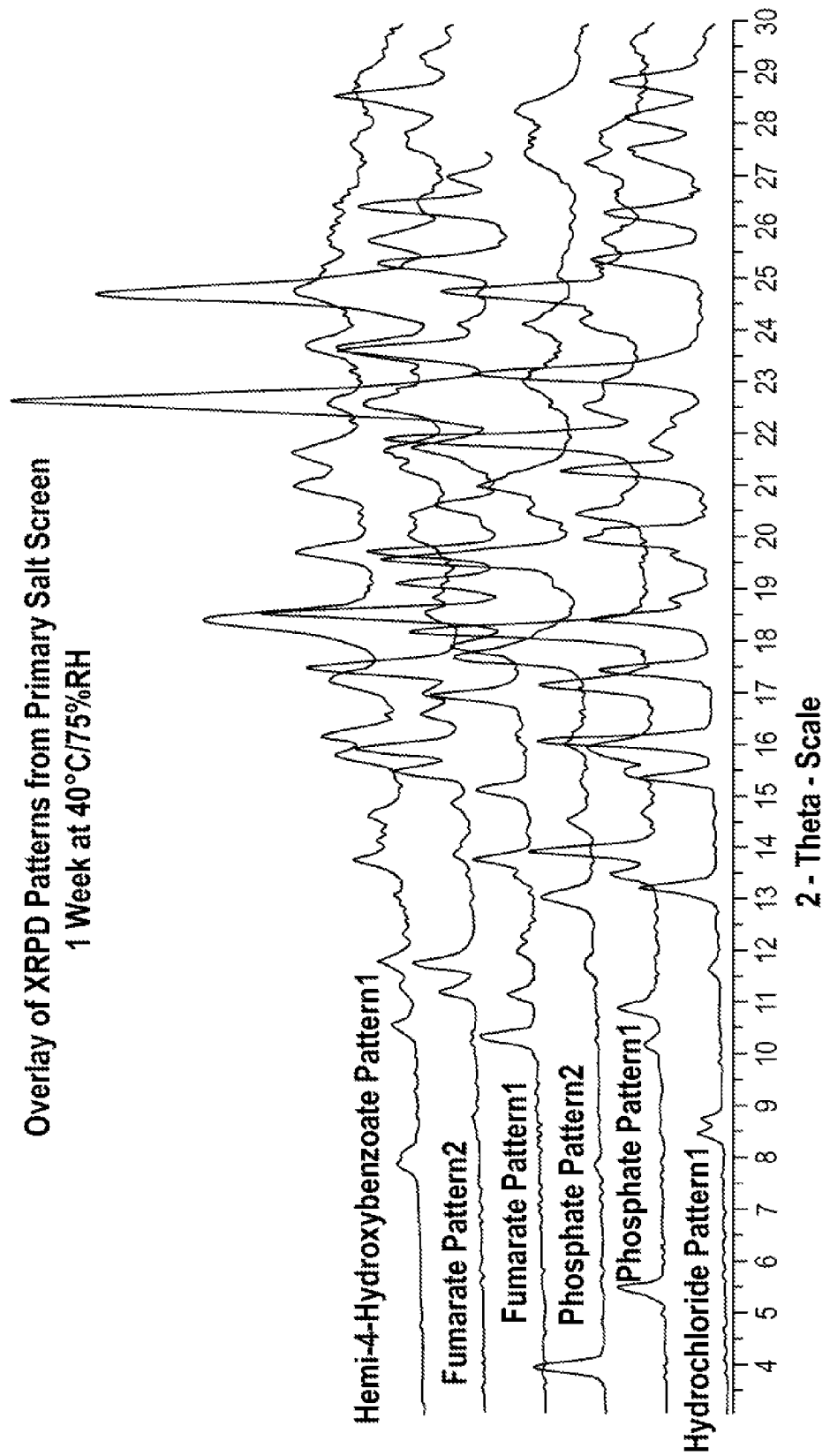
FIG. 12 illustrates an overlay of six (6) different x-ray diffraction patterns for salts from the salt screen for Compound A.

| Salt | Target Stoichiometry | XRPD after filtration | 1H NMR | Stoichiometry (Acid Base) Ion Chromatography | XRPD 40° C./75% RH 1 Week (See FIG. 12) | Aqueous Solubility |
|---|---|---|---|---|---|---|
| Hydrochloride | mono salts | Pattern1 | Confirmation of the salt formation | 1.0:1 | Pattern1♣ | >10 mg/mL |
|  | bis salts | Pattern2 Pattern3 | Confirmation of the salt formation | n/a | deliquescent♠ | n/a |
| Phosphate | mono salts | Pattern1 | Confirmation of the salt formation | 1.0:1 | Pattern1♣ | >10 mg/mL |
|  | mono and bis salts | Pattern2 | Confirmation of the salt formation | n/a | Pattern1♣ + Pattern2♣ | >10 mg/mL |
| Fumarate | mono salt | Pattern1 | Confirmation of the formation of a mono salt 1.0:1 | n/a | Pattern1♣ | >10 mg/mL |
|  | bis salt | Pattern2 | Confirmation of the formation of a bis salt 1.9:1 | n/a | Pattern2♣ | >10 mg/mL |
| 4-Hydroxybenzoate | mono salt | Pattern1 | Confirmation of the formation of a hemi salt 0.5:1 | n/a | Pattern1♣ | >10 mg/mL |
| Benzoate | mono salt | Pattern1 | Confirmation of mono salt formation | n/a | Pattern2♣ | 0.8 mg/mL |
| Sulphate | mono salt | Pattern1 | Confirmation of the salt formation | n/a | deliquescent♠ | n/a |
| Mesylate | mono and bis salts | Pattern1 | Confirmation of the formation of a mono salt | n/a | deliquescent♠ | n/a |
| Malate | bis salts | Pattern1 Low crystallinity | Confirmation of the salt formation 1.4:1 | n/a | deliquescent♠ | n/a |
| Tosylate | mono salts | Pattern1 | Confirmation of the salt formation 1:1 | n/a | deliquescent♠ | n/a |

Key:
♣ Crystalline
♠ Amorphous
♥ No further analysis performed
n/a Not applicable

Example 10

Crystal Structure of the Hydrochloride Salt

Crystals of hydrochloride salt were obtained by maturation between room temperature and 50° C. of a methanol solution of (2S,3R)—N-2-((3-pyridinyl)methyl)-1-azabicyclo[2.2.2]oct-3-yl)-3,5-difluorobenzamide mono-hydrochloride. The single crystal structure data are indicated in the table below. The sample was checked to be representative of the bulk

| Single Crystal Structure of the mono hydrochloride salt | | | | |
|---|---|---|---|---|
| Molecular formula | | $C_{20}H_{22}ClF_2N_3O$ | | |
| Molecular weight | | 393.86 | | |
| Crystal system | | Monoclinic | | |
| Space group | $P2_1$ | a | 10.049(1)Å | α 90° |
|  |  | b | 8.872(1)Å | β 94.088(3) |
|  |  | c | 10.491(1)Å | γ 90° |
| V | | 933.07(15)Å$^3$ | | |
| Z | | 2 | | |
| $D_c$ | | 1.402 g·cm$^{-1}$ | | |
| μ | | 0.239 mm$^{-1}$ | | |
| Source, λ | | Mo—K(alpha), 0.71073 Å | | |
| F (000) | | 412 | | |
| T | | 120(2)K | | |
| Crystal | | colourless prism, 0.3 × 0.15 × 0.11 mm | | |
| Data truncated to | | 0.80 Å | | |
| $θ_{max}$ | | 26.37° | | |
| Completeness | | 99.4% | | |
| Reflections | | 7986 | | |
| Unique reflections | | 3750 | | |
| $R_{int}$ | | 0.0135 | | |
| Flack parameter | | −0.04(3) | | |
| $R_{all}$ | | 0.0236 | | |
| $R_1$ | | 0.0231 | | |

The structure solution was obtained by direct methods, full-matrix least-squares refinement on $F^2$ with weighting $w^{-1}=σ^2(F_D^2)+(0.0435P)^2+(0.1500P)$, where $P=(F_D^2+2F_C^2)/3$, anisotropic displacement parameters, empirical absorption corrections were applied, absolute structure parameter=−0.04(3). Final $wR^2=\{Σ[w(F_C^2-F_C^2)^2]/Σ[w(F_C^2)^2]^{1/2}\}=0.0636$ for all data, conventional $R_1=0.0231$ on F values of 3684 reflections with $F_C>4σ(F_C)$, S=1.004 for all data and 252 parameters. Final Δ/σ(max) 0.001, Δ/σ(mean), 0.000. Final difference map between +0.195 and −0.136 e Å$^{-3}$.

Figure 10:
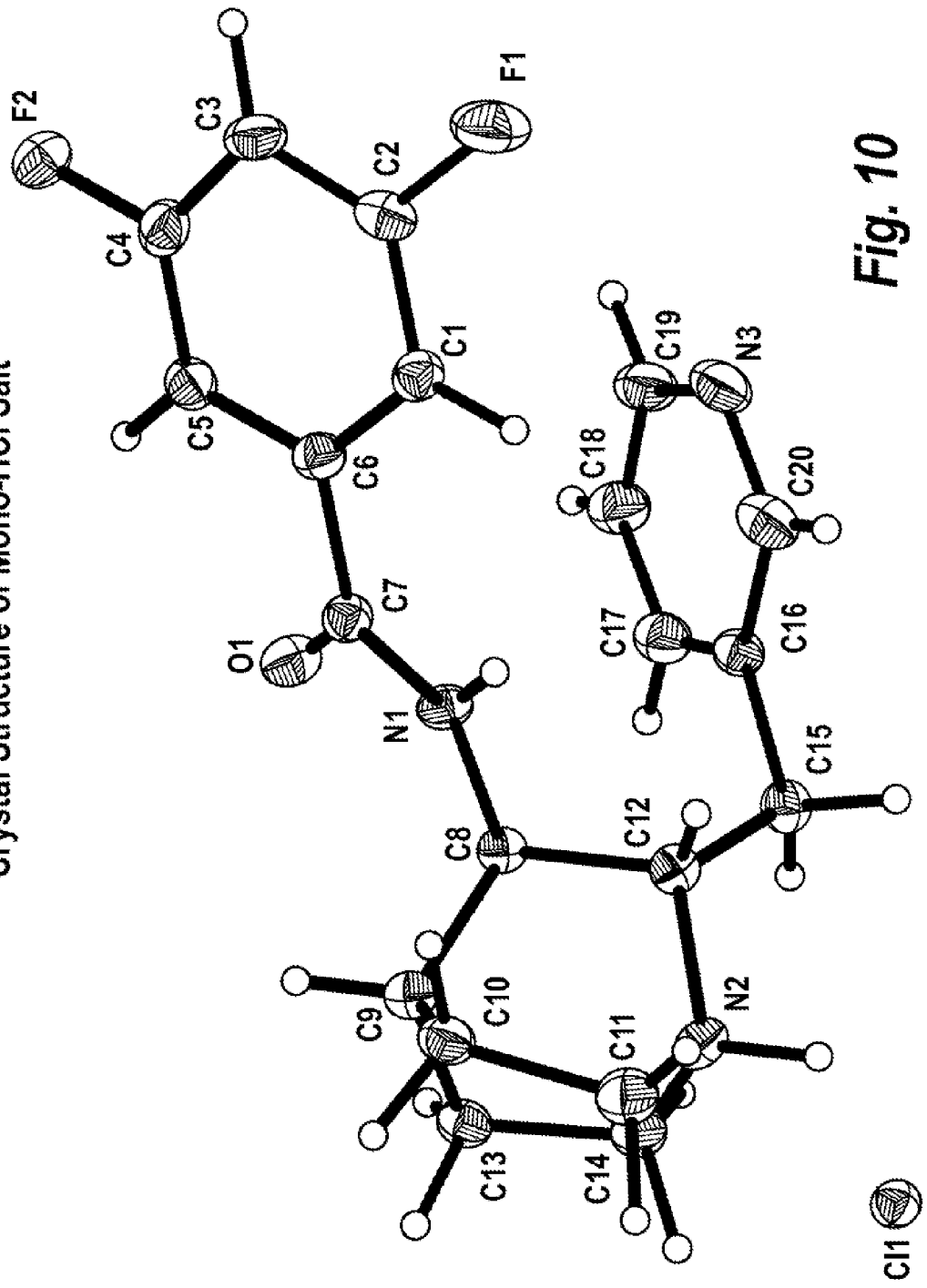
FIG. 10 is a crystal structure for Compound A mono-hydrochloride salt.

The value of the absolute structure parameter enabled the determination of the configuration of the chiral centers. This configuration is indicated in FIG. 10.

Example 11

Biological Assays

Radioligand Binding at CNS nAChRs α4β2 NNR Subtype
Preparation of Membranes from Rat Cortex:

Rats (female, Sprague-Dawley), weighing 150-250 g. were maintained on a 12 h light/dark cycle and were allowed free access to water and food supplied by PMI Nutrition International, Inc. Animals were anesthetized with 70% $CO_2$, and then decapitated. Brains were removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C.

Preparation of Membranes from SH-EP1/Human α4β2 Clonal Cells:

Cell pellets from 150 mm culture dishes were pooled, and homogenized by Polytron (Kinematica GmbH, Switzerland) in 20 milliliters of ice-cold preparative buffer. The homogenate was centrifuged at 48.000 g for 20 minutes at 4° C. The resulting pellet was re-suspended in 20 mL of ice-cold preparative buffer and stored at −20° C.

On the day of the assay, the frozen membranes were thawed and spun at 48,000×g for 20 min. The supernatant was decanted and discarded. The pellet was resuspended in Dulbecco's phosphate buffered saline (PBS, Life Technologies) pH 7.4 and homogenized with the Polytron for 6 seconds. Protein concentrations were determined using a Pierce BCA Protein Assay Kit, with bovine serum albumin as the standard (Pierce Chemical Company. Rockford, Ill.).

Membrane preparations (approximately 50 μg for human and 200-300 μg protein for rat α4β2) were incubated in PBS (50 μL and 100 μL respectively) in the presence of competitor compound (0.01 nM to 100 μM) and 5 nM [$^2$H]nicotine for 2-3 hours on ice. Incubation was terminated by rapid filtration on a multi-manifold tissue harvester (Brandel, Gaithersburg, Md.) using GF/B filters presoaked in 0.33% polyethyleneimine (w/v) to reduce non-specific binding. Tissue was rinsed 3 times in PBS, pH 7.4. Scintillation fluid was added to filters containing the washed tissue and allowed to equilibrate. Filters were then counted to determine radioactivity bound to the membranes by liquid scintillation counting (2200CA Tri-Carb LSC, Packard Instruments, 50% efficiency or Wallac Trilux 1450 MicroBeta, 40% efficiency. Perkin Elmer).

Data were expressed as disintegrations per minute (DPMs). Within each assay, each point had 2-3 replicates. The replicates for each point were averaged and plotted against the log of the drug concentration. $IC_{50}$, which is the concentration of the compound that produces 50% inhibition of binding, was determined by least squares non-linear regression. Ki values were calculated using the Cheng-Prussof equation (1973):

$$Ki = IC_{50}/(1+N/Kd)$$

where N is the concentration of [$^3$H]nicotine and Kd is the affinity of nicotine (3 nM, determined in a separate experiment).

α7 NNR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, and then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/mL. Protein was determined by the method of Lowry et al., J. Biol. Chem. 193: 265 (1951), using bovine serum albumin as the standard.

The binding of [$^3$H]MLA was measured using a modification of the methods of Davies et al., Neuropharmacol. 38: 679 (1999). [$^3$H]MLA (Specific Activity=25-35 Ci/mmol) was obtained from Tocris. The binding of [H]MLA was determined using a 2 h incubation at 21° C. Incubations were conducted in 48-well micro-titre plates and contained about 200 μg of protein per well in a final incubation volume of 300 μL. The incubation buffer was PBS and the final concentration of [$^3$H]MLA was 5 nM. The binding reaction was terminated by filtration of the protein containing bound ligand onto glass fiber filters (GF/B. Brandel) using a Brandel Tissue Harvester at room temperature. Filters were soaked in deionized water containing 0.33% polyethyleneimine to reduce non-specific binding. Each filter was washed with PBS (3×1 mL) at room temperature. Non-specific binding was determined by inclusion of 50 μM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., Biochem. Pharmacol. 22: 3099-3108 (1973).

Selectivity Vs. Peripheral nAChRs
Interaction at the Human Muscle nAChR Subtype

Activation of muscle-type nAChRs was established on the human clonal line TE671/RD, which is derived from an embryonal rhabdomyosarcoma (Stratton at al., Carcinogen 10: 899 (1989)). These cells express receptors that have pharmacological (Lukas, J. Pharmacol. Exp. Ther. 251: 175 (1989)), electrophysiological (Oswald et al., Neurosci. Lett. 96: 207 (1989)), and molecular biological profiles (Luther et al., J. Neurosci. 9: 1082 (1989)) similar to the muscle-type nAChR.

TE671/RD cells were maintained in proliferative growth phase according to routine protocols (Bencherif et al., Mol. Cell. Neurosci. 2: 52 (1991) and Bencherif et al., J. Pharmacol. Exp. Ther. 257: 946 (1991)). Cells were cultured in Dulbecco's modified Eagle's medium (Gibco/BRL) with 10% horse serum (Gibco/BRL), 5% fetal bovine serum (HyClone, Logan Utah). 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to the method described by Lukas et al., Anal. Biochem. 175: 212 (1988) On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$. Invitrogen/Gibco, pH. 7.4), taking care not to disturb the cells. Next, cells were exposed to either 100 μM of test compound, 100 μM of L-nicotine (Acros Organics) or buffer alone for 4 min. Following the exposure period, the supernatant containing the released $^{86}Rb^+$ was removed and transferred to scintillation vials.

Scintillation fluid was added and released radioactivity was measured by liquid scintillation counting.

Within each assay, each point had 2 replicates, which were averaged. The amount of $^{86}Rb^+$ release was compared to both a positive control (100 µM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChR s (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 12 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ µCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$. Invitrogen/Gibco, pH. 7.4), taking care not to disturb the cells. Next, cells were exposed to either 100 µM of test compound, 100 µM of nicotine or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_s$) of specific ion flux was also determined.

Novel Object Recognition

Memory was assessed by using the three-trial novel object recognition test. On the first day (exploratory trial), rats were allowed to explore an open arena (44.5×44.5×30.5 cm) for 6 min. On the second day (acquisition trial), rats were allowed to explore the same arena in the presence of two identical objects (both object A) for 3 minutes. On the third day (retention or recall trial), performance was evaluated by allowing the same animal to re-explore the arena for 3 minutes in the presence of two different objects: the familiar object A and a novel object B. An inter-trial interval of 24 hours was imposed between the three NOR trials. Recognition memory was assessed by comparing the time spent exploring a novel (object B) versus a familiar (object A) object during the recall trial. Recognition index was assessed for each animal and expressed as a ratio ((time B/time A+time B)×100).

Summary of Biological Data

In Vitro Pharmacology

A summary of the in vitro primary pharmacology data for (2S,3R)—N-2-((3-pyridinyl)methyl)-1-azabicyclo[2.2.2]oct-3-yl)-3,5-difluorobenzamide, or a pharmaceutically acceptable salt thereof, is presented in Table 1 and discussed in detail below.

Primary Pharmacology and Selectivity:

(2S,3R)—N-2-((3-pyridinyl)methyl)-1-azabicyclo[2.2.2]oct-3-yl)-3,5-difluorobenzamide inhibited the binding of [$^3$H]methyllycaconitine (MLA) to rat native α4β2 receptors in rat hippocampal membranes with a $K_i$ of 100 nM.

(2S,3R)—N-2-((3-pyridinyl)methyl)-1-azabicyclo[2.2.2]oct-3-yl)-3,5-difluorobenzamide inhibited the binding of [$^3$H]-nicotine to human recombinant α4β2 nicotinic receptors with a $K_i$ of 1470 nM and [$^3$H]epibatidine to rat native α4β2 receptors with a $K_i$ of 4120 nM. (2S,3R)—N-2-((3-pyridinyl)methyl)-1-azabicyclo[2.2.2]oct-3-yl)-3,5-difluorobenzamide also displayed reduced affinity for human native ganglion-type nicotinic receptors (likely α3β4), inhibiting the binding of [$^3$H]epibatidine to receptors in SH-SY5Y membranes with a $K_i$ of 48 µM, and reduced affinity for human native muscle-type nicotinic receptors (likely α1β1γδ), inhibiting the binding of [$^3$H]epibatidine to receptors in TE-671 membranes with a $K_i$ of 136 µM. (2S,3R)—N-2-((3-pyridinyl)methyl)-1-azabicyclo[2.2.2]oct-3-yl)-3,5-difluorobenzamide inhibited the binding of [$^3$H]epibatidine to the human recombinant α4β4 nicotinic receptors in SH-EP1 membranes with a $K_i$ of 19 µM.

TABLE 1

Summary of (2S,3R)-N-2-((3-pyridinyl)methyl)-1-azabicyclo[2.2.2]oct-3-yl)-3,5-difluorobenzamide in vitro pharmacology
Target affinity and activation

| | |
|---|---|
| Rat hippocampus (α7), $K_i$ | 0.1 µM |
| Rat cortex binding $K_i$ | 4.12 µM |
| Human recombinant (SH-EP 1) α4β2 binding $K_i$ | 1.47 µM |
| Human ganglionic (SH-SY5Y), $K_i$ | 48 µM |
| Human (TE671/RD) muscle, $K_i$ | 136 µM |
| Human recombinant (SH-EP1) α4β4, $K_i$ | 19 µM |

In Vivo Pharmacology

A summary of the in vivo pharmacology data for (2S, 3R)—N-2-((3-pyridinyl)methyl)-1-azabicyclo[2.2.2]oct-3-yl)-3,5-difluorobenzamide, or a pharmaceutically acceptable salt thereof, is presented in Table 2 and discussed in detail below.

TABLE 2

Summary of NOR results for (2S,3R)-N-2-((3-pyridinyl)methyl)-1-azabicyclo[2.2.2]oct-3-yl)-3,5-difluorobenzamide, or a pharmaceutically acceptable salt thereof

| Novel Object Recognition Model (NOR) | Result |
| --- | --- |
| Minimum Effective Dose (MED) | MED = 0.084 μmol/kg |
| Duration of Effect | Duration 6 h (@ 0.1 mg/kg) |
|  | Duration 18 h (@ 0.3 mg/kg) |

(2S,3R)—N-2-((3-pyridinyl)methyl)-1-azabicyclo[2.2.2]oct-3-yl)-3,5-difluorobenzamide improved long-term visual episodic/declarative memory as assessed by novel object recognition (NOR) task following oral dosing in normal rats. The results of these studies are presented in FIG. 1. The recognition index of the vehicle-treated group 24 h after the acquisition trial was 54±1% demonstrating the inability of this group to recognize the familiar object after this delay. By contrast, animals treated with (2S,3R)—N-2-((3-pyridinyl)methyl)-1-azabicyclo[2.2.2]oct-3-yl)-3,5-difluorobenzamide exhibited recognition indexes of 70±4% at the 0.84 μmol/kg dose level and 74±3% and the 0.28 μmol/kg dose level.

In a follow-up NOR study (FIG. 2), the minimum effect dose (MED) level for (2S,3R)—N-2-((3-pyridinyl)methyl)-1-azabicyclo[2.2.2]oct-3-yl)-3,5-difluorobenzamide was determined to be 0.084 μmol/kg suggesting that the rats are able to recognize the familiar object at all doses levels tested. In the "recall only" session; a subset of animals were orally dosed with water on day 1 (i.e., exploratory session) and day 2 (i.e., acquisition session) and then orally dosed with 0.28 μmol/kg (2S,3R)—N-2-((3-pyridinyl)methyl)-1-azabicyclo[2.2.2]oct-3-yl)-3,5-difluorobenzamide on day 3 (i.e., recall session). Even following a single oral administration. (2S,3R)—N-2-((3-pyridinyl)methyl)-1-azabicyclo[2.2.2]oct-3-yl)-3,5-difluorobenzamide demonstrated pro-cognitive effects at this dose level. (2S,3R)—N-2-((3-pyridinyl)methyl)-1-azabicyclo[2.2.2]oct-3-yl)-3,5-difluorobenzamide exhibited recognition indexes significantly above controls, indicating recognition of the familiar object following acute dosing. The dashed line at 65% denotes our criteria for biological cognitive enhancing activity. *$P<0.05$.

(2S3R)—N-2-((3-pyridinyl)methyl)-1-azabicyclo[2.2.2]oct-3-yl)-3,5-difluorobenzamide was evaluated for its duration of effect in the NOR task in normal rats. The results of these studies are presented in FIG. 3. The recognition index of the vehicle-treated group at 0.5 h and 24 h following dosing on the recall trial was 51±1% and 53±4%, respectively, demonstrating the inability of this group to recognize the familiar object after this delay. By contrast, animals treated with (2S,3R)—N-2-((3-pyridinyl)methyl)-1-azabicyclo[2.2.2]oct-3-yl)-3,5-difluorobenzamide (0.28 μmol/kg: oral) exhibited recognition indexes of 68±4% at 0.5 h, 71±2% at 2 h and 62±2% at 6 h suggesting that rats are able to recognize the familiar object for up to 6 h after dosing.

Figure 4:
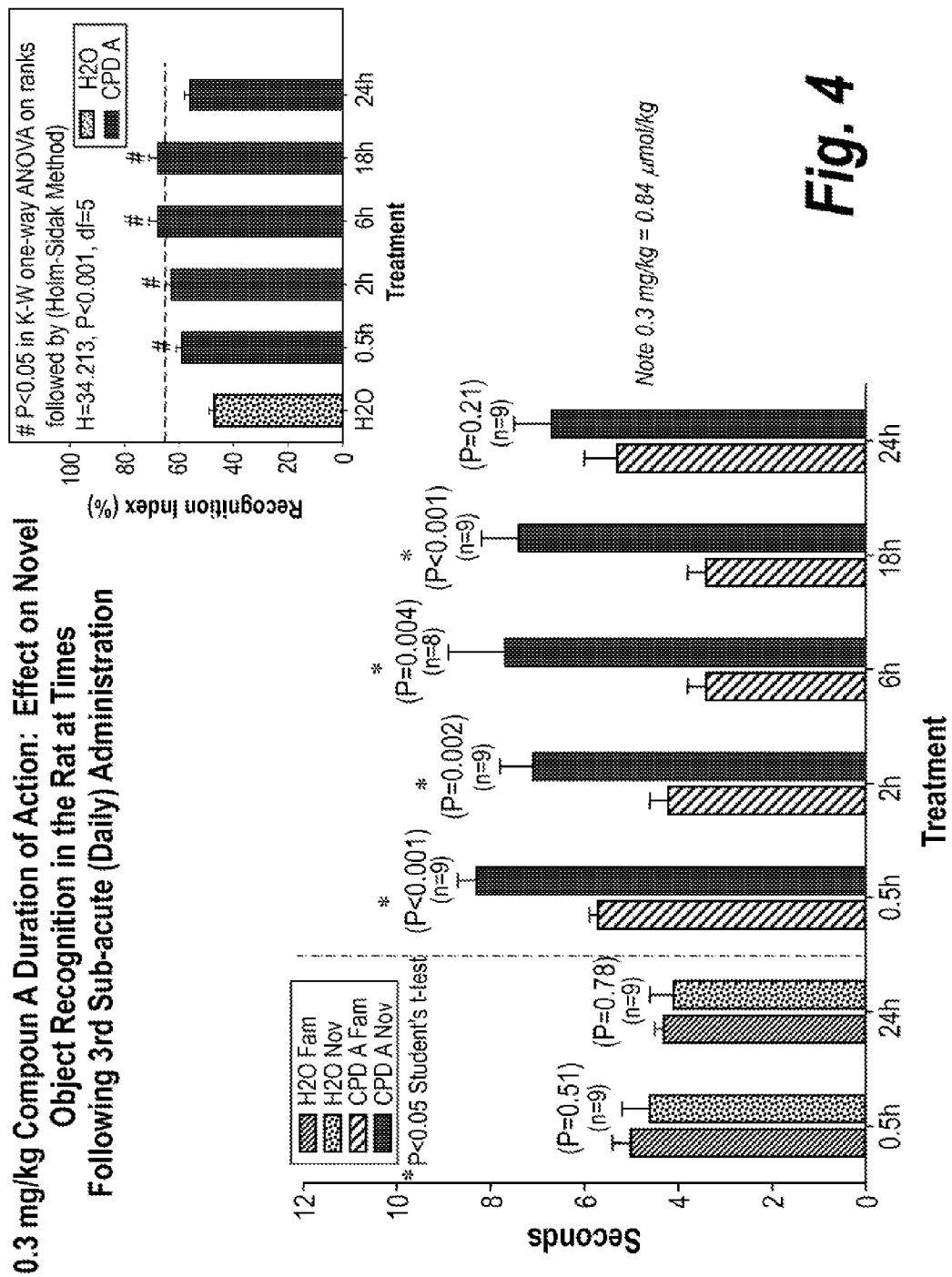
FIG. 4 depicts novel object recognition (NOR) vs. time following the 3rd administration of 0.3 mg/kg (2S,3R)—N-2-((3-pyridinyl)methyl)-1-azabicyclo[2.2.2]oct-3-yl)-3,5-difluorobenzamide or a pharmaceutically acceptable salt thereof. A statistically significant effect was observed for doses out to 18 h after dosing.

Furthermore, animals treated with (2S,3R)—N-2-((3-pyridinyl)methyl)-1-azabicyclo[2.2.2]oct-3-yl)-3,5-difluorobenzamide (0.84 μmol/kg: oral) exhibited recognition indexes of 59±2% at 0.5 h, 63±2% at 2 h, 68±3% at 6 h, and 68±3% at 18 h suggesting that rats are able to recognize the familiar object for up to 18 h after dosing at this dose level (FIG. 4). The dashed line at 65% denotes our criteria for biological cognitive enhancing activity (*$P<0.05$).

Electrophysiology

Compound A, (2S,3R)—N-2-((3-pyridinyl)methyl)-1-azabicyclo[2.2.2]oct-3-yl)-3,5-difluorobenzamide, and Compound B, (2S,3R)—N-2-((3-pyridinyl)methyl)-1-azabicyclo[2.2.2]oct-3-yl)-4-fluorobenzamide are both partial agonist at the α7 NNR. However dramatic differences exist between the two compounds in their ability to induce so-called hump currents. Hump currents are defined as the tail current observed during co-application with endogenous ACh following agonist removal. As demonstrated herein. Compound A provides an improved profile and a greater potential to modulate α7 function in conditions, such as psychotic disorders, where this neurotransmission is compromised.

The dose-response of Compounds A and B with α7 nicotinic ACh receptors was analyzed. Both Compound B and Compound A are partial agonists at α7 nicotinic receptors ($EC_{50}$=664 nM, 1.6 μM and $E_{MAX}$=46.6%, 54.4%). As shown in FIG. 5, both $EC_{50}$ and $E_{MAX}$ are comparable between these ligands.

Figure 6:
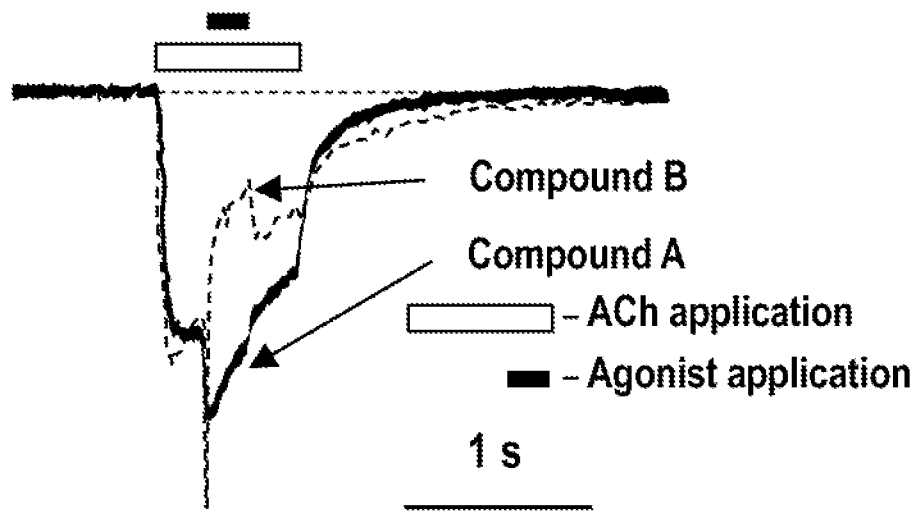
FIG. 6 depicts the electrophysiological response to co-application of each of Compound A and Compound 8 with acetylcholine (Ach).

Co-application of compounds with ACh, however, revealed substantial differences between these two ligands, as illustrated in FIG. 6. Compound B inhibited current produced by ACh, presumably due to competitive inhibition, whereas Compound A enhanced ACh-induced current. One hypothesis for this enhancement is Compound A's ability for orthosteric modulation.

Additionally, substantial differences were found when ACh was co-applied with nanomolar concentrations of Compound B or Compound A, as shown in FIGS. 7 and 8.

Figure 7A:
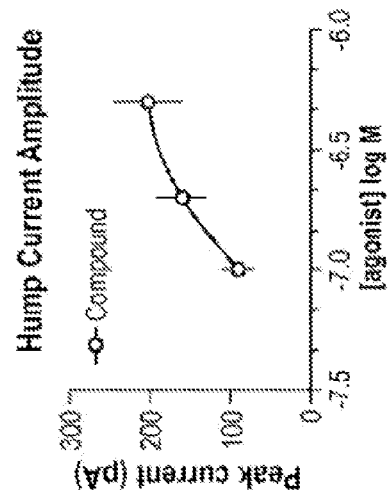
FIGS. 7A, 7B, and 7C depict electrophysiological response for interaction of Compound A with Ach, regarding activation of the nicotinic α7 receptor.

FIG. 7A represents an experimental design of loading Dynaflow chip to measure interaction of the ligand (Compound A, 200 nM) with acetylcholine (100 μM) regarding activation of nicotinic α7 receptor. The channels were prepared as follows: Control solution (channel #2), application ligand itself (channel #3), application of acetylcholine itself (channel #1), and application of mixture of acetylcholine and ligand (channel #4).

Figure 7C:
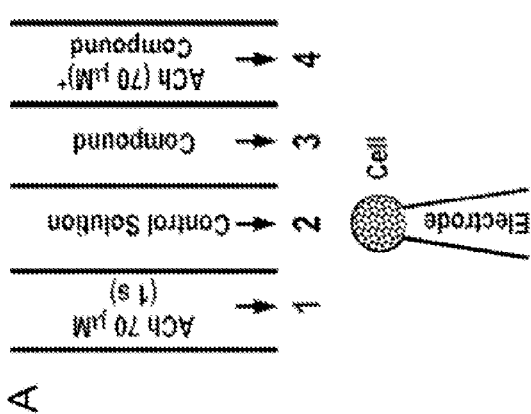
Figure 7B:
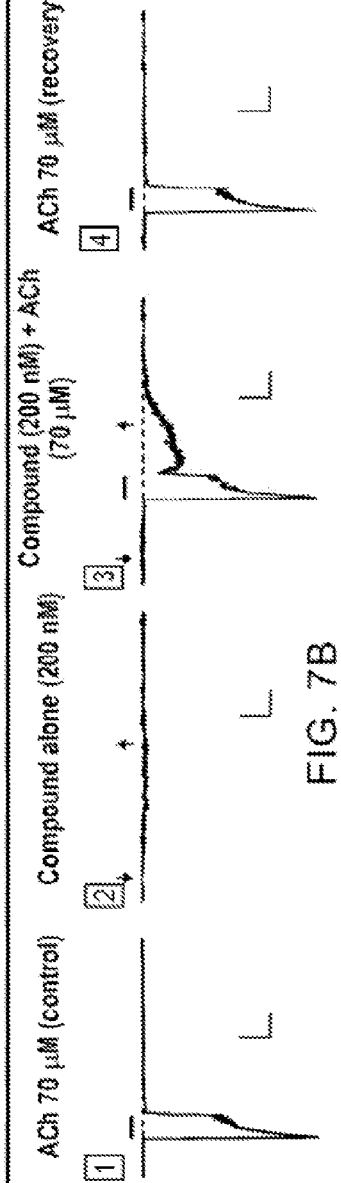

FIG. 7B shows four representative current curves obtained with different application sequences:

Curve 1, FIG. 7B: The bar above the curve indicates time of ACh application. The curve represents current induced by a one second application of 70 μM ACh. The curve illustrates the result from moving the cell from channel #2 to channel #1 for a 1 second application of ACh and back to channel 2 (washout). The application of ACh produced robust activation of current with fast recovery after washout.

Curve 4, FIG. 7B: Curve 4 represents a repetition of Curve 1 at the end of measurements after application of the ligand and ACh/ligand mixture (recovery).

Curve 2, FIG. 7B: The down/up arrows indicates time of application. Curve 2 represents a 5 second application of 200 nM of Compound A. The curve illustrates the result of moving the cell from channel #2 to channel #3 for 5 seconds. Compound A in concentration of 200 nM alone do not produce robust macro currents.

Curve 3, FIG. 7B: Curve 3 represents the interaction of the application of ACh and Compound A. Curve 3 illustrates the results from moving the cell from channel #2 to #3 (2 sec), to #4 (1 sec) and back to #3 (2 sec) and back to #2 (washout). A profound "hump" current is created due to application of Compound A following application of ACh. This current was not a result of ACh, as seen when comparing Curves 1 and 4, or Compound A, as seen in Curve 2, activation of α7 receptors alone. Rather Curve 3 illustrates an example of interaction of application of both ACh and Compound A.

FIG. 7C represents an average (n=4) of absolute values of hump currents obtained with different concentrations of Compound A (100-500 nM range). We observed a concentration dependent increase of current ($EC_{50}$=120 nM) with $E_{MAX}$ at approximately 500 nM.

Similarly, FIGS. 8A. 8B, and 8C represent the results obtained for Compound B. Upon comparing FIGS. 7A-C and with FIGS. 8A-C, substantial differences may be noted when ACh was co-applied with Compound A as compared to Compound B. Compound A enhances ACh-induced current.

Formalin Test

One of the most clinically predictive screening models of acute pain is the formalin test in mice (LeBars et al., 2001). In this paradigm, originally described by Dubuisson and Dennis (1977), a diluted solution of formalin is injected into the planter surface of a subject's (rat or mouse) rear paw and nociceptive behavior is measured; for instance, licking and biting of the injected paw. Two phases of the response are observed. First an early phase, starting immediately after injection and lasting 5-10 minutes, followed by a late phase that can last from 15-60 minutes after injection. Nociceptive response is attributed to direct chemical stimulation in the early phase and inflammation/persistent pain in the later phase (Dubuisson and Dennis, 1977). The response in the late phase also depends on changes in processing of information in the spinal cord due to the afferent barrage during the early phase (Coderre et al., 1990). An advantage of the test is that two different types of stimuli are employed in the same assay to study the possibility of varying analgesic effects of a drug in the two phases of the test (Tjølsen and Hole, 1997).

Subjects (adult male CD-1 mice (Charles River, Raleigh, N.C.) weighing approximately 20-25 grams) were removed from their home cage and weighed, then placed in a clear Plexiglas™ observation box for an acclimation period of 20-30 minutes. Mice were then removed from the observation chambers and (2S,3R)—N-2-((3-pyridinyl)methyl)-1-azabicyclo[2.2.2]oct-3-yl)-3,5-difluorobenzamide (as the hydrochloride salt in 0.9% saline) (1, 3 or 10 mg/kg s.c. (calculated with respect to the free base)), morphine (5 mg/kg; s.c.) or 0.9% saline vehicle was administered subcutaneously in a volume of 1 mL/kg. Mice were then returned to the chamber for the predetermined pretreatment time of 30 minutes for (2S,3R)—N-2-((3-pyridinyl)methyl)-1-azabicyclo[2.2.2]oct-3-yl)-3,5-difluorobenzamide and morphine.

After the test compound pretreatment time, the animals were injected with formalin solution (2.5% derived as a 1:4 dilution of 10% phosphate buffered formalin solution (Sigma):distilled water). The subject's assigned paw was grasped gently and formalin solution was injected into the paw intradermally in the middle on the dorsal side. Once injected, the subject was immediately returned to its observation chamber and a timer was started to mark the beginning of Phase I. Each subject was videotaped for the entire 40-minute session. When scoring the tapes, each subject was observed for 1 min at 5-min intervals over a 40-minute session. The time spent licking during that 1 min interval was recorded, and the presence or absence of paw favoring was noted.

For data analyses, phase I of the test was defined as 0 to 5 minutes after formalin injection, and phase II was defined as 20 to 40 minutes after formalin injection. The time spent licking during the 1 minute intervals during those time frames was recorded and graphed as mean±S.E.M. For comparisons across treatment groups, 1-way analyses of variance (ANOVAs) were performed for each phase of the session with treatment as the dependent variable. Post-hoc analyses were performed when appropriate to determine specific group differences.

The results demonstrate that although there was no statistically significant dose of (2S,3R)—N-2-((3-pyridinyl)methyl)-1-azabicyclo[2.2.2]oct-3-yl)-3,5-difluorobenzamide in reducing time spent licking in phase I, nevertheless, 10 mg/kg (2S,3R)—N-2-((3-pyridinyl)methyl)-1-azabicyclo[2.2.2]oct-3-yl)-3,5-difluorobenzamide was significant in reducing the time spent licking the paw in phase II of the formalin test (P<0.05). The positive control morphine (5 mg/kg; s.c.) was efficacious in both phases of the test. These data indicate that (2S,3R)—N-2-((3-pyridinyl)methyl)-1-azabicyclo[2.2.2]oct-3-yl)-3,5-difluorobenzamide has analgesic potential with respect to chemically-induced inflammatory/persistent pain.

Subsequent analysis of the original videotapes wherein each animal was scored across the entire time period for phase I (0-5 min after formalin) and phase II (20-40 min) revealed a similar trend for the data, but failed to achieve statistical significance for the effect of (2S,3R)—N-2-((3-pyridinyl)methyl)-1-azabicyclo[2.2.2]oct-3-yl)-3,5-difluorobenzamide on the reduction of time spent licking the affected paw in either phase I or phase II.

Reference is made to: Coderre T J, Vaccarino A L, Melzack R (1990), Central nervous system plasticity in the tonic pain response to subcutaneous formalin injection, *Brain Res.* 535: 155-158; Dubuisson D and Dennis S G (1977). The formalin test: A quantitative study of the analgesic effects of morphine, meperidine, and brain stem stimulation in rats and cats. *Pain* 4: 161-174; Malmberg A B and Bannon A W (2002). Unit 8.9: Models of nociception: hot-plate, tail-flick, and formalin tests in rodents, *Current Protocols in Neuroscience*; and Tjølsen A and Hole K (1997), Animal models of analgesia, In: *Handbook of Experimental Pharmacology Volume* 130: *The Pharmacology of Pain* (Eds. A. Dickenson and J.-M. Besson), Springer Verlag, New York pp. 1-20.

Complete Freund's Adjuvant (CFA)-Induced Thermal Hyperalgesia

Injection of complete Freund's adjuvant (CFA) in rats is commonly used to evaluate compounds with potential for use as drugs in treatment of mono-arthritis (osteo-arthritis) and other inflammatory conditions. Signs of hyperalgesia develop within 24 h (Schaible and Grubb, 1993).

(2S,3R)—N-2-((3-pyridinyl)methyl)-1-azabicyclo[2.2.2]oct-3-yl)-3,5-difluorobenzamide was evaluated for possible analgesia effect in the CFA-induced thermal hyperalgesia test in rats using methods similar to those described by Walker and colleagues (2003). Briefly, adult male Sprague-Dawley rats (BioLasco, Taiwan) weighing 180±20 g on receipt were randomly assigned to treatment groups of n=8 per group. Animals each received a sub plantar injection (0.1 mL) of CFA (DIFCO, 264010; 0.1% solution) to the right hind paw at 24 h prior to experimental testing. Thermal hyperalgesia was tested using a Paw/Tail stimulator analgesia meter (IITC Model-336G, IITC, USA) with a thermally regulated glass floor set at 30° C. A subject was placed within a plastic box atop an elevated glass floor and a light beam located under the glass floor was directed at the plantar surface of the right hind paw. The time required for the animal to withdraw the paw from the thermal stimulus was automatically recorded. The intensity of the light was adjusted to evoke an average group baseline latency from 12-14 seconds (pre-CFA) and a cut-off latency of 20 seconds was imposed. The latency for paw withdrawal was obtained for each rat and defined as the heat pain threshold.

Twenty-four hours after CFA injection, subjects were preselected (for clear presence of thermal hyperalgesia) for experimentation only if the latency to withdrawal was less than 75% of the baseline. Test substance, morphine and vehicle were administered by subcutaneous (s.c.) injection at time 0. The post-treatment level of thermal hyperalgesia was then measured at 60 minutes post-treatment. One-way ANOVA followed by Dunnett's test was applied for comparison between test substance treated groups and vehicle control group. Activity was considered significant at the P<0.05 level.

Figure 13:
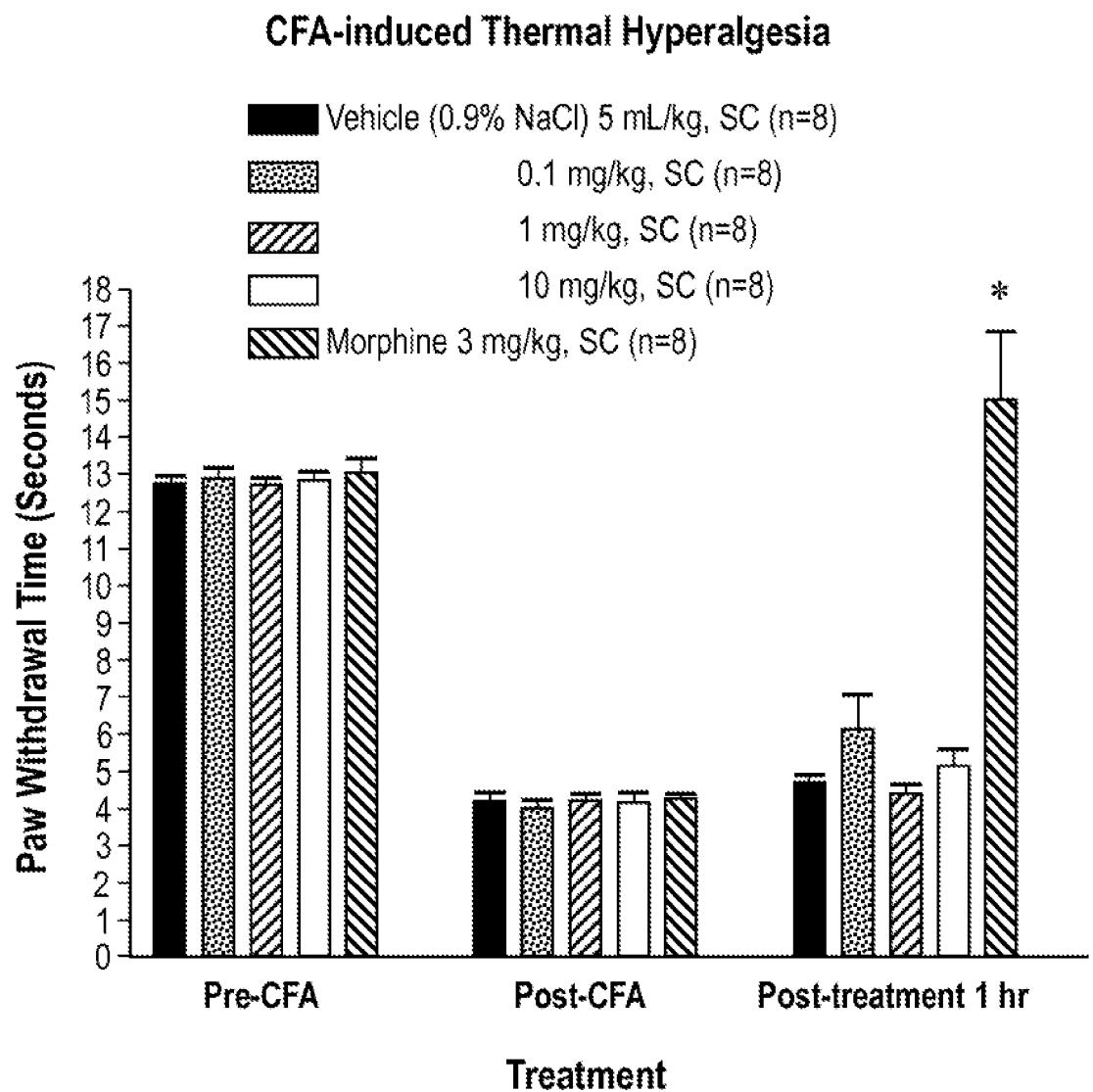
FIG. 13 illustrates the results of assessment of (2S,3R)—N-2-((3-pyridinyl)methyl)-1-azabicyclo[2.2.2]oct-3-yl)-3,5-difluorobenzamide in CFA-induced thermal hyperalgesia. Test substance, morphine, and vehicle were each administered subcutaneously to groups of 8 SD rats 24 hours after CFA injection. The thermal hyperalgesia was performed prior to CFA injection (pre-CFA), before treatment, and 1 hour after SC injection. One-way ANOVA followed by the Dunnett's test was applied to compare between the treatment groups and the vehicle controlled group. Differences are considered significant at the *P<0.05 level.

Overall, subcutaneous (s.c.) administration of (2S,3R)—N-2-((3-pyridinyl)methyl)-1-azabicyclo[2.2.2]oct-3-yl)-3,5-difluorobenzamide at 0.1, 1 or 10 mg/kg was not associated with any significant analgesic effect at 1 hour post-dose on CFA-induced thermal hyperalgesia in rats compared with the vehicle (0.9% saline) control group. In contrast, the concurrently run reference standard morphine (3 mg/kg s.c.) produced significant analgesic activity at 1 hour after dosing. See FIG. 13. Reference is made to: Schaible H-G and Grubb B D (1993). Afferent and spinal mechanisms of joint pain, *Pain* 55: 5-54; and Walker K M. Urban L, Medhurst S J: Patel S. Panesar M. Fox A J and Mcintyre P (2003), The VR1 antagonist capsazepine reverses mechanical hyperalgesia in models of inflammatory and neuropathic pain, *JPET* 304: 56-62.

Streptozotocin (STZ)—Induced Diabetic Neuropathy (as Evidenced by Allodynia)

Peripheral neuropathy, a major complication of diabetes, often results in spontaneous pain or the perception of pain from contact with a normally non-noxious stimulus. Such neuropathic pain is experienced by 20-24% of diabetic patients, or approximately 30 million people worldwide (Schmader, 2002). The streptozotocin (STZ)—induced diabetes model in rats provides a means to evaluate the efficacy of test compounds that offer therapeutic potential for peripheral neuropathy and to understand their putative mechanism of action. In this model, a single injection of STZ, an antibiotic that mimics clinical diabetes by causing irreversible damage to the pancreatic β and α-cells leads to chronic hyperglycemia, nerve dysfunction and pain sensitivity. The current study utilizes the STZ rat model of diabetic neuropathy to investigate the effects of (2S,3R)—N-2-((3-pyridinyl)methyl)-1-azabicyclo[2.2.2]oct-3-yl)-3,5-difluorobenzamide on mechanical allodynia, an assessment of pain.

Diabetes was induced by a 0.5 ml injection of streptozotocin (60 mg/kg) dissolved in citrate buffer (pH=6) into the tail vein of each rat. The development of diabetes was confirmed by measuring the blood glucose levels (BGL) of all animals on study day 3 (BGL>300 mg/dL). BGL was measured again on study day 14 and only the animals that showed tactile allodynia were tested again for their BGL on study day 21. BGL was measured on study day 16 for animals that did not show tactile allodynia on study day 14. These animals were tested again for their BGL at study day 23.

(2S,3R)—N-2-((3-pyridinyl)methyl)-1-azabicyclo[2.2.2]oct-3-yl)-3,5-difluorobenzamide (0.1, 1 or 10 mg/kg p.o.) was administered as a solution of the hydrochloride salt in water once daily starting on study day 14 or study day 16 and continuing through study day 21 or 23, respectively. The control article gabapentin (in 0.9% saline, 150 mg/kg i.p.) was only administered on allodynia test days. Test item, vehicle or control article administration was based on evaluation of allodynia on study day 14. If allodynia was not present on study day 14, the animal was evaluated again at study day 16. Pain response was measured either on study days 14 and 21 or 16 and 23, 30 minutes after Test Item administration.

For the allodynia assessments, Von Frey filaments were used according to the methods of Chaplan and colleagues (1994). Briefly, the rats were placed in an enclosure and positioned on a metal mesh surface, but allowed to move freely. The rats' cabins were covered with red cellophane to diminish environmental distributions. The test began after cessation of exploratory behavior.

Rodents exhibit a paw withdrawal reflex when its paw is unexpectedly touched. When the tip of a Von Frey fiber of given length and diameter was pressed against the skin at right angles, the force of application increases as long as the researcher continued to advance the probe until the fiber bent. After the fiber bent, the probe was advanced, causing the fiber to bend more, but without additional force being applied. The animal would indicate sensation by pulling back its paw. In the absence of a paw withdrawal response to the initially selected filament, a stronger stimulus was presented: in the event of paw withdrawal, the next weaker stimulus was chosen. In this fashion, the resulting pattern of positive and negative responses was used to determine the paw withdrawal threshold.

The set of Von Frey monofilaments provide an approximate logarithmic scale of actual force and a linear scale of perceived intensity. Below is a table showing the force (g) and its corresponding size of monofilaments.

| | Size | | | | | | | | | | | | | | | | | | |
|---|---|---|---|---|---|---|---|---|---|---|---|---|---|---|---|---|---|---|---|
| | 1.65 | 2.36 | 2.44 | 2.83 | 3.22 | 3.61 | 3.84 | 4.08 | 4.17 | 4.31 | 4.56 | 4.74 | 4.93 | 5.07 | 5.18 | 5.46 | 5.88 | 6.10 | 6.45 | 6.65 |
| Force (g) | 0.008 | 0.02 | 0.04 | 0.07 | 0.16 | 0.40 | 0.60 | 1.00 | 1.40 | 2.00 | 4.00 | 6.00 | 8.00 | 10 | 15 | 26 | 60 | 100 | 180 | 300 |

All normally distributed data are presented as means±SEM, as well as the animals' individual values followed by a student T-test (Software: Microsoft® Excel). A p value<0.05 is considered to represent a significant difference. Due to the non-normal distribution of the allodynia data, descriptions of those data are provided as both mean (+SEM) and median values in order to represent their imprecise nature and skewed distribution.

The Von Frey data are presented as the minimum force (g) needed to withdraw each hind leg. A decrease in pain threshold was recorded 14/16 days post STZ injection. This decrease was expressed as an increase in the animal's sensitivity to the Von Frey filaments. The average and group median withdrawal force of the vehicle treated animals at baseline before STZ injection was 57.57±2.43 (group median=60 g). On study days 14/16, the median paw withdrawal force was significantly lower (20.5–22.14±2.36 g; <0.01 vs. baseline; median=20.5 g) indicating tactile allodynia prior to (2S,3R)—N-2-((3-pyridinyl)methyl)-1-azabicyclo[2.2.2]oct-3-yl)-3,5-difluorobenzamide treatment. At study termination (study days 21/23), tactile allodynia was still observed post treatment (20.46 t 3.31 g; p<0.01 vs. baseline; median=8 g).

Overall, Treatment with 1 mg/kg (2S,3R)—N-2-((3-pyridinyl)methyl)-1-azabicyclo[2.2.2]oct-3-yl)-3,5-difluorobenzamide inhibited allodynia 30 minutes after its administration on study days 14/16 as compared to pretreatment (p<0.01) or to the Vehicle control (p<0.05). Treatment with (2S,3R)—N-2-((3-pyridinyl)methyl)-1-azabicyclo[2.2.2]oct-3-yl)-3,5-difluorobenzamide at a dose of 10 mg/kg inhibited allodynia 30 minutes after its administration on study days 14/16 as compared to pretreatment (p=0.012). Treatment with (2S,3R)—N-2-((3-pyridinyl)methyl)-1-azabicyclo[2.2.2]oct-3-yl)-3,5-difluorobenzamide at a dose of 1 mg/kg inhibited allodynia 30 minutes after their administration on study days 21/23 as compared to pretreatment (p=0.012). Treatment with (2S,3R)—N-2-((3-pyridinyl)methyl)-1-azabicyclo[2.2.2]oct-3-yl)-3,5-difluorobenzamide at a dose of 10 mg/kg (Group 11M) inhibited allodynia 30 minutes after its administration on study days 21/23 as compared to the Vehicle control (p<0.05). Treatment with the positive control, gabapentin, reversed the tactile allodynia significantly in all treatment days as compared to pretreatment (study days 14/16 and 21/23; p<0.01) or as compared to the Vehicle control (study days 21/23; p<0.01). At study termination (study day 21/23), insulin levels in the serum were analyzed. No significant differences in insulin levels were observed. (2S,3R)—N-2-((3-pyridinyl)methyl)-1-azabicyclo[2.2.2]oct-3-yl)-3,5-difluorobenzamide at all doses was administered every day starting on study day 14 or 16 through study day 21 or 23, respectively. The pain test was performed prior to Test Article injection (pre-TI injection) and 30 minutes after Test Article administration (post-TI injection). The positive control, gabapentin, was administered 2 hours before pain testing on study days 14 or 16 and 21 or 23. Treatment with the positive control, gabapentin, reversed the tactile allodynia significantly in all treatment days as compared to pretreatment and to the vehicle: 22.77±3.77 g (median=15 g) vs. 45.62±4.24 g (median=60 g) in pre and post treatment, respectively, on study days 14/16, p<0.01; 28.23±4.91 g (median=20.5 g) vs. 50.88±4.12 g (median=60 g) in pre and post treatment, respectively, on study days 21/23, p<0.01; 45.62±4.24 g (median=60 g) vs. 26.61±4.41 g (median=15 g) in the vehicle group on study days 14/16, p<0.01; 50.88±4.12 g (median=60 g) vs. 20.46±3.31 g (median=10 g) in the vehicle group on study days 21/23, p<0.01.

Immediately after the Von Frey testing on the termination days, blood was collected. At the end of the study, the animals were euthanized with ketamine/xylazine solution (IP). Approximately 0.5-0.7 ml of blood was collected via cardiac puncture in tubes containing the anti-coagulant (K3 EDTA). The blood samples were kept chilled on ice and centrifuged within 30 minutes of collection. To obtain plasma, blood was centrifuged for 10 minutes at 3000 rpm. Plasma was transferred into labeled tubes and stored upright and frozen at approximately −20° C. until shipment. Each sample was labeled with the compound number and animal number.

All animals gained weight during the study. There were no significant differences in body weight gain between the groups.

The mean blood glucose levels increased in all animals. Baseline was 108.86±1.03 mg/dl and increased to 390.99*6.47 mg/dl on study day 3. No statistical differences were found between groups. High glucose levels were also measured on study days 14/16 and 21/23 based on the results for allodynia at study day 14. At the end of the study (study day 21 and 23) the mean blood glucose level was 403.86±8.45 mg/dl.

At study termination, insulin levels in serum were analyzed. The insulin level in the Vehicle control at study termination was 0.79±0.41 µg/l. No significant differences in insulin levels between treatments were observed.

Figure 14:
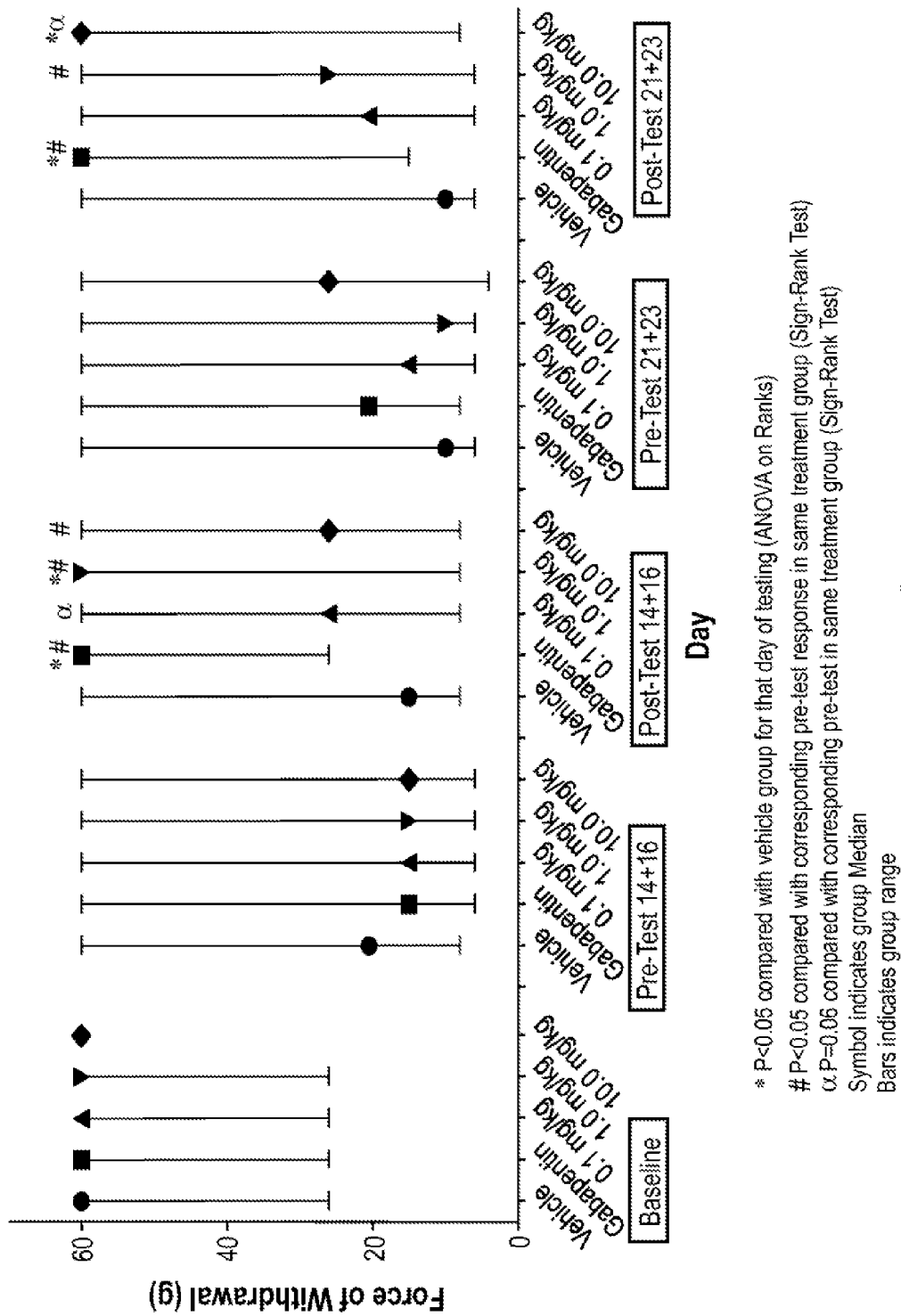
FIG. 14 illustrates the results of Von Frey assessment indicating that (2S,3R)—N-2-((3-pyridinyl)methyl)-1-azabicyclo[2.2.2]oct-3-yl)-3,5-difluorobenzamide is effective in reducing diabetic neuropathy pain at doses of 1 mg/kg and 10 mg/kg compared to the Vehicle treated group.

The results of Von Frey assessment indicate that (2S,3R)—N-2-((3-pyridinyl)methyl)-1-azabicyclo[2.2.2]oct-3-yl)-3,5-difluorobenzamide is effective in reducing diabetic neuropathy pain at doses of 1 mg/kg and 10 mg/kg compared to the Vehicle treated group. See FIG. 14.

Reference is made to: Chaplan S R, Bach F W, Pogrel J W, Chung J M, Yaksh T L (1994). Quantitative assessment of tactile allodynia in the rat paw, J. Neurosci. Methods 53: 55-63; Schumader K E (2002). Epidemiology and impact on quality of life of postherpetic neuralgia and painful diabetic neuropathy. *Clinical Journal of Pain* 18: 350-354; and Sommer C (2003). Painful neuropathies, *Curr. Opin. Neurol.* 16: 623-628.

Murine Model of Type 2 Diabetes Mellitus

The db/db mouse, a well established model of type 2 diabetes mellitus, is a leptin-deficient mutant that expresses an obese phenotype and also commonly expresses metabolic symptoms including hyperglycemia, hyperlipidemia and hyperinsulinemia (Halaas et al., 1995 and Lee et al., 1996). This experimental animal model of diabetes was employed in a study designed to determine the effects of (2S,3R)—N-2-((3-pyridinyl)methyl)-1-azabicyclo[2.2.2]oct-3-yl)-3,5-difluorobenzamide on body mass and several additional metabolic parameters.

In this study, (2S,3R)—N-2-((3-pyridinyl)methyl)-1-azabicyclo[2.2.2]oct-3-yl)-3,5-difluorobenzamide was repeatedly administered orally (via gavage) at 1.0 mg/kg once daily starting from the age of approximately 3 weeks and continuing throughout the 7-week study. Nondiabetic heterozygote littermate mice (db/+; designated "Db") were used as controls. Body weight and food intake were determined twice weekly. The α7 antagonist methyllycaconitine (MLA) was also given concurrently via gavage at 3 mg/kg daily to selected cohorts of db/db (designated "db") or db/+mice. At the end of the 7-week dosing regimen, total growth rates (overall body weight gain) and average daily food intake were calculated. In addition, glucose levels were assessed in mice fasted overnight. Furthermore, blood sample analytes from mice fasted overnight were collected for measurements of tumor necrosis factor-a (TNF-α), triglycerides and glycosylated hemoglobin (HbA1c). All data are expressed as mean±SEM. For each parameter investigated, differences among all groups were compared by one-way ANOVA with post-hoc Neuman-Keuls multiple comparison test.

Overall, daily administration over the course of 7 weeks of (2S,3R)—N-2-((3-pyridinyl)methyl)-1-azabicyclo[2.2.2] oct-3-yl)-3,5-difluorobenzamide to obese db/db mice resulted in a significant decrease in all parameters measured compared with control obese db/db mice treated with vehicle. With respect to total body weight gain, average daily food consumption, glycosylated HbA1c levels and plasma concentration of TNF-α, co-administration of MLA attenuated the effect. Although attenuation of plasma glucose and triglycerides was not significantly attenuated by co-administration of MLA with (2S,3R)—N-2-((3-pyridinyl)methyl)-1-azabicyclo[2.2.2]oct-3-yl)-3,5-difluorobenzamide, there was a trend toward that reversal.

Figure 15:
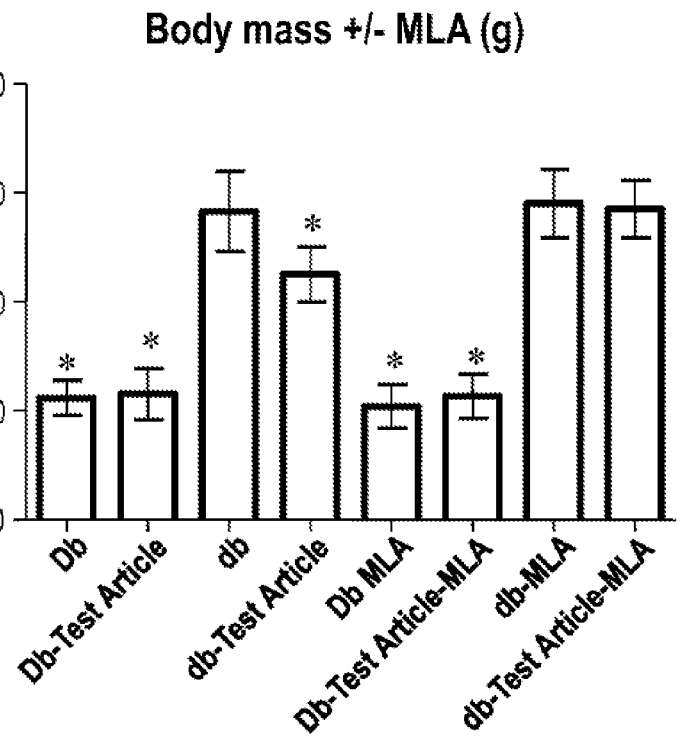
FIG. 15 illustrates comparison weight gain as significantly lower in the (2S,3R)—N-2-((3-pyridinyl)methyl)-1-azabicyclo[2.2.2]oct-3-yl)-3,5-difluorobenzamide-treated obese ("db-Test Article") mice. Notably, animals that were co-administered MLA with (2S,3R)—N-2-((3-pyridinyl)methyl)-1-azabicyclo[2.2.2]oct-3-yl)-3,5-difluorobenzamide failed to show the reduced weight gain exhibited by the obese rats administered (2S,3R)—N-2-((3-pyridinyl)methyl)-1-azabicyclo[2.2.2]oct-3-yl)-3,5-difluorobenzamide alone.

As illustrated in FIG. 15, At the end of seven weeks of treatment, between ages 3 and 10 weeks, total body weight gain in the vehicle control-treated obese group ("db") was significantly greater than that of lean vehicle control animals ("Db"). By comparison, weight gain was significantly lower in the (2S,3R)—N-2-((3-pyridinyl)methyl)-1-azabicyclo [2.2.2]oct-3-yl)-3,5-difluorobenzamide-treated obese ("db-Test Article") mice. Notably, animals that were co-administered MLA with (2S,3R)—N-2-((3-pyridinyl)methyl)-1-azabicyclo[2.2.2]oct-3-yl)-3,5-difluorobenzamide failed to show the reduced weight gain exhibited by the obese rats administered (2S,3R)—N-2-((3-pyridinyl)methyl)-1-azabicyclo[2.2.2]oct-3-yl)-3,5-difluorobenzamide alone.

Figure 16:
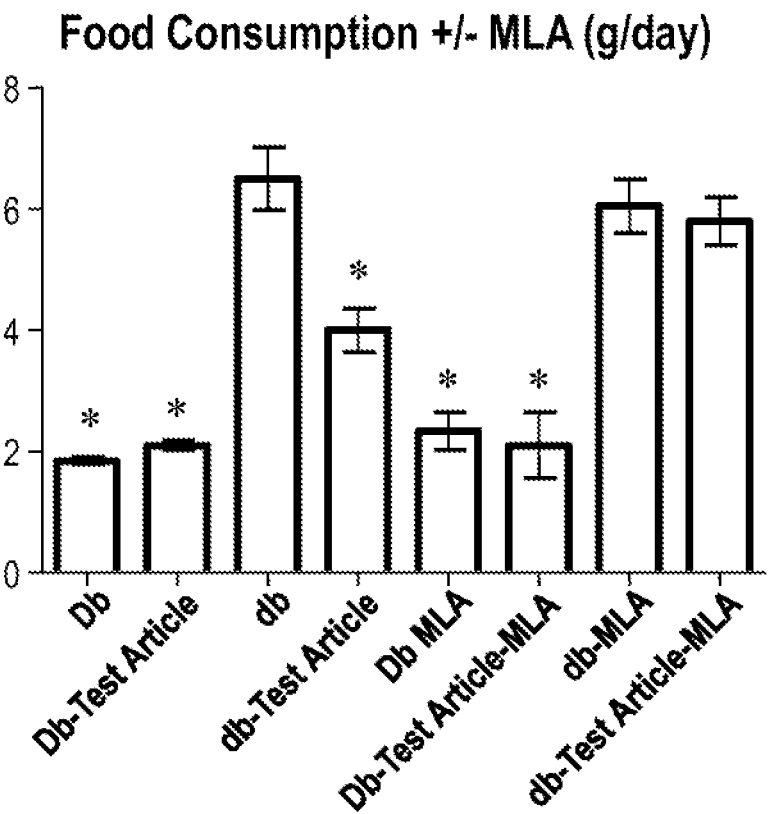
FIG. 16 illustrates average food consumption was significantly lower in the (2S,3R)—N-2-((3-pyridinyl)methyl)-1-azabicyclo[2.2.2]oct-3-yl)-3,5-difluorobenzamide-treated obese mice ("db-Test Article") than in the obese controls. The food consumption of the lean mice was unaffected by (2S,3R)—N-2-((3-pyridinyl)methyl)-1-azabicyclo[2.2.2]oct-3-yl)-3,5-difluorobenzamide ("Db-Test Article"). Animals that were co-administered MLA with (2S,3R)—N-2-((3-pyridinyl)methyl)-1-azabicyclo[2.2.2]oct-3-yl)-3,5-difluorobenzamide failed to show the reduced daily average food consumption exhibited by the obese rats administered (2S,3R)—N-2-((3-pyridinyl)methyl)-1-azabicyclo[2.2.2]oct-3-yl)-3,5-difluorobenzamide alone.

As shown in FIG. 16. The daily food intake in vehicle control obese group ("db") was significantly greater than that of lean vehicle controls ("Db"). Average food consumption was significantly lower in the TC-(2S,3R)—N-2-((3-pyridinyl)methyl)-1-azabicyclo[2.2.2]oct-3-yl)-3,5-difluorobenzamide-treated obese mice ("db-Test Article") than in the obese controls. The food consumption of the lean mice was unaffected by (2S,3R)—N-2-((3-pyridinyl)methyl)-1-azabicyclo[2.2.2]oct-3-yl)-3,5-difluorobenzamide ("Db-Test Article"). Animals that were co-administered MLA with (2S,3R)—N-2-((3-pyridinyl)methyl)-1-azabicyclo[2.2.2]oct-3-yl)-3,5-difluorobenzamide failed to show the reduced daily average food consumption exhibited by the obese rats administered (2S,3R)—N-2-((3-pyridinyl)methyl)-1-azabicyclo[2.2.2]oct-3-yl)-3,5-difluorobenzamide alone.

Figure 17:
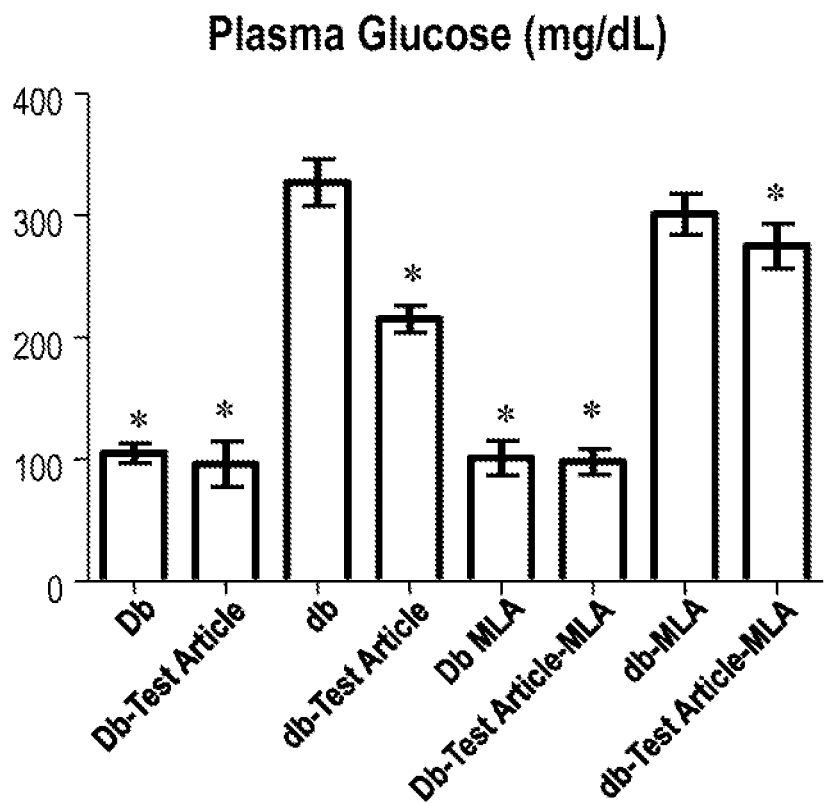
FIG. 17 illustrates that (2S,3R)—N-2-((3-pyridinyl)methyl)-1-azabicyclo[2.2.2]oct-3-yl)-3,5-difluorobenzamide significantly inhibited fasting plasma glucose levels in obese mice ("db-Test Article"). However, this effect was not reversed by co-administration with MLA.

As shown in FIG. 17, (2S,3R)—N-2-((3-pyridinyl)methyl)-1-azabicyclo[2.2.2]oct-3-yl)-3,5-difluorobenzamide significantly inhibited fasting plasma glucose levels in obese mice ("db-Test Article"). However, this effect was not reversed by co-administration with MLA.

Figure 18:
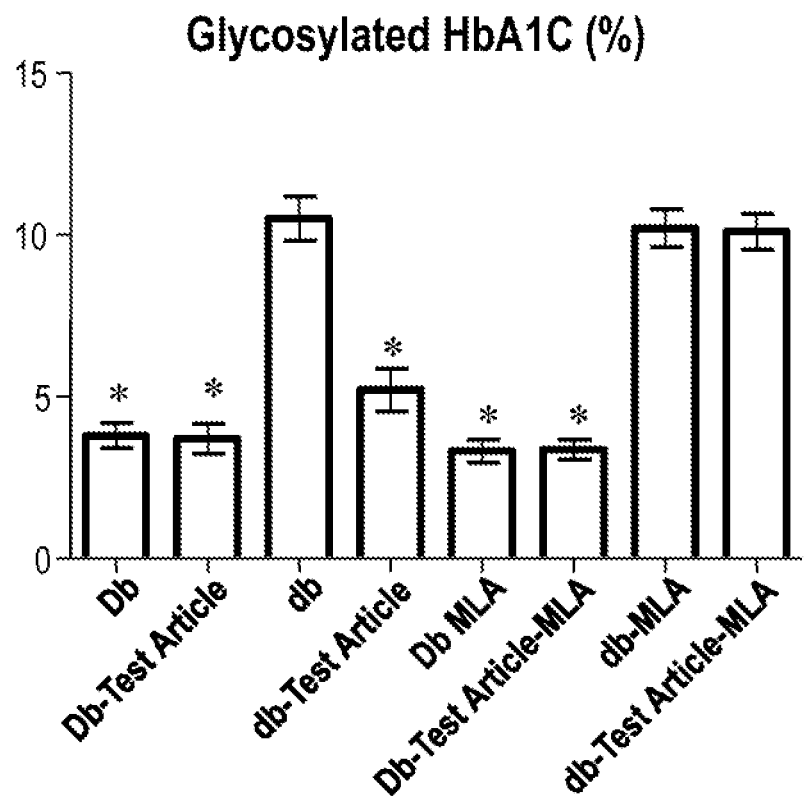
FIG. 18 illustrates that (2S,3R)—N-2-((3-pyridinyl)methyl)-1-azabicyclo[2.2.2]oct-3-yl)-3,5-difluorobenzamide significantly inhibited glycosylated HbA1c levels in obese mice ("db-Test Article"). The reduction in glycosylated HbA1c by (2S,3R)—N-2-((3-pyridinyl)methyl)-1-azabicyclo[2.2.2]oct-3-yl)-3,5-difluorobenzamide was attenuated by co-administration of MLA.

As shown in FIG. 18, (2S,3R)—N-2-((3-pyridinyl)methyl)-1-azabicyclo[2.2.2]oct-3-yl)-3,5-difluorobenzamide significantly inhibited glycosylated HbA1c levels in obese mice ("db-Test Article"). The reduction in glycosylated HbA1c by (2S,3R)—N-2-((3-pyridinyl)methyl)-1-azabicyclo[2.2.2]oct-3-yl)-3,5-difluorobenzamide was attenuated by co-administration of MLA.

Figure 19:
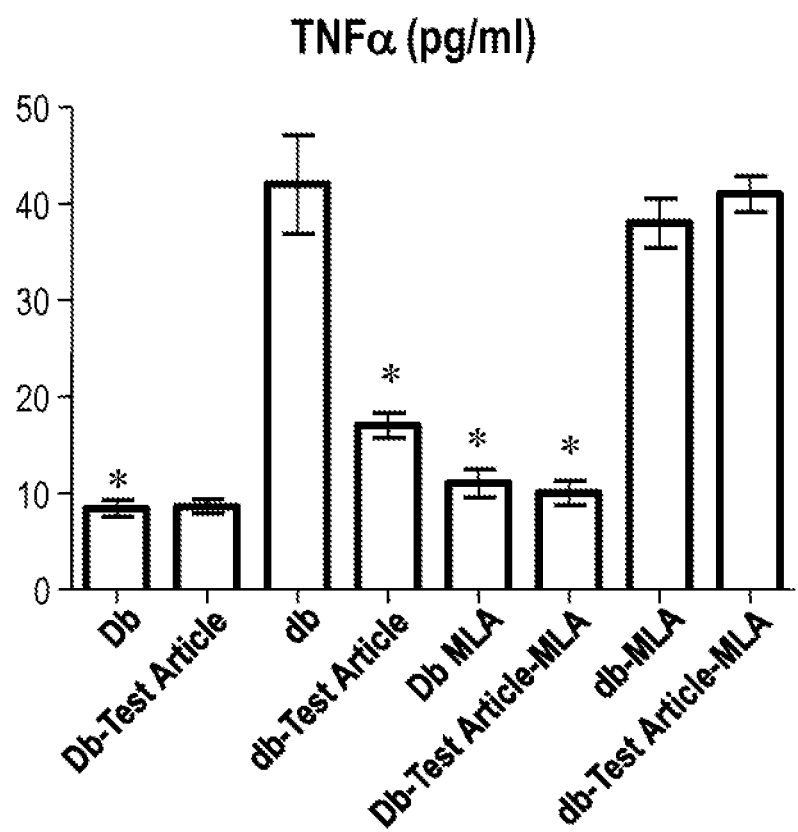
FIG. 19 illustrates that (2S,3R)—N-2-((3-pyridinyl)methyl)-1-azabicyclo[2.2.2]oct-3-yl)-3,5-difluorobenzamide significantly reduced the pro-inflammatory cytokine TNF alpha in obese mice ("db-Test Article"). These effects were inhibited by co-administration of the alpha7 antagonist MLA.

As shown in FIG. 19, (2S,3R)—N-2-((3-pyridinyl)methyl)-1-azabicyclo[2.2.2]oct-3-yl)-3,5-difluorobenzamide significantly reduced the pro-inflammatory cytokine TNF alpha in obese mice ("db-Test Article"). These effects were inhibited by co-administration of the alpha7 antagonist MLA.

Figure 20:
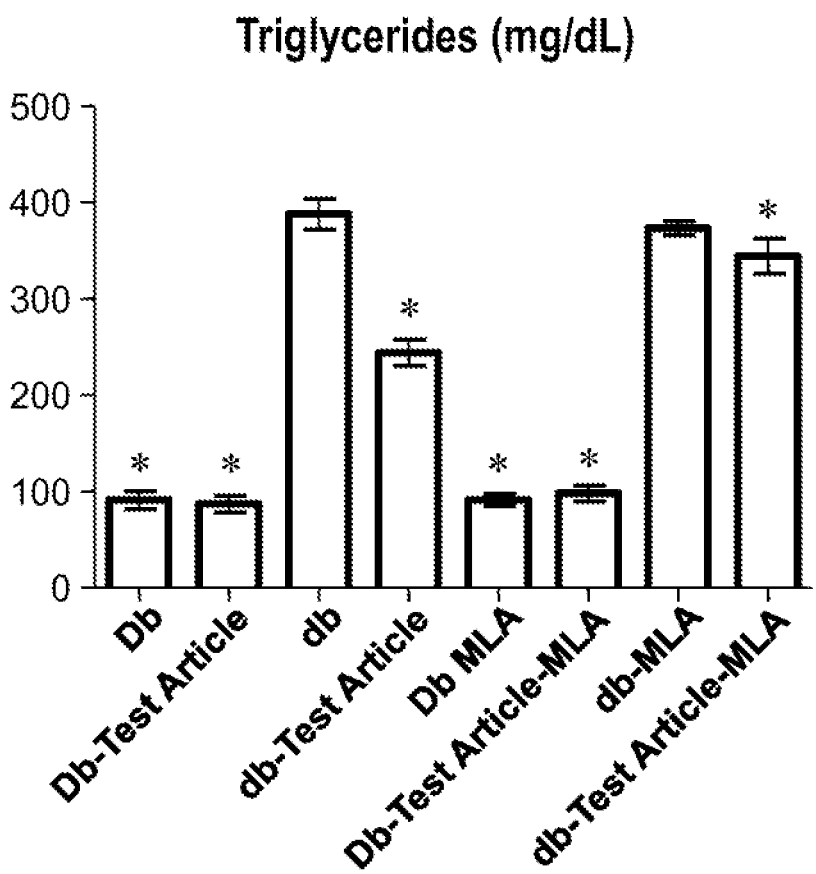
FIG. 20 illustrates that (2S,3R)—N-2-((3-pyridinyl)methyl)-1-azabicyclo[2.2.2]oct-3-yl)-3,5-difluorobenzamide resulted in significantly lower triglyceride levels in obese mice ("db-Test Article") compared with vehicle-treated controls ("db"). The reduction in triglycerides by (2S,3R)—N-2-((3-pyridinyl)methyl)-1-azabicyclo[2.2.2]oct-3-yl)-3,5-difluorobenzamide was not attenuated by co-administration of MLA.

As shown in FIG. 20, (2S,3R)—N-2-((3-pyridinyl)methyl)-1-azabicyclo[2.2.2]oct-3-yl)-3,5-difluorobenzamide resulted in significantly lower triglyceride levels in obese mice ("db-Test Article") compared with vehicle-treated controls ("db"). The reduction in triglycerides by (2S,3R)—N-2-((3-pyridinyl)methyl)-1-azabicyclo[2.2.2]oct-3-yl)-3,5-difluorobenzamide was not attenuated by co-administration of MLA.

Pulmonary, Airway Hyperresponsiveness, Penh Measurement

Using the method of Hamelmann et al, (2S,3R)—N-2-((3-pyridinyl)methyl)-1-azabicyclo[2.2.2]oct-3-yl)-3,5-difluorobenzamide was evaluated for possible inhibition of airway hyper-responsiveness in mice. Briefly, ovalbumin (OVA)-sensitized animals, 12 animals per group, were challenged by nasal inhalation with aerosolized 5% OVA for 25 min on days 21, 23, and 25. The mice were treated with vehicle or (2S,3R)—N-2-((3-pyridinyl)methyl)-1-azabicyclo[2.2.2]oct-3-yl)-3,5-difluorobenzamide subcutaneously (s.c.) twice daily from day 21 to day 26 or once daily intratracheally (i.t.), preceding ovalbumin aerosol challenge by 30 min on days 21, 23 and 25 as well as methacholine challenge or bronchoalveolar lavage fluids (BALF) harvest on day 26. Dexamethasone, the reference standard, was administered at 3 mg/kg orally (p.o.) once daily 60 min before OVA challenge on day 21, 23 and 25 and 60 min before methacholine provocation or BALF harvest on day 26. Noninvasive measurements of airway responsiveness were performed by using whole body plethysmography, in which increases in enhanced pause (Penh) serve as an index of airway obstruction. Responses to inhaled methacholine were measured and calculated as percentage of respective baseline values. Unpaired Student's t-test was used for comparison between the vehicle control and the sham group; one-way ANOVA and Dunnett's post-hoc analyses were applied for comparison between the vehicle control and treated groups. Statistical significance is considered at P<0.05.

Figure 21:
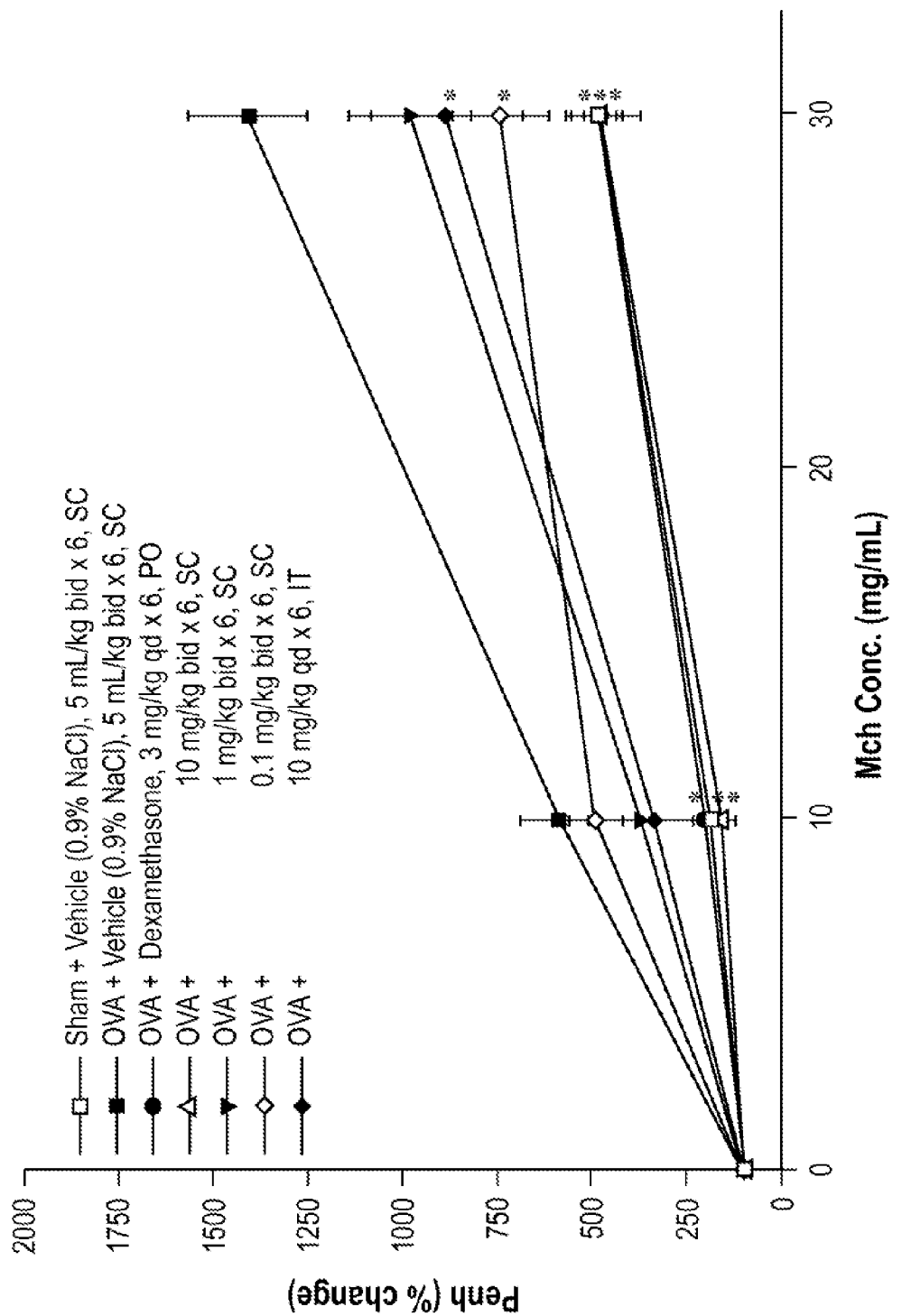
FIG. 21 illustrates the effect of (2S,3R)—N-2-((3-pyridinyl)methyl)-1-azabicyclo[2.2.2]oct-3-yl)-3,5-difluorobenzamide on % changes in Penh response to methacholine challenge in ovalbumin-sensitized mice. (2S,3R)—N-2-((3-pyridinyl)methyl)-1-azabicyclo[2.2.2]oct-3-yl)-3,5-difluorobenzamide and vehicle were administered subcutaneously bid or given intratracheally qd for 6 consecutive days from day 21 to day 25 at 30 min before OVA challenge and the last dosing was administrated at 30 min before MCh provocation on day 26 The Penh values were determined. One-way ANOVA followed by Dunnett's test was applied for comparison between the OVA immunized vehicle and other treatment groups. *P<0.05 vs. OVA-vehicle control.

FIG. 21 illustrates the effect of (2S,3R)—N-2-((3-pyridinyl)methyl)-1-azabicyclo[2.2.2]oct-3-yl)-3,5-difluorobenzamide on % changes in Penh response to methacholine challenge in ovalbumin-sensitized mice. The Penh response to methacholine (10 and 30 mg/mL) was significantly augmented in OVA-sensitized animals compared to sham control. Dexamethasone at 3 mg/kg PO caused a significant inhibition of the methacholine (10 and 30 mg/mL)-induced increase in Penh values, both in absolute and % values compared to vehicle-treated OVA animals, indicating efficacy against airway hyperresponsiveness. (2S,3R)—N-2-((3-pyridinyl)methyl)-1-azabicyclo[2.2.2]oct-3-yl)-3,5-difluorobenzamide at 0.1, 1, and 10 mg/kg bid s.c. caused significant inhibition of the methacholine-induced increase in Penh values; 10 mg/kg IT was also associated with significant inhibition.

The effect of (2S,3R)—N-2-((3-pyridinyl)methyl)-1-azabicyclo[2.2.2]oct-3-yl)-3,5-difluorobenzamide on white blood cell counts/differential cell counts and % white blood cell count/differential cell counts in ovalbumin sensitized mice are illustrated in Figures Y and Z, respectively. A significant increase in total WBC, neutrophils, lymphocytes, monocytes and eosinophils was noted in BALF in OVA-sensitized animals vs. sham control, which was inhibited significantly by dexamethasone. (2S,3R)—N-2-((3-pyridinyl)methyl)-1-azabicyclo[2.2.2]oct-3-yl)-3,5-difluorobenzamide at 0.1 and 1 mg/kg SC, but not at 10 mg/kg SC, significantly reduced total WBC and eosinophils in BALF: (2S,3R)—N-2-((3-pyridinyl)methyl)-1-azabicyclo[2.2.2]oct-3-yl)-3,5-difluorobenzamide at 10 mg/kg SC reduced monocytes, lymphocytes were reduced at 0.1 and 1 mg/kg SC as well as at 10 mg/kg IT.

These results demonstrate that multiple administrations of (2S,3R)—N-2-((3-pyridinyl)methyl)-1-azabicyclo[2.2.2]oct-3-yl)-3,5-difluorobenzamide at 0.1, 1 and 10 mg/kg bid s.c. and at 10 mg/kg i.t, vs dexamethasone affords significant protection against airway hyper-responsiveness in OVA sensitized mouse model (as evidenced by reduced Penh response to methacholine challenge using whole body plethysmography in mice) and is associated with significant reduction in eosinophils and white blood cells in BALF (which, however, lacks a consistent dose-response relationship).

FIG. 21 illustrates the effect of (2S,3R)—N-2-((3-pyridinyl)methyl)-1-azabicyclo[2.2.2]oct-3-yl)-3,5-difluorobenzamide on % changes in Penh response to methacholine challenge in ovalbumin-sensitized mice. (2S,3R)—N-2-((3-pyridinyl)methyl)-1-azabicyclo[2.2.2]oct-3-yl)-3,5-difluorobenzamide and vehicle were administered subcutaneously bid or given intratracheally qd for 6 consecutive days from day 21 to day 25 at 30 min before OVA challenge and the last dosing was administrated at 30 min before MCh provocation on day 26. The Penh values were determined. One-way ANOVA followed by Dunnett's test was applied for comparison between the OVA immunized vehicle and other treatment groups. *P<0.05 vs. OVA-vehicle control.

Figure 22:
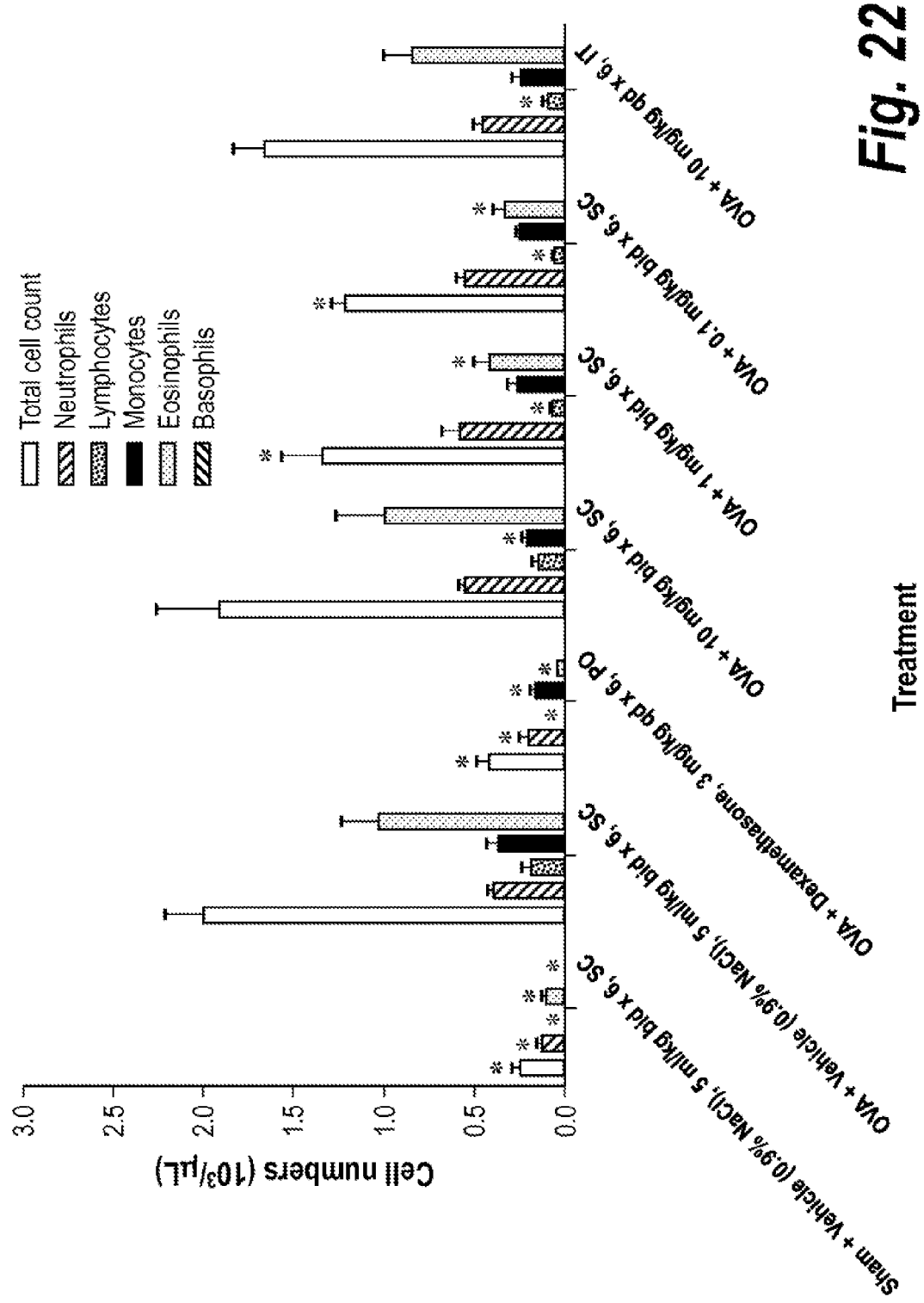
FIG. 22 illustrates the effect of (2S,3R)—N-2-((3-pyridinyl)methyl)-1-azabicyclo[2.2.2]oct-3-yl)-3,5-difluorobenzamide on white blood cell counts and differential cell counts in ovalbumin sensitized mice. (2S,3R)—N-2-((3-pyridinyl)methyl)-1-azabicyclo[2.2.2]oct-3-yl)-3,5-difluorobenzamide and vehicle were administered subcutaneously bid or were given intratracheally qd for 6 consecutive days from day 21 to day 25 at 30 minutes before OVA challenge and the last dosing was administrated at 30 minutes before bronchoalveolar lavage fluid harvest on day 26. The total white blood cell count and differential cell counts were determined. One-way ANOVA followed by Dunnett's test was applied for comparison between the OVA immunized vehicle and other treatment groups. *P<0.05 vs. OVA-vehicle control.

FIG. 22 illustrates the effect of (2S,3R)—N-2-((3-pyridinyl)methyl)-1-azabicyclo[2.2.2]oct-3-yl)-3,5-difluorobenzamide on white blood cell counts and differential cell counts in ovalbumin sensitized mice. (2S,3R)—N-2-((3-pyridinyl)methyl)-1-azabicyclo[2.2.2]oct-3-yl)-3,5-difluorobenzamide and vehicle were administered subcutaneously bid or were given intratracheally qd for 6 consecutive days from day 21 to day 25 at 30 minutes before OVA challenge and the last dosing was administrated at 30 minutes before bronchoalveolar lavage fluid harvest on day 26. The total white blood cell count and differential cell counts were determined. One-way ANOVA followed by Dunnett's test was applied for comparison between the OVA immunized vehicle and other treatment groups. *P<0.05 vs. OVA-vehicle control.

Figure 23:
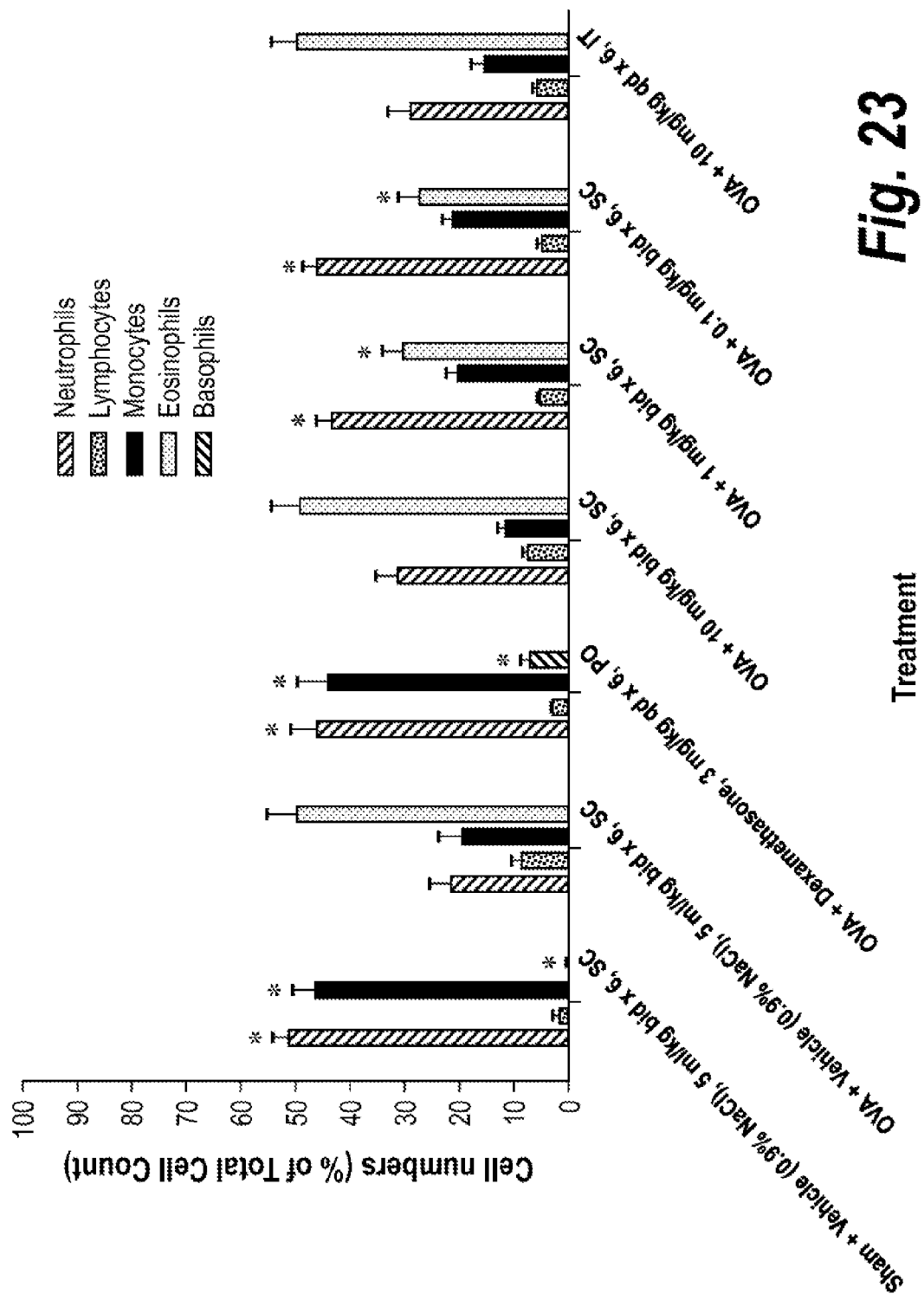
FIG. 23 illustrates the effect of (2S,3R)—N-2-((3-pyridinyl)methyl)-1-azabicyclo[2.2.2]oct-3-yl)-3,5-difluorobenzamide on % white blood cell count and differential cell counts in ovalbumin sensitized mice. (2S,3R)—N-2-((3-pyridinyl)methyl)-1-azabicyclo[2.2.2]oct-3-yl)-3,5-difluorobenzamide and vehicle were administered subcutaneously bid or were given intratracheally qd for 6 consecutive days from day 21 to day 25 at 30 minutes before OVA challenge and the last dosing was administrated at 30 minutes before bronchoalveolar lavage fluid harvest on day 26. The total white blood cell count and differential cell counts were determined. One-way ANOVA followed by Dunnett's test was applied for comparison between the OVA immunized vehicle and other treatment groups. *P<0.05 vs. OVA-vehicle control.

FIG. 23 illustrates the effect of (2S,3R)—N-2-((3-pyridinyl)methyl)-1-azabicyclo[2.2.2]oct-3-yl)-3,5-difluorobenzamide on % white blood cell count and differential cell counts in ovalbumin sensitized mice. (2S,3R)—N-2-((3-pyridinyl)methyl)-1-azabicyclo[2.2.2]oct-3-yl)-3,5-difluorobenzamide and vehicle were administered subcutaneously bid or were given intratracheally qd for 6 consecutive days from day 21 to day 25 at 30 minutes before OVA challenge and the last dosing was administrated at 30 minutes before bronchoalveolar lavage fluid harvest on day 26. The total white blood cell count and differential cell counts were determined. One-way ANOVA followed by Dunnett's test was applied for comparison between the OVA immunized vehicle and other treatment groups. *$P<0.05$ vs. OVA-vehicle control.

Reference is made to: Hamelmann E. Schwarze J. Takeda K, Oshiba A, Larsen G L. Irvin C G, and Gelfand E W, Noninvasive measurement of airway responsiveness in allergic mice using barometric plethysmography, *Am J Respir Crit Care Med.* 156:766-775, 1997.

Test compounds for the experiments described herein were employed in free or salt form. Unless otherwise specified, the compound provided for in vivo testing was (2S,3R)—N-2-((3-pyridinyl)methyl)-1-azabicyclo[2.2.2]oct-3-yl)-3,5-difluorobenzamide hydrochloride, with dosage amounts given assuming the free base form.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A method for treating a neuropathy, comprising administering to a patient in need thereof an effective amount of a compound (2S,3R)—N-2-((3-pyridinyl)methyl)-1-azabicyclo[2.2.2]oct-3-yl)-3,5-difluorobenzamide (Formula I) or a pharmaceutically acceptable salt thereof.

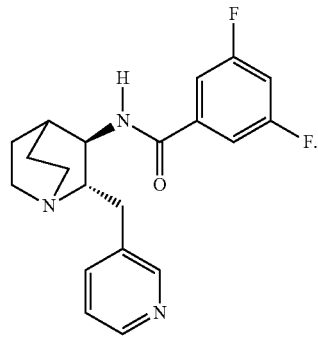

Formula I